US008819591B2

(12) United States Patent
Wang et al.

(10) Patent No.: US 8,819,591 B2
(45) Date of Patent: Aug. 26, 2014

(54) TREATMENT PLANNING IN A VIRTUAL ENVIRONMENT

(75) Inventors: Bai Wang, Palo Alto, CA (US); Kun Zhang, San Jose, CA (US); Xiangyong Cheng, Cupertino, CA (US); I-Ning Chang, Fremont, CA (US); Robert W. Hill, San Jose, CA (US); Colin Sims, Chesterfield, MO (US); Hongwu Wang, Palo Alto, CA (US)

(73) Assignee: Accuray Incorporated, Sunnyvale, CA (US)

( * ) Notice: Subject to any disclaimer, the term of this patent is extended or adjusted under 35 U.S.C. 154(b) by 276 days.

(21) Appl. No.: 12/799,072

(22) Filed: Apr. 15, 2010

(65) Prior Publication Data

US 2011/0107270 A1 May 5, 2011

Related U.S. Application Data

(60) Provisional application No. 61/280,278, filed on Oct. 30, 2009.

(51) Int. Cl.
*G06F 3/048* (2013.01)
*G06F 3/0481* (2013.01)

(52) U.S. Cl.
CPC .................. *G06F 3/04815* (2013.01)
USPC .......................................... 715/850

(58) Field of Classification Search
USPC .......................................... 715/848, 849, 852
See application file for complete search history.

(56) References Cited

U.S. PATENT DOCUMENTS

| 6,529,758 | B2 * | 3/2003 | Shahidi | 600/407 |
|---|---|---|---|---|
| 6,692,441 | B1 * | 2/2004 | Poland et al. | 600/443 |
| 2001/0031920 | A1 * | 10/2001 | Kaufman et al. | 600/431 |
| 2002/0172401 | A1 * | 11/2002 | Lees et al. | 382/109 |
| 2004/0214128 | A1 * | 10/2004 | Sachdeva et al. | 433/24 |
| 2004/0243538 | A1 * | 12/2004 | Kockro et al. | 707/1 |
| 2006/0274885 | A1 * | 12/2006 | Wang et al. | 378/65 |
| 2006/0274925 | A1 * | 12/2006 | West et al. | 382/131 |
| 2007/0003131 | A1 * | 1/2007 | Kaufman | 382/154 |
| 2007/0092864 | A1 * | 4/2007 | Reinhardt et al. | 435/4 |
| 2007/0147671 | A1 * | 6/2007 | Di Vincenzo et al. | 382/128 |
| 2007/0230765 | A1 * | 10/2007 | Wang et al. | 382/132 |
| 2007/0279436 | A1 * | 12/2007 | Ng et al. | 345/624 |
| 2008/0118137 | A1 * | 5/2008 | Chen et al. | 382/131 |
| 2008/0144910 | A1 * | 6/2008 | Weissenborn | 382/131 |
| 2009/0002366 | A1 * | 1/2009 | Kanitsar et al. | 345/419 |
| 2010/0268067 | A1 * | 10/2010 | Razzaque et al. | 600/424 |

(Continued)

OTHER PUBLICATIONS

"MIPAV User Guide," Dec. 2, 2008, National Institutes of Health, Center for Information Technology, available online at http://mipav.cit.nih.gov/documentation/userguide/MIPAVUsersGuideVolume1.pdf.*

(Continued)

*Primary Examiner* — Matt Kim
*Assistant Examiner* — Maryam Ipakchi
(74) *Attorney, Agent, or Firm* — Lowenstein Sandler LLP

(57) ABSTRACT

A method and apparatus for treatment planning are described. A treatment planning system provides a computer-simulated virtual environment including a virtual artifact that is a three-dimensional simulation of a patient anatomy, wherein the three-dimensional simulation is generated from one or more diagnostic images taken of the patient anatomy. The treatment planning system performs a treatment planning operation associated with the virtual artifact in response to a user interaction with the virtual environment.

23 Claims, 48 Drawing Sheets
(22 of 48 Drawing Sheet(s) Filed in Color)

(56) References Cited

U.S. PATENT DOCUMENTS

2012/0203053 A1* 8/2012 Kilby et al. .................. 600/1
2012/0253200 A1* 10/2012 Stolka et al. ............... 600/459
2013/0102831 A1* 4/2013 Kindlein et al. .............. 600/7

OTHER PUBLICATIONS

Kang et al., "Interactive 3D editing tools for image segmentation," Medical Image Analysis 8 (2004) 35-46.*

Patel et al., "A virtual reality solution for evaluation of radiotherapy plans," Radiotherapy and Oncology 82 (2007) 218-221.*

Ellis, Stephen R., "What Are Virtual Environments?" IEEE Computer Graphics & Applications, Jan. 1994, pp. 17-22.

Mourant, Ronald R., et al., "Training in a Virtual Stereoscopic Environment," Proceedings of the Human Factors and Ergonomics Society 46th Annual Meeting, 2002, pp. 2206-2209.

Wang, Guangyu, et al., "A Comparative Study of Monoscopic and Stereoscopic Display for a Probe-Positioning Task," Medicine Meets Virtual Reality, Feb. 2009, 3 pages, Long Beach, California.

Melanie Tory and Colin Swindells, "Comparing ExoVis, Orientation Icon, and In-Place 3D Visualization Techniques", Webster's Encyclopedic Unabridged Dictionary of the English Language (New York: Portland House, 1989), pp. 500-507.

* cited by examiner

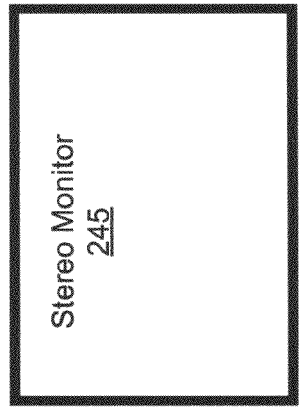
Figure 2B — Single Stereo Monitor 235
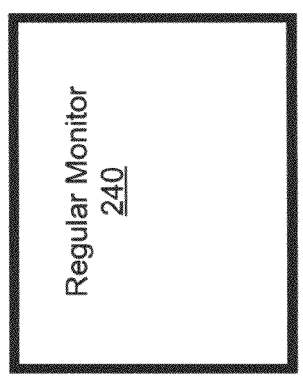
Figure 2C — Regular Monitor 240, Stereo Monitor 245
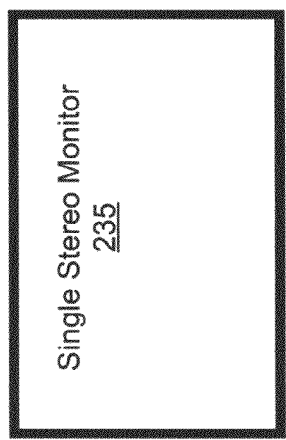
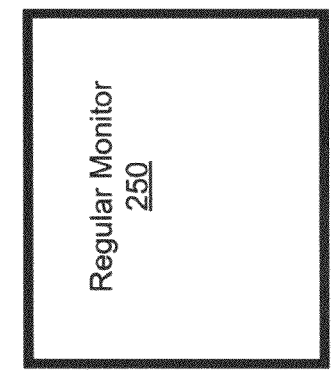
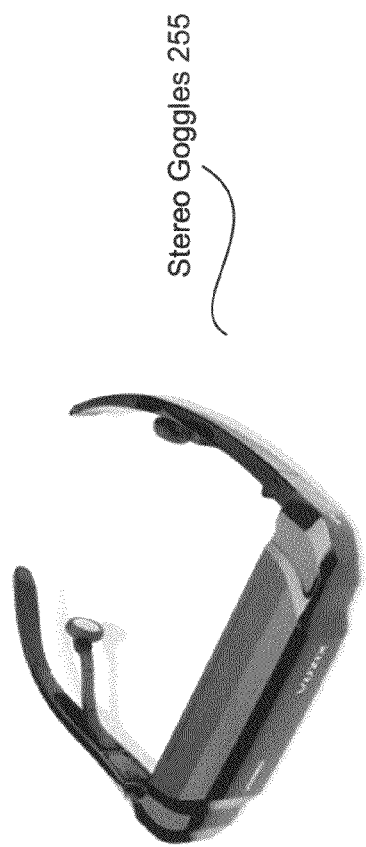
Figure 2D — Regular Monitor 250, Stereo Goggles 255

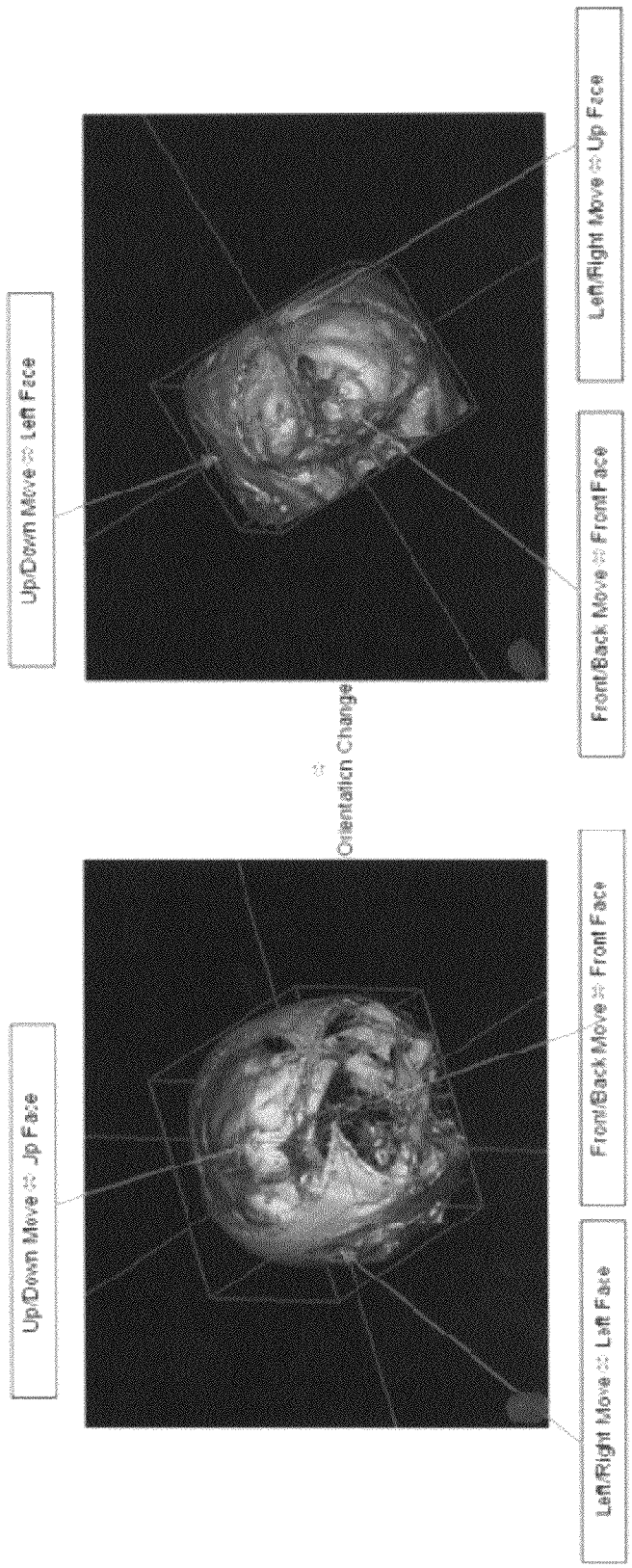

TREATMENT PLANNING IN A VIRTUAL ENVIRONMENT

RELATED APPLICATIONS

This patent application claims the benefit under 35 U.S.C. §119(e) of U.S. Provisional Application No. 61/280,278, filed Oct. 30, 2009, which is herein incorporated by reference.

TECHNICAL FIELD

The present invention relates generally to radiation treatment and, more particularly, to treatment planning in a virtual environment.

BACKGROUND

Tumors and lesions are types of pathological anatomies characterized by abnormal growth of tissue resulting from the uncontrolled, progressive multiplication of cells, while serving no physiological function.

Pathological anatomies can be treated with an invasive procedure, such as surgery, which can be harmful and full of risks for the patient. A non-invasive method to treat a pathological anatomy (e.g., tumor, legion, vascular malformation, nerve disorder, etc.) is external beam radiation treatment, which includes radiation therapy (radiotherapy) and radiation surgery (radiosurgery). Radiotherapy and radiosurgery differ in the amount of radiation delivered to a patient in a treatment session. The amount of radiation in an individual session or fraction utilized in radiotherapy treatment sessions is typically about an order of magnitude smaller, as compared to the amount used in a radiosurgery session. For convenience, the term "radiation treatment" is used herein to mean radiosurgery and/or radiotherapy unless otherwise noted by the magnitude of the radiation.

Treatment planning is performed to determine the radiation dose that will be delivered to the target region and the radiation dose that will be delivered to surrounding tissue. A conventional treatment planning system, such as that developed by Accuray, Inc. uses an interface that uses 2D input devices such as a mouse or trackpad and monoscopic displays such as a standard computer monitor. Such a treatment planning system is described in U.S. Patent Publication No. 20060274885, entitled, "Treatment Planning Software And Corresponding User Interface," published Dec. 7, 2006. In such a treatment planning system, image slices are used as a primary working space. Target and critical regions are identified on axial, coronal, or sagittal images slice by slice. Existing treatment planning systems do not provide a virtual environment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention is illustrated by way of example, and not by way of limitation, in the figures of the accompanying drawings.

FIGS. 2B-2D illustrate examples of three different possible display setups for a treatment planning system, in accordance with embodiments of the present invention.

FIG. 20B illustrates a user interface for the contour task as displayed in a monoscopic display of a treatment planning system, in accordance with one embodiment of the present invention.

FIGS. 30B and 30C show how sub-volume faces can be manipulated in the virtual environment, in accordance with one embodiment of the present invention.

DETAILED DESCRIPTION

Figure 1A:
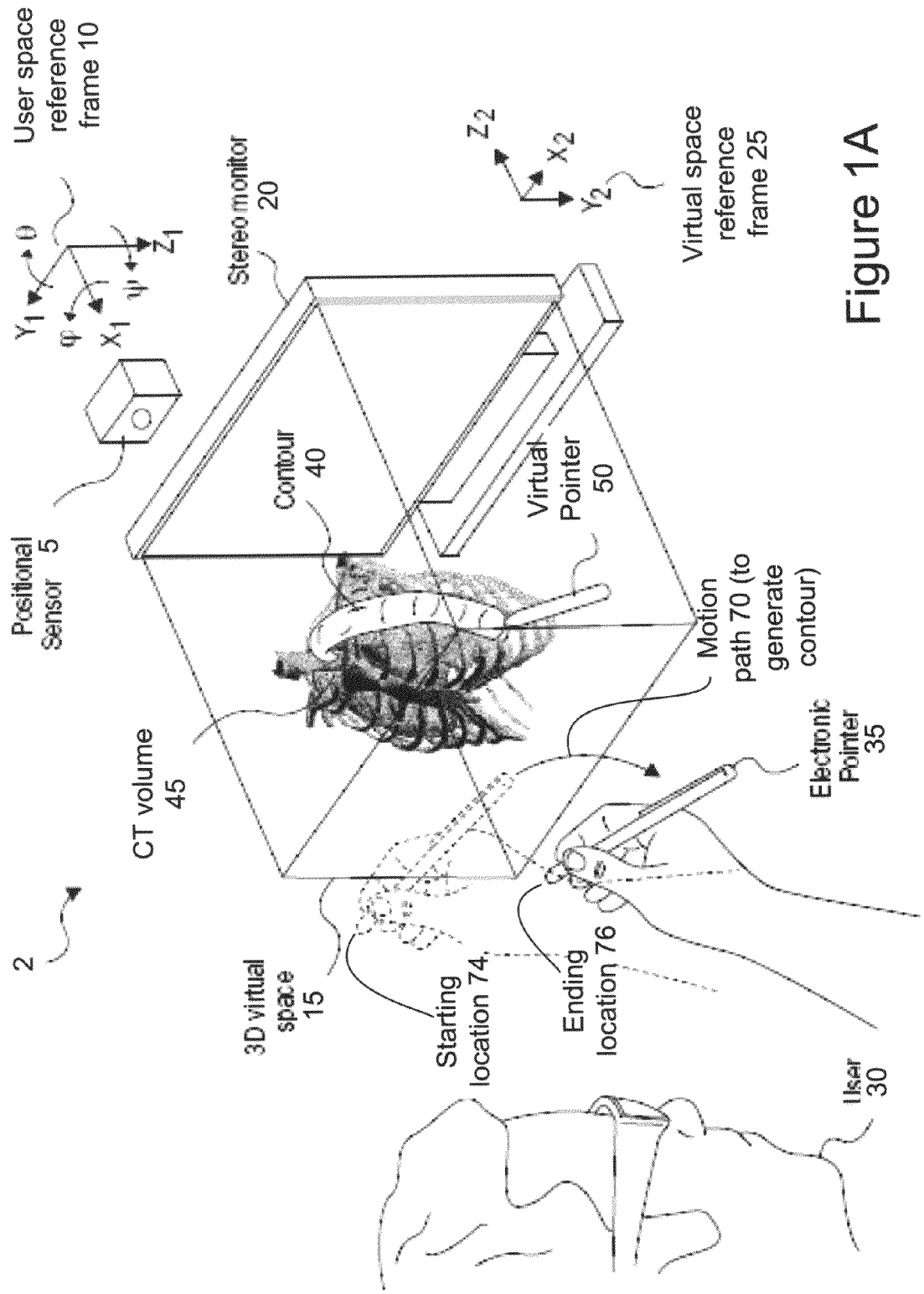
FIG. 1A illustrates an example user interaction with a virtual environment, in accordance with one embodiment of the present invention.

In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

The software, or computer program product, may include a machine-readable medium having stored thereon instructions, which may be used to program a computer system (or other electronic devices) to perform a process. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or other type of medium suitable for storing electronic instructions.

Embodiments of the present invention may also be practiced in distributed computing environments where the machine-readable medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

A method and apparatus for treatment planning are described, which may include a treatment planning system, treatment planning software, or a combination of a treatment planning system and treatment planning software. The treatment planning system may include components that enable the treatment planning software to present data to a user via a virtual environment.

Virtual Environment for Treatment Planning

A virtual environment (also known as an immersive environment, a virtual reality, or an immersive digital environment) is an artificial, computer-created three-dimensional (3D) virtual space in which a user interacts with virtual artifacts in a manner such that the user feels like he or she resides in the virtual space. The user can interact with virtual artifacts/objects within the virtual space using multi-dimensional inputs ranging from three-dimensional (3D) inputs (also known as three-degree-of-freedom inputs) to six-dimensional (6D) inputs (also known as six-degree-of-freedom inputs). One example of a virtual environment is a virtual reality simulation used by the military to train soldiers. A background introduction of virtual environments is provided by the article, "What Are Virtual Environments," by Stephen R. Ellis, published January 1994 in IEEE Computer Graphics & Applications.

The virtual environment includes one or more virtual artifacts. Each virtual artifact may represent a simulation of a real world object (e.g., of a patient anatomy), or may be a virtual object that has no real world counterpart. Virtual artifacts may represent isocenters, isocontours, volumes of interest, patient anatomies, and so on. Virtual artifacts that are simulations of real world objects may be based on measurement data such as diagnostic image data and treatment image data (e.g., CT image data, MR image data, PET image data, 3D rotational angiography image data, etc.).

Embodiments of the present invention provide a treatment planning system that interfaces with users via a computer-simulated virtual environment. In the context of treatment planning, the virtual environment includes one or more virtual artifacts that are 3D representations of a patient and/or of regions of a patient's anatomy. Target regions (e.g., tumor sites) and critical regions (e.g., anatomies sensitive to radiation) may also be defined in this virtual space (e.g., as virtual artifacts) with relation to the 3D patient image. The patient, target regions and critical regions may be represented by distinct virtual artifacts, or may be components of one or more virtual artifacts. A user can manipulate a 3D representation of the patient's anatomy, contour volumes of interest, fuse multiple images (e.g., virtual artifacts), and perform other treatment planning operations in an interactive manner as though the user was interacting with a real physical object. For example, using a data glove, the user may grip an image and move it over to another image to initiate image fusion. Alternatively, the user may, for example, grasp and manipulate a radiation dose isocenter. The virtual environment, when used in the radiation treatment planning system, can reduce the time a user spends in creating, viewing and manipulating treatment plans.

FIG. 1A illustrates an example user interaction with a virtual environment 2, in accordance with one embodiment of the present invention. The illustrated virtual environment 2 includes a 3D virtual space 15 that is rendered by a stereo monitor 20 in front of a user 30. Included in the 3D virtual space 15 is a computed tomography (CT) volume (a 3D computed tomography image) 45 of a skeletal torso. As shown, the user 30 can move an electronic pointer 35 (or other 3D, 4D, 5D or 6D input device) from a starting location 74 to an ending location 76 along a motion path 70 to generate a contour 40. As the user moves the electronic pointer 35 along the motion path 70, the motion of the electronic pointer 35 is tracked by a positional sensor 5, and the contour 40 is generated within the 3D virtual space 15 of the virtual environment 2. The virtual environment 2 enables the user to quickly and accurately create 3D contours within the 3D virtual space 15. Additionally, other treatment planning tasks and operations, such as image fusion, plan generation, etc. can be simplified, sped up and improved using a virtual environment.

System Architecture

Figure 1B:
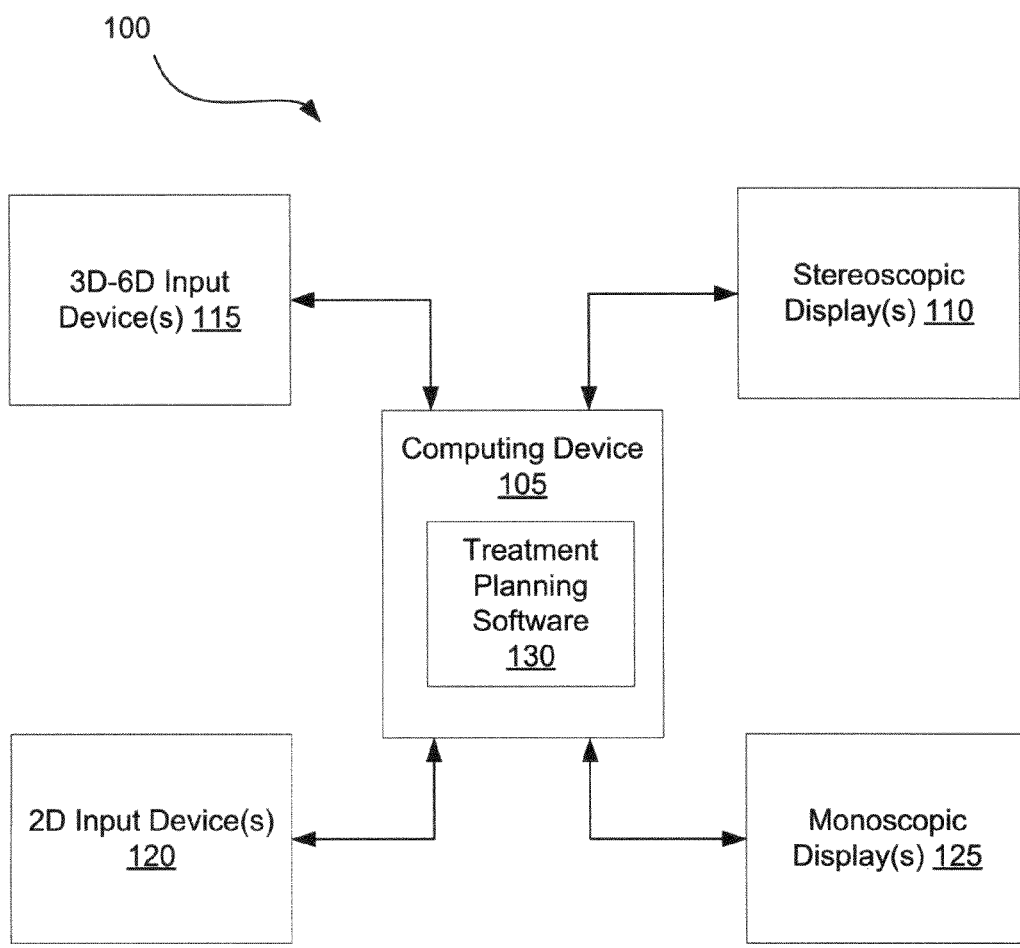
FIG. 1B illustrates a block diagram of a system architecture for a treatment planning system that provides a virtual environment with which users can interact, in accordance with one embodiment of the present invention.

FIG. 1B illustrates a block diagram of a system architecture for a treatment planning system 100 that provides a virtual environment with which users can interact. The treatment planning system 100 enables a user to perform treatment planning to efficiently and intuitively develop treatment plans for patients via a virtual environment. The treatment planning system 100 includes one or more stereoscopic displays 110 (or alternatively volumetric displays) and one or more 6D input devices 115 (or alternatively, 3D input devices, 4D input devices or 5D input devices) connected with a computing device 105. The treatment planning system 100 may also include one or more monoscopic displays 125 (e.g., standard CRT or LCD monitors) and/or one or more 2D input devices 120 (e.g., a standard mouse or touchpad).

The computing device 105 may be a special purpose computing device that includes one or more special purpose processing devices. Alternatively, the computing device may be a general purpose computing device (e.g., a desktop computer, server, mainframe, etc.) that includes one or more general purpose processing devices programmed to perform treatment planning tasks. The computing device includes memory and storage for storing treatment planning software, which includes instructions for performing treatment planning operations. The computing device may also include networking capability for networking with, for example, a treatment delivery system and/or an imaging system.

A stereoscopic display 110 is a display that uses stereoscopic photography, such as a stereo monitor or stereoscopic goggles. Stereoscopic photography consists of creating a 3D illusion by presenting a slightly different image to each eye. The 3D visual output of a stereoscopic display provides a user with improved depth perception, which may improve accuracy of contouring, image fusion, and other treatment planning operations.

Though the present application describes the use of stereoscopic displays, embodiments of the present invention may also incorporate other types of three dimensional displays. For example, rather than a stereoscopic display, in some embodiments a volumetric display may be used. A volumetric display is a graphical display device that forms a visual representation of an object in three physical dimensions, as opposed to the planar image of traditional screens that simulate depth. A volumetric display creates a 3D image by the emission, scattering or relaying of illumination from well defined regions in 3D space. The volumetric display may be a swept-volume display, a static volume display, an electro-holographic display, or a highly multi-view display. Accordingly, whenever a stereoscopic display is called out in embodiments of the present invention, it should be understood that other types of three dimensional displays such as volumetric displays may also be used. For simplicity, the term "stereoscopic display" is used throughout this application. However, in the context of this application, the term "stereoscopic display" should be taken to mean any display capable of displaying 3D images having depth. Similarly, it should be understood that a used herein, "stereoscopic virtual space" includes virtual spaces displayed by, for example, a volumetric display.

The stereoscopic display 110 may display both 3D stereoscopic images and 2D images/data. In one embodiment, the stereoscopic display 110 includes one or more 2D display regions (2D regions) in which 2D images/data are displayed. Such 2D images/data may include tables, charts, graphs, lists, 2D slices of 3D images, and so on.

Figure 2A:
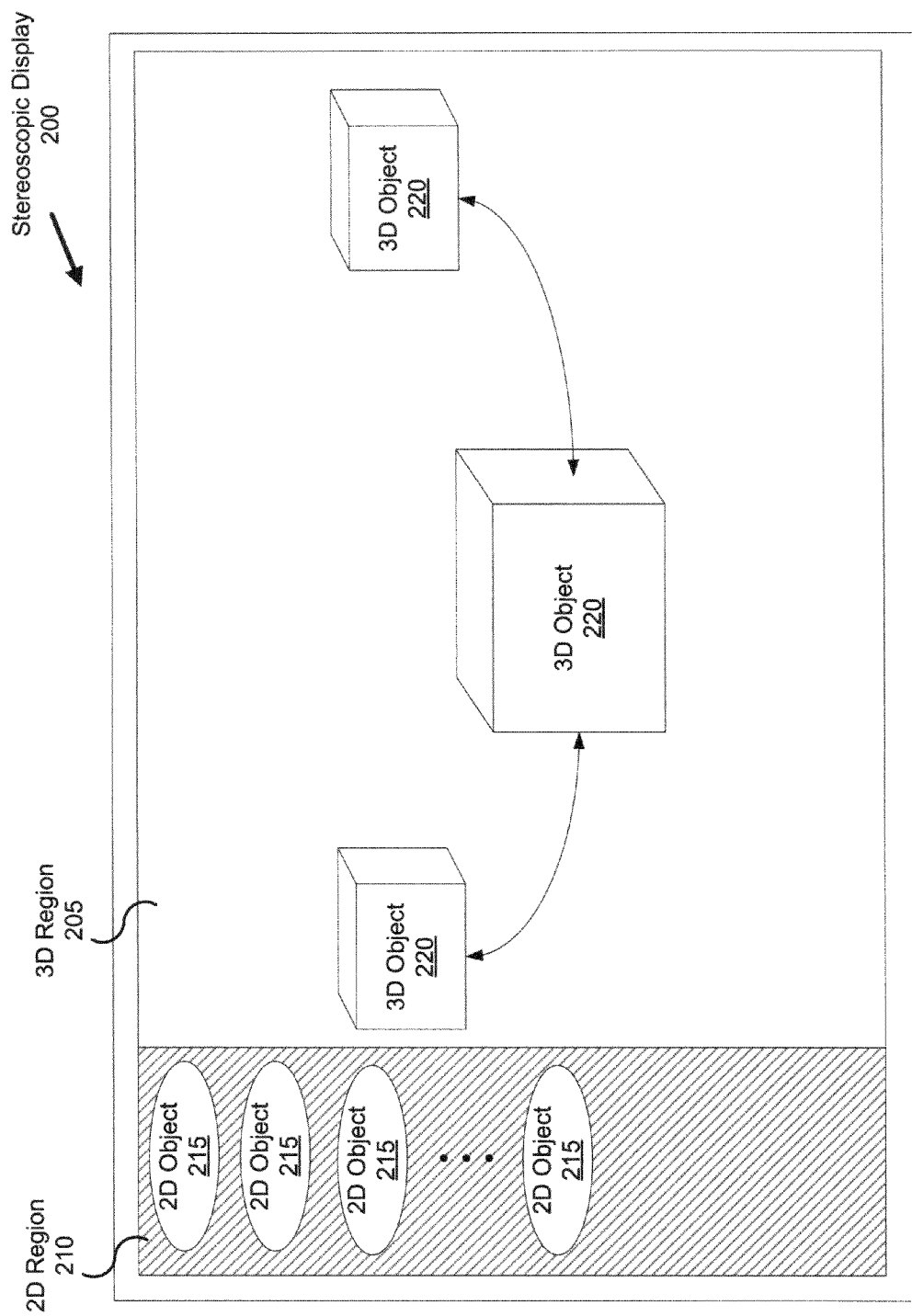
FIG. 2A illustrates a stereoscopic display that includes a 3D region for displaying 3D objects in stereo and a 2D region for displaying objects in 2D on a plane, in accordance with one embodiment of the present invention.

FIG. 2A illustrates a stereoscopic display 200 that includes a 3D region 205 for displaying 3D stereoscopic objects 220 and a 2D region 210 for displaying 2D images/data 215. The 2D region in one embodiment is displayed monoscopically. In one embodiment, the stereoscopic display 200 corresponds to stereoscopic display 110 of FIG. 1B. Images and data items that are not to be presented in three dimensions may be shown in the 2D region 210 of the stereoscopic display 200. For example, data tables, windows, input boxes, etc. may be shown in the 2D region 210. Additionally, the 2D region 210 may show 2D views (e.g., slices) of images shown in the 3D region 205.

As shown, the 2D region 210 may be a vertical band along a left hand side of the stereoscopic display 200. Data and objects displayed in the 2D region 210 may be shown two-dimensionally, while data and objects shown outside the 2D region 210 may be shown in virtual space (e.g., using stereography). In addition to, or instead of, the 2D region being a band along the left hand side of the stereoscopic display 200, the 2D region 210 may also include a vertical band along the right side of the stereoscopic display 200 and/or one or more horizontal bands along the top and bottom of the stereoscopic display 200. Alternatively, or in addition, the 2D region 210 may be a projection of images/data onto a two-dimensional surface of a 3D object. For example, the 2D region 210 may be included on a surface of a square or rectangle that is displayed by the stereoscopic display 200.

In one embodiment, the treatment planning system 100 may respond to a 6D input device in a different manner when a cursor is positioned in the 2D region 205 than when the cursor is positioned in the 3D region 210. For example, if the cursor is inside the 2D region, then a 2D mouse emulation mode may be used, which translates a 6D input (or a 5D input) into a 2D input. If the cursor is inside the 3D region, then a standard input mode may be used. The 2D mouse emulation mode is described in greater detail below with reference to FIG. 14.

Returning to FIG. 1B, in one embodiment, the treatment planning system 100 includes a conventional monoscopic display 125, such as a standard liquid crystal display (LCD) or cathode ray tube (CRT) monitor. Images and data items that do not benefit by a 3D stereoscopic presentation may be shown in the monoscopic display 125 (or in a 2D region of the stereographic display). For example, data tables, windows, input boxes, etc. may be shown in the monoscopic display 125. Additionally, the monoscopic display 125 may show 2D views (e.g., slices) of images shown in the stereoscopic display 110. The monoscopic display 125 can also display 3D images in a plane using orthographic projection. Thus, the same 3D images may be shown in both the stereoscopic display 110 and the monoscopic display 125. However, such 3D images displayed on the monoscopic display 125 lack depth and will not be displayed in virtual space.

The stereoscopic display 110 and/or the monoscopic display 125 may include display areas that include the display of medical images and other large graphical and text controls. A user interface layout may include virtual artifacts based on CT images, PET images, and/or combined CT/PET images. The CT/PET image may be generated using a fusion process to display the images in a common space, as described below. In one embodiment, the CT image, PET image or combined CT/PET image may also include a display of the beam paths that are generated according to a treatment plan.

The virtual artifacts (e.g., a combined CT/PET image including displayed beam paths) may be displayed by the stereoscopic display 110 and/or monoscopic display 125 using one or more 3D rendering techniques as known to one skilled in the art. In one embodiment, a combination of a volume rendering technique and an embedded VOI surface rendering technique are used to display one or more virtual artifacts. A volume rendering technique can be used to present not only surface characteristics of an object, but also internal structures of the object. Volume rendering can convert an object into small voxels in a 3D volume, and then assign each voxel with color and opacity information. The final rendering result is a 3D projection composition of the volume along a view direction. Any one of various volume rendering algorithms known in the art may be used. In one embodiment, for example, a 3D texture based direct volume rendering algorithm may be used.

A 3D volume dataset which varies over time may be considered to be a 4D deformable volume image. Examples of 3D volume data sets that may vary over time include datasets for the heart, ribcage, and lung. In one embodiment, a 4D rendering technique is used to render such a 4D deformable volume image. A number of methods may be used for volume rendering of 4D deformable volume images. These methods may involve, but are not limited to, one or more of the following approaches: representing a deformable volume using tetrahedrons that have freedom to move in 3D space; using a marching cube algorithm to convert volume rendering to surface rendering by finding small iso-surfaces in non-structural data; representing the volumetric dataset with a procedural mathematical function; using a multiple volume switching method, in which all the intermediate volumes are generated before rendering; etc.

A set of 3D images of a volume may be captured during different phases of deformation of an object within the volume. The set of 3D images may be used to determine how voxels within the volume migrate from their original locations to deformed coordinate locations during specific phases of the deformation.

In one embodiment, sub-phases are interpolated between consecutive phases. The sub-phases may be used to reduce jitter caused by time lapse between sequential phases, and increase quality and accuracy of the data set. In one embodiment, geometric based interpolation that uses voxels from future phases to interpolate voxels of an earlier in time sub-phase is used. In another embodiment, content based interpolation that uses voxels from an earlier in time phase to interpolate voxels in a future sub-phase is used. Alternatively, an interpolation between sequential phases may be determined for a sub-phase by taking a weighted average of transformation vectors at given deformation coordinate locations for the two consecutive phases. In another embodiment, deformation matrices are generated for transforming original voxels into deformed voxels during the different phases and/or sub-phases. The transformation vectors at a particular voxel coordinate may be retrieved from the deformation matrixes (or deformation volume textures generated from the deformation matrixes).

Multiple sub-phases may be interpolated between consecutive phases by adjusting a weighting factor, step(j), for each sub-phase interpolated. The weighting factor skews the interpolation bias in selected increments (e.g., for ten sub-phases, the weighting factor could be incremented from 0 to 1.0 in 0.1 increments for each sub-phase) from the earlier phase to the later phase of the two consecutive phases. 4D rendering is discussed in greater detail in U.S. patent application Ser. No. 11/144,247, entitled "Interpolating and Rendering Subphases of A 4D Dataset," which is incorporated by reference.

Though the preceding and following description often refers to a stereoscopic display, it should be understood that multiple stereoscopic displays (or volumetric displays, or combinations of stereoscopic displays and volumetric displays) may also be used. For example, in one embodiment, three 3D stereoscopic views (each of which may be considered to have a separate virtual space) are displayed concurrently. The three 3D stereoscopic views may each be shown in different regions of a single stereoscopic display (e.g., stereoscopic goggles or a single stereo monitor). Alternatively, each 3D stereoscopic view may be shown in a different stereoscopic display (e.g., on a different stereo monitor). The three 3D stereoscopic views may reflect three different orientations of the same image. During, for example, 3D manual fusion, when a user manipulates a source image volume, he can examine the alignment simultaneously in the three views. This can make manual fusion work more efficient, as described below.

FIGS. 2B-2D illustrate examples of three different possible display setups for the treatment planning system 100 of FIG. 1B, in accordance with embodiments of the present invention. In FIG. 2B, all data is displayed in a single stereo monitor 235. In one embodiment, the stereo monitor is manufactured by Pavonine Korea of Incheon, Korea. The data displayed on the stereo monitor 235 may include both 3D stereoscopic images/data and 2D images/data, which may be displayed monoscopically (e.g., as shown in FIG. 2A). The stereo monitor 235 may also display a single 3D scene in a virtual space or multiple 3D scenes in one or more virtual spaces (e.g., multiple 3D views of a virtual artifact representing a patient anatomy). In FIG. 2C, some information is displayed in a regular monoscopic monitor 240, while other information is displayed in a stereo monitor 245. The regular monitor 240 and the stereo monitor 245 may be positioned side by side as shown, or in other arrangements (e.g., with the regular monitor 240 on top of the stereo monitor 245). In one embodiment, 3D virtual artifacts (e.g., of a patient anatomy) are shown in the stereo monitor 245, while other information is shown in the regular monoscopic monitor 240. Alternatively, the stereo monitor 215 may display 2D data along with the 3D virtual artifacts (e.g., as shown in FIG. 2A). In FIG. 2D, a regular monoscopic monitor 250 is used in conjunction with stereoscopic goggles 255. In one embodiment, the stereoscopic goggles 255 are manufactured by Vuzix Corporation of Rochester, N.Y. Different views of the same data may be shown on the regular monitor 250 and the stereoscopic goggles 255. Alternatively, the stereoscopic goggles 255 and regular monoscopic monitor 250 may show different information. Other display setups may also be used.

In any of the display configurations shown in FIGS. 2B-2D, or in other display setups, a user may configure data to be displayed on each display device. For example, a user may choose to have a monoscopic display and a stereoscopic display show duplicates of the same information, where the information is presented in 2D or as an orthographic projection of a 3D image onto a plane on the regular monoscopic display and in a virtual space on the stereoscopic display. Alternatively, the user may specify that some data will be presented on the monoscopic display while other data will be presented in virtual space on the stereoscopic display. When a user provides input (e.g., via a 6D input device), the input may affect what is displayed on a single display or on multiple displays.

Returning to FIG. 1B, the 6D input devices 115 may include data gloves, an optical tracking device, an electromagnetic tracking device, a 6D mouse, a multi-touch screen device, and/or other devices capable of receiving data representing motions in six-degrees-of-freedom. The 6D input devices 115 can provide relative (delta) and/or absolute space position and orientation. Some 6D input devices 115 can provide force feedback (e.g., haptic feedback), and/or receive and identify gesture input. One or a combination of multiple 6D input devices 115 can be used in the treatment planning system 100. Moreover, one or more 6D input devices 115 may be used in combination with a standard 2D input device 125 such as a standard 2D mouse or touchpad.

Note that the present invention is not limited to 6D input devices. Embodiments of the present invention also work with 3D input devices, 4D input devices and 5D input devices. Wherever 6D input devices are called out in embodiments of the present invention, it should be understood that 3D input devices, 4D input devices and 5D input devices may also be used. For simplicity, the term "6D input device" is used in this application to describe multi-dimensional input devices that are used to interact with a virtual environment. However, in the context of this application, the term "6D input device" should be taken to mean any multi-dimensional input device having between three degrees-of-freedom and six degrees-of-freedom.

The 6D input devices 115 are used to manipulate virtual 3D stereo or volumetric images (e.g., virtual artifacts representing patient anatomies), or 3D renderings on a monoscopic display, in the treatment planning process. The system architecture integrates the 6D input devices 115 into the treatment planning system 100, and provides an interactive platform for manipulating image data in a virtual environment or a 3D rendering on a monoscopic display. How the treatment planning system 100 responds to input from the 6D input devices 115 in one embodiment is dependent upon an active application mode or application modes. For example, when a user uses a 6D mouse, there are multiple modes to interpret the 6D input information. When a first button is pressed, a subvolume visible clipping planes adjustment mode may be activated, which is described below with reference to the Plan Evaluation task. When the user then provides input from the 6D mouse, three visible clipping planes may be adjusted accordingly. When a second button is pressed, a 3D rotation mode may be activated. 6D input will then handle 3D volume rotation. There are numerous application modes that may be used with the 6D input tools, each of which may be associated with a treatment planning module or application. Application modes and treatment planning modules/applications are described in greater detail below in the Software Architecture section.

Each 6D input device 115 has different strengths and weaknesses, and may be used for different purposes. For example, a data glove can be used to grab and push volume of interest (VOI) structures, while a 6D mouse may be used for fine control of a virtual artifact's position and orientation. Ray tracing, cutting planes, and other operations for a specific virtual artifact (e.g., 3D image, volume of interest (VOI), etc.) can also be performed in the virtual space using the 6D input devices 115.

Figure 3A:
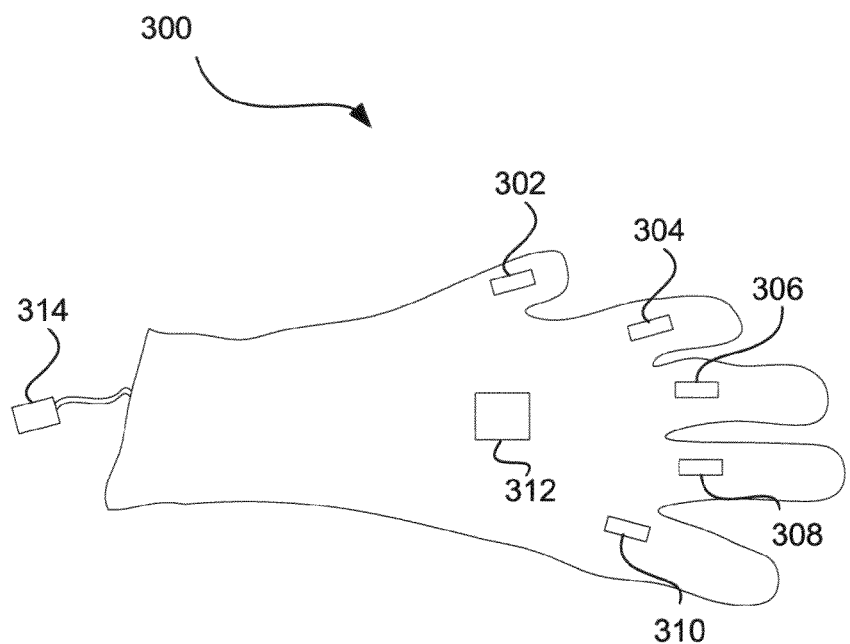
FIG. 3A illustrates a data glove 6D input device that may be used with the treatment planning system, in accordance with one embodiment of the present invention.

FIGS. 3A-6B illustrate examples of different 6D input devices that may be used with the treatment planning system 100 of FIG. 1B. Any of these 6D input devices may also be used as 3D, 4D or 5D input devices (e.g., by ignoring one or more degrees of freedom). FIG. 3A illustrates a data glove 300, in accordance with one embodiment of the present invention. In one embodiment, the data glove is manufactured by DGTech Engineering Solutions of Bazzano Italy. For the data glove 300, hand motion data is acquired that includes glove position and orientation (e.g., roll and pitch), as well as bend flexures of the fingers. Bend flexures may be detected, for example, using bending sensors 302-310, which are located proximate to finger joints of the glove. Position and orientation of the data glove 300 may be determined based on an inertial sensor 312, which may include an accelerometer (e.g., a 3-axis accelerometer) and/or a gyroscope. The position and/or orientation of the data glove 300 may also be tracked using a tracking system (in which the data glove is a tracked object of the tracking system), which is described below.

The treatment planning system 100 may interpret the combined hand gestures and/or hand orientations from the data glove 300 as commands and/or motion events. Examples of commands that may be interpreted from the glove include okay/proceed and cancel. Examples of motion events that may be interpreted from the glove include Pan (left/right/up/down), Zoom (in/out), and Rotate (roll/pitch/yaw). Each motion event caused by glove movement and/or gesture may be translated to a manipulation of virtual artifacts (e.g., representations of patient anatomies) in stereoscopic virtual space. For example, glove movement may cause a virtual scene including a virtual artifact representing a skull to be panned, zoomed in or out, rotated, etc.

Figure 3B:
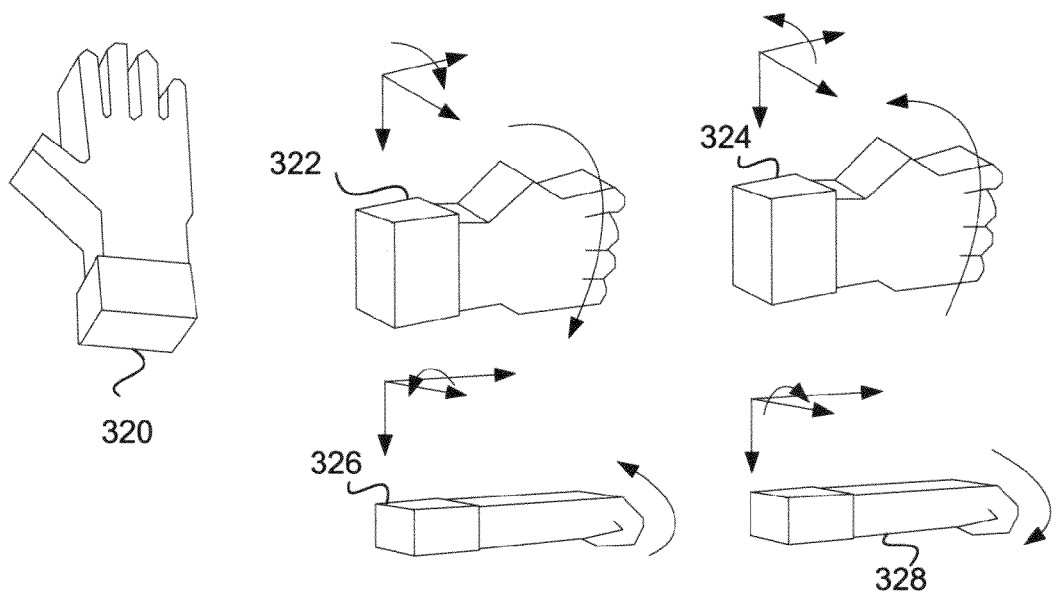
FIGS. 3B-3D illustrate example gesture commands for the data glove, in accordance with one embodiment of the present invention.
Figure 3C:
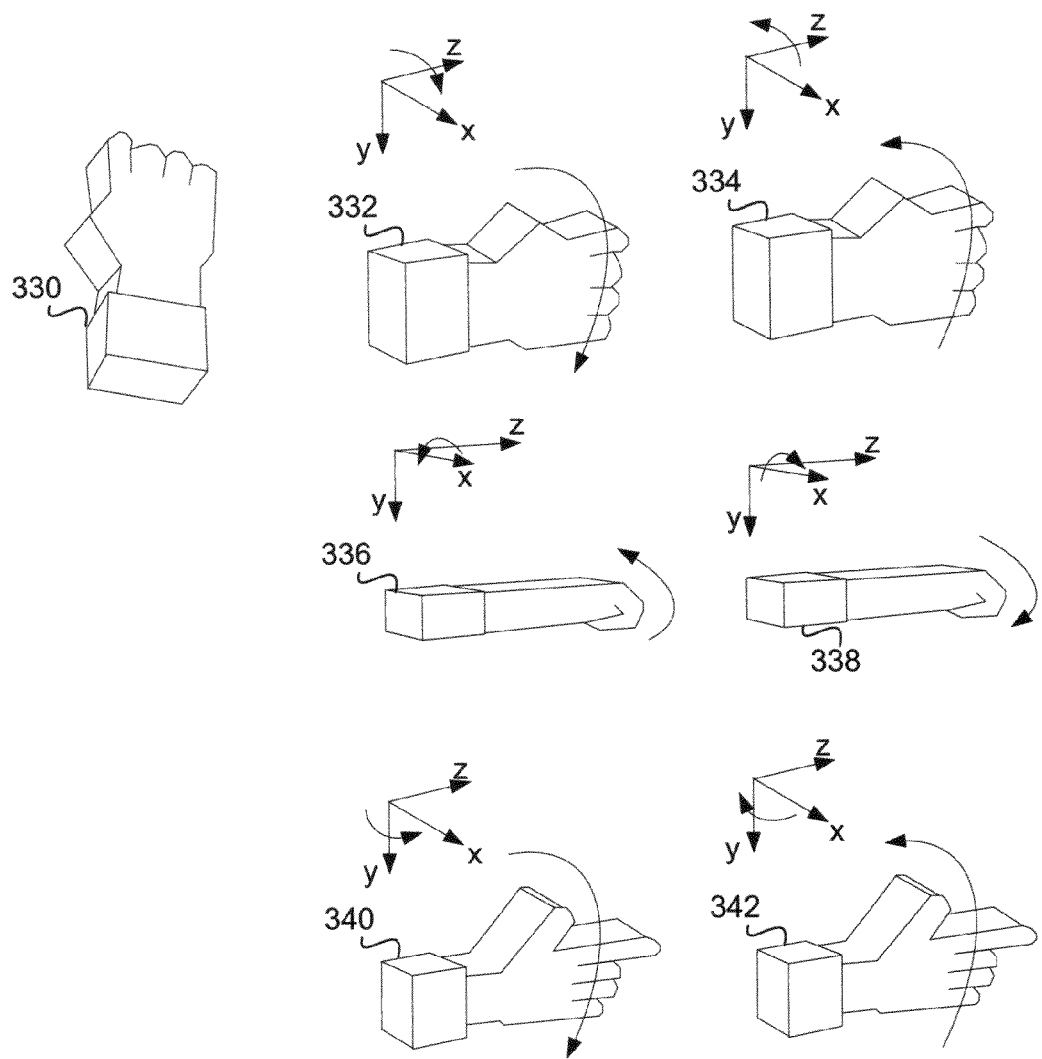
Figure 3D:
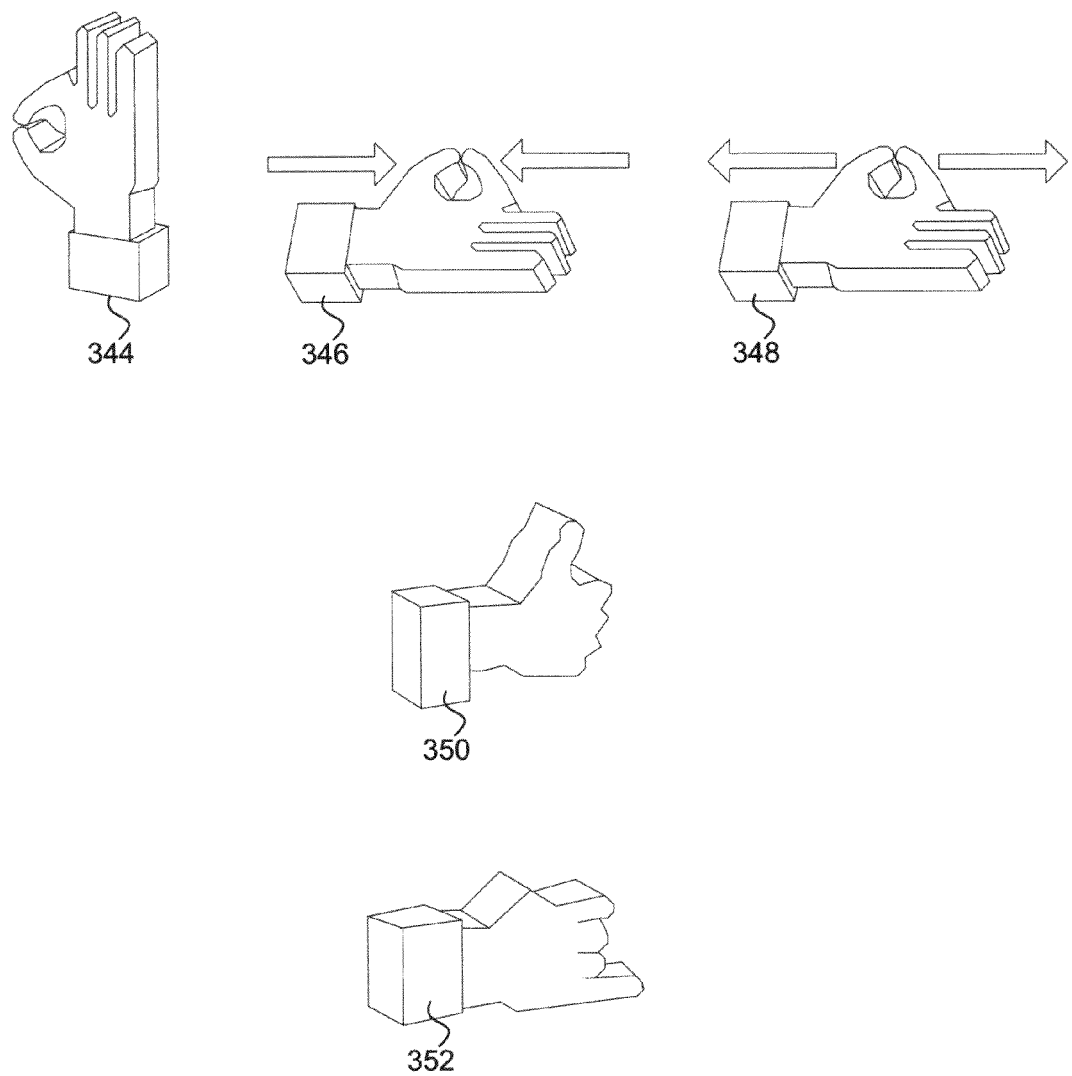

FIGS. 3B-3D illustrate multiple glove gestures that in one embodiment causes commands and/or motion events to be triggered. Referring to FIG. 3B, in one embodiment, an open forward facing hand gesture 320 generates a command to enter a pan mode. While the pan mode is active, various additional hand gestures may cause the virtual space to be panned in different directions. In one embodiment, forearm supination with a closed fist 322 causes a "pan right" motion event and forearm pronation with a closed fist 324 causes a "pan left" motion event. Additionally, wrist extension with a closed fist 326 causes a "pan up" motion event and wrist flexion with a closed fist 328 causes a "pan down" motion event in one embodiment.

Referring to FIG. 3C, in one embodiment a skyward pointed closed fist gesture 330 generates a command to enter a rotate mode. While the rotate mode is active, various hand gestures may cause the virtual space to be rotated about different axes. In one embodiment, forearm supination with a closed fist 332 and forearm pronation with a closed fist 334 cause "rotate about z-axis" motion events. Additionally, wrist extension with a closed fist 336 and wrist flexion with a closed fist 328 cause "rotate about x-axis" motion events. Forearm supination with a pointed index finger 340 and forearm pronation with a pointed index finger 342 may additionally cause "rotate about y-axis" motion events in one embodiment.

Referring to FIG. 3D, touching the thumb and index finger while the hand is pointed skyward initiates a zoom mode. While in the zoom mode, pressing the thumb and index finger together 346 causes a "zoom-in" motion event, and separating the thumb and index finger causes a "zoom-out" motion event. A thumb up gesture 350 causes an "okay/proceed" command to be generated, and a closed fist with extended pinky finger gesture 352 causes a "cancel" command to be generated. The gestures described with reference to FIGS. 3B-3D show just one example of hand gestures that may be used with the data glove. Any combination of hand position, hand orientation, and finger flexures may be assigned to particular motion events and/or commands.

Figure 4:
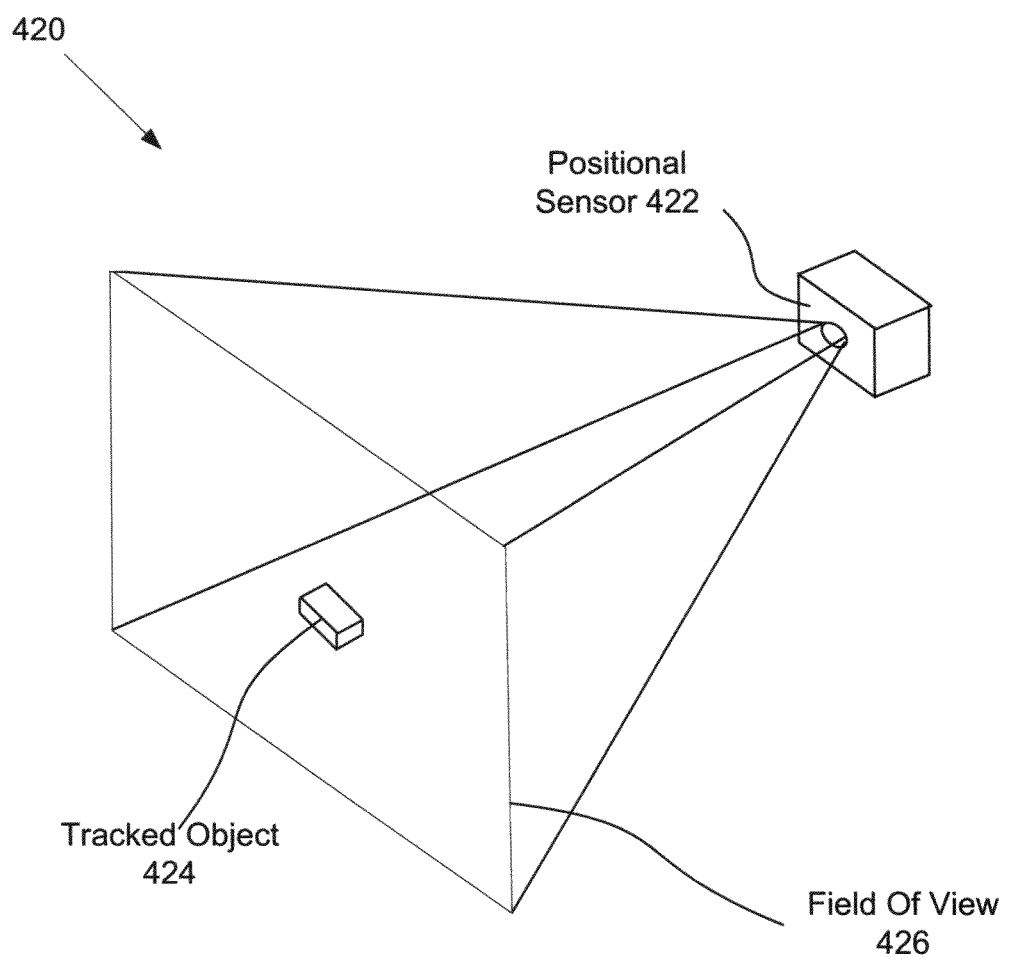
FIG. 4 illustrates a tracking system 6D input device that may be used with the treatment planning system, in accordance with one embodiment of the present invention.

FIG. 4 illustrates a six-degree-of-freedom tracking system 420, in accordance with one embodiment of the present invention. Note that a three-degree-of freedom to a five-degree-of-freedom tracking system may also be used. The tracking system 420 includes a positional sensor 422 and a tracked object 424. The positional sensor 422 may detect changes in position and orientation of the tracked object 424 as a user moves the tracked object within a field of view 426 of the positional sensor 422.

The positional sensor 422 may be a standard video camera, a Z-camera, a stereo camera, an infrared tracker or other optical sensor. The positional sensor 422 may also be an electromagnetic tracker. In one embodiment, the positional sensor 422 is an infrared tracker manufactured by Boulder Innovation Group, Inc. of Boulder, Colo. or an electromagnetic tracker manufactured by Polhemus of Colchester, Vt. Alternatively, the positional sensor 422 may be a sensor array such as an ultrasonic sensor array, a photonic detector, or some other positional sensor capable of identifying motion along three to six degrees of freedom. The positional sensor 422 may also include a combination of different tracking technologies. For example, the positional sensor 422 may include an electromagnetic sensor and an optical sensor (e.g., infrared camera).

The nature of the tracked object 424 may be dependent on the positional sensor 422 used. The tracked object 424 may be a powered electronic device, such as an electronic pointer, electronic pen, data glove, etc. If the positional sensor 422 is an optical positional sensor, such as a video camera, Z-camera, stereo camera, etc., then the object 424 may be a powered electronic device that includes one or more active light emitters (e.g., light emitting diodes (LEDs)) or passive light emitters to improve an ability of the positional sensor 422 to track the object 424. In another embodiment, the tracked object 424 is unpowered. For example, if the positional sensor 422 is an electromagnetic tracker, the tracked object 424 may be any object that includes passive sensor coils. Alternatively, the tracked object 424 may simply be a user's hand (e.g., if the positional sensor 422 is an optical tracker with image and/or hand gesture recognition.

Figure 5A:
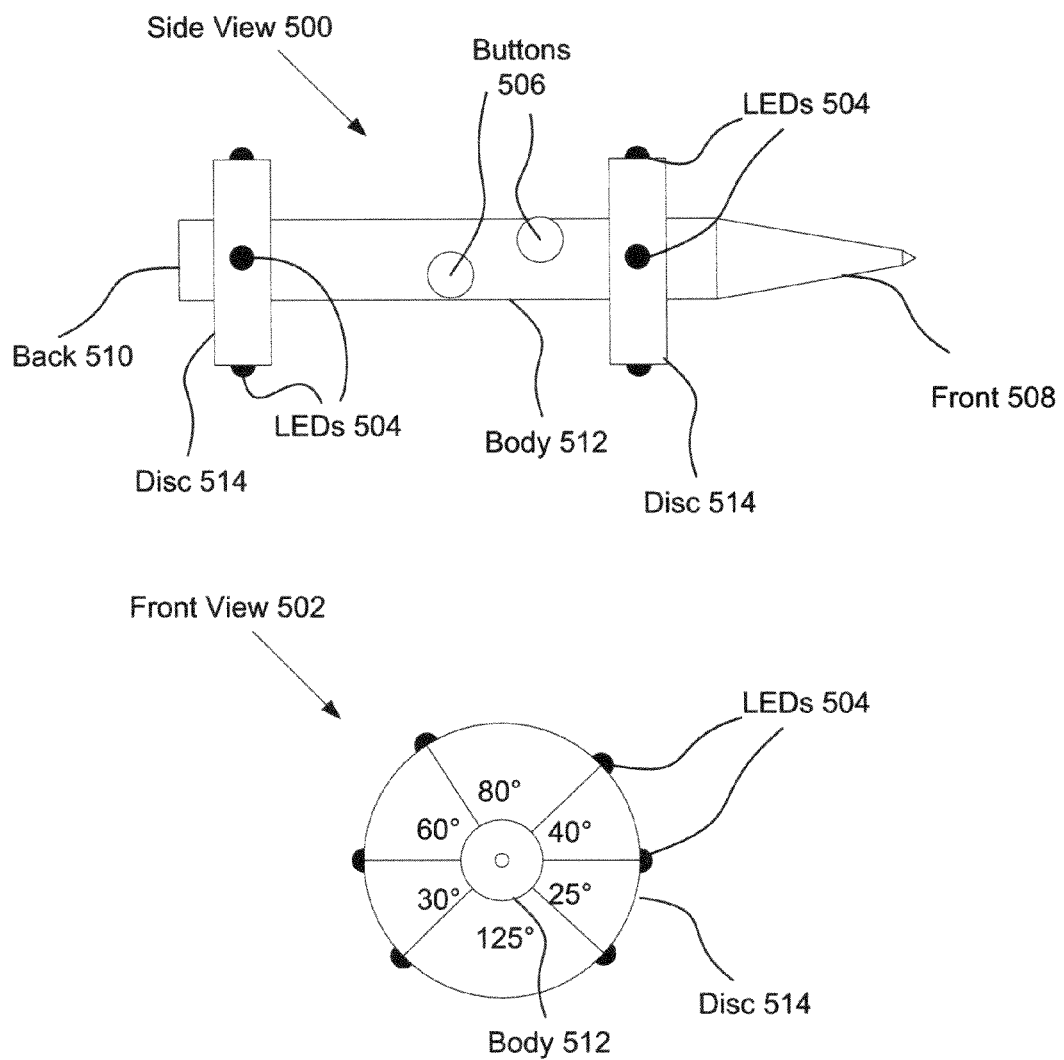
FIGS. 5A-5D illustrate examples of electronic pointers that may be used as tracked objects with the tracking system 6D input device of FIG. 4.
Figure 5B:
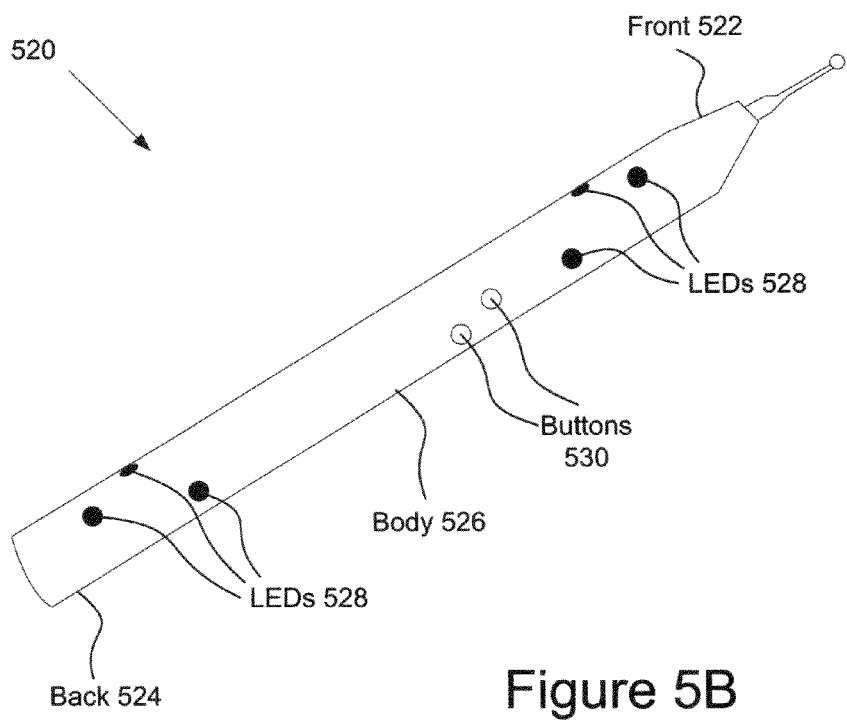
Figure 5C:
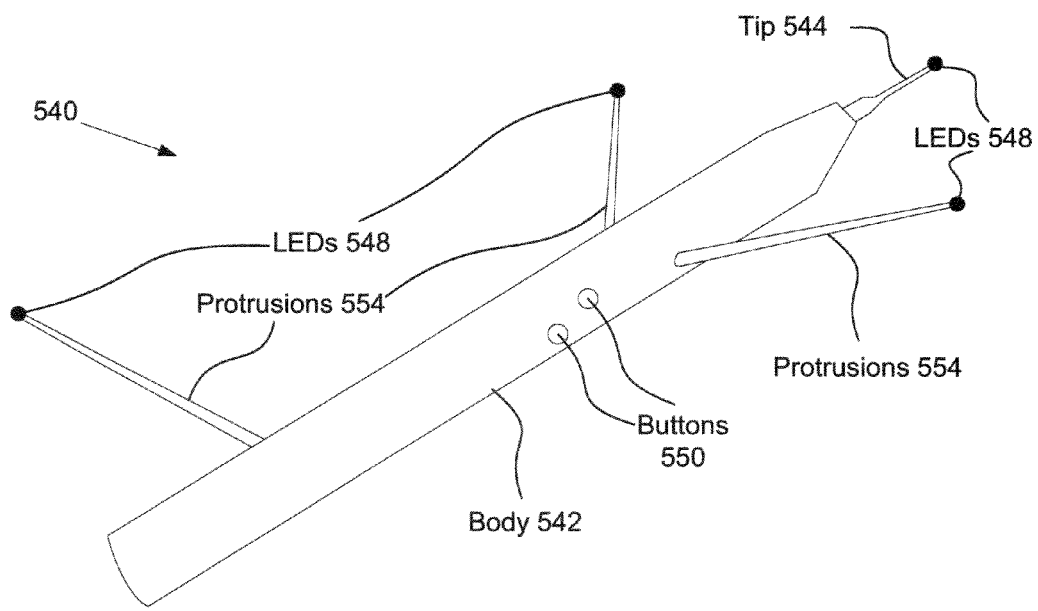

FIGS. 5A-5C illustrate example electronic pointers/pens that may be used as tracked objects 424 with the tracking system 420 of FIG. 4. In the examples depicted, the pointers include active light emitters and/or passive light emitters (e.g., passive optical spheres). Each of the electronic pointers also includes one or more buttons that enable the user to send control messages to the treatment planning system. For an electromagnetic tracking system, the electronic pointer may include active electromagnetic markers (e.g., transponders) and/or passive electromagnetic markers (e.g., passive sensor coils) rather than light emitters. The electronic pointer may also include inertial sensors such as an accelerometer and/or gyroscope for computing a position and orientation of the electronic pointer. The electronic pointer may be connected with a computing device via a wired connection (e.g., via universal serial bus (USB), firewire, ps/2, etc.) or a wireless connection (e.g., Bluetooth, Zigbee, radiofrequency (RF), etc.).

FIG. 5A illustrates a side view 500 and front view 502 of an electronic pointer for use with an optical tracking system, in accordance with one embodiment of the present invention. The electronic pointer includes a body 512 having a front 508 and back 510. Discs 514 are attached to the body 512 of the electronic pointer at the front 512 and back 510. Each disc 514 includes six LEDs 504 positioned radially about the circumference of the disc 514. In one embodiment, the LEDs 504 are positioned at asymmetric intervals about the disc 514. For example, two of the LEDs 504 are positioned 125 degrees apart, while two other LEDs are positions 25 degrees apart. Alternatively, more or fewer LEDs 504 may be positioned at other regular or irregular intervals about the disc 514. The LEDs 504 enable an orientation of the electronic pointer to be accurately tracked, regardless of how the electronic pointer is rotated or where in the field of view of a positional sensor the electronic pointer is positioned. Accurate position and orientation of the electronic pointer may be determined even when some of the LEDs are occluded by a user's hand or by the electronic pointer itself. The electronic pointer further includes two buttons 506 for issuing commands.

FIG. 5B illustrates another example of an electronic pointer 520 for use in an optical tracking system, in accordance with another embodiment of the present invention. The electronic pointer 520 includes six LEDs 528 and two buttons 530 attached to a body 526 of the electronic pointer 520. Three of the LEDs 528 are located at a front 522 of the body 526, while three LEDs 528 are located at a back 524 of the body 526. The LEDs 528 are positioned about the surface of the electronic pointer's body 526 such that a position and orientation of the electronic pointer 520 can be accurately determined regardless of the position and orientation of the electronic pointer. The LEDs 528 may also be positioned to minimize the chance of the LEDs being occluded by a user's hand. In this example, the electronic pointer further includes two buttons 530 for issuing commands, although more or fewer buttons may be used.

FIG. 5C illustrates yet another example of an electronic pointer 540 for use in an optical tracking system, in accordance with another embodiment of the present invention. The electronic pointer 540 includes multiple protrusions 554 projecting from a body 542 of the electronic pointer 540. At the end of each protrusion is an LED 548. An additional LED 548 is located at a tip 544 of the electronic pointer 540. By placing the LEDs 548 at the ends of the protrusions 554, the chances that the LEDs will be occluded are minimized and/or eliminated. Thus, fewer LEDs may be used to accurately track a position and orientation of the electronic pointer 540. The electronic pointer 540 further includes two buttons 550 for issuing commands.

Figure 5D:
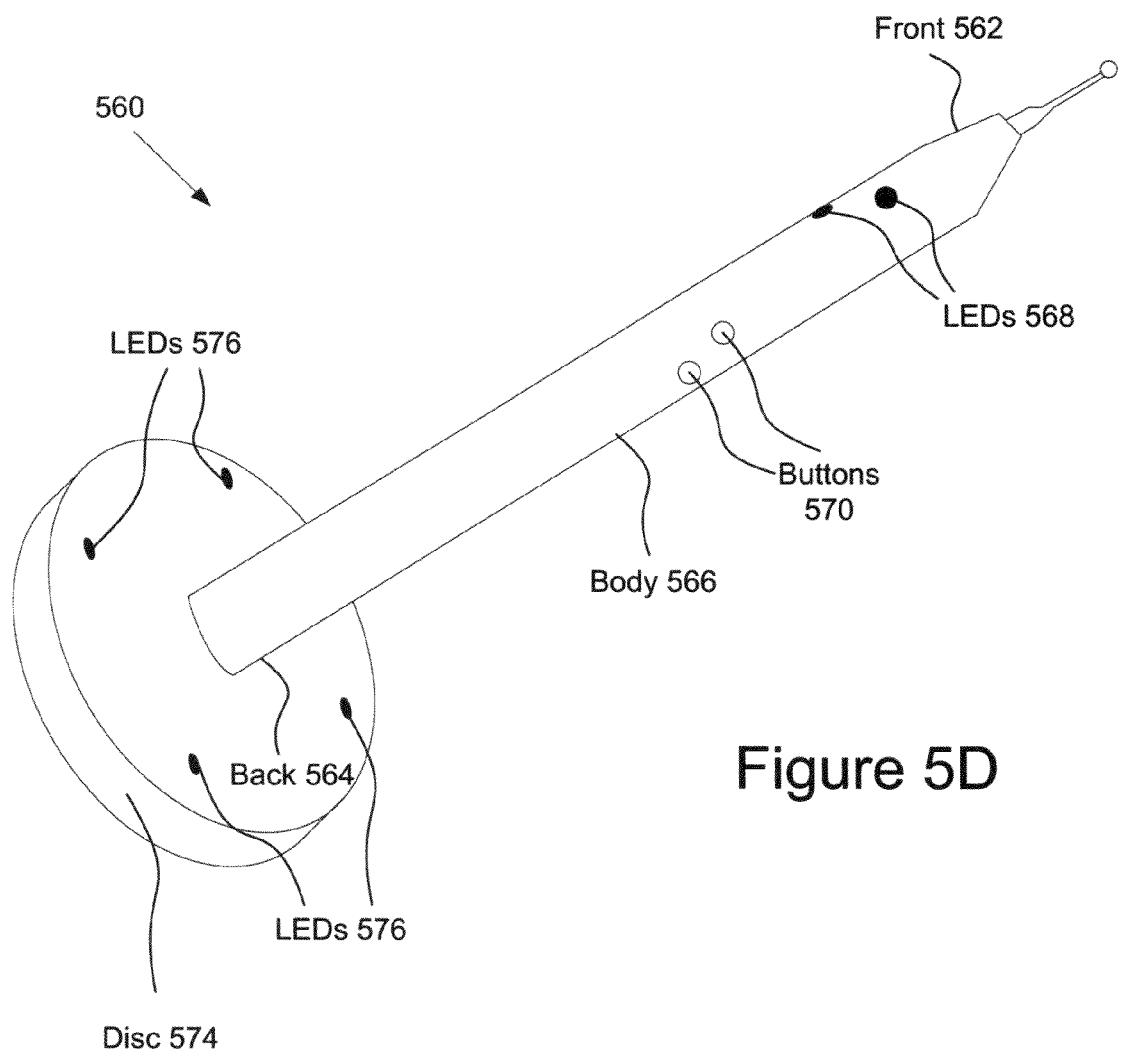

FIG. 5D illustrates yet another example of an electronic pointer 560 for use in an optical tracking system. The electronic pointer includes a body 566 having a front 562 and back 564. A disc 574 is attached with the body 568 at the back 564. The body 568 includes multiple LEDs 568 (e.g., two LEDs) at the front 562, and multiple additional LEDs 576 (e.g., four LEDs) on the disc 574. The electronic pointer 540 further includes two buttons 550 for issuing commands.

Figure 6A:
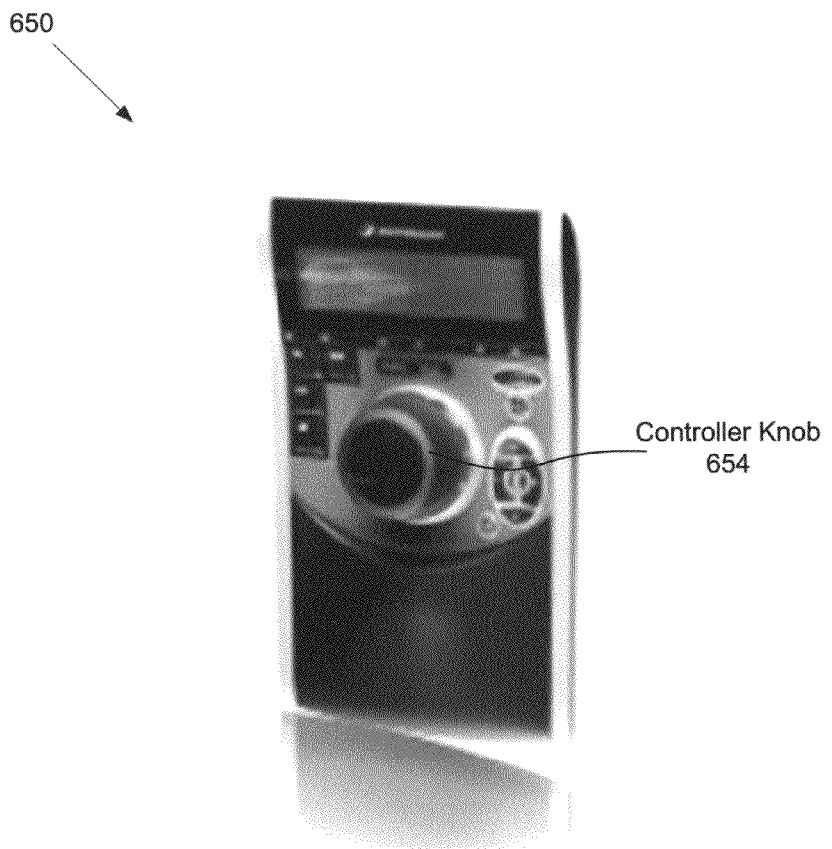
FIGS. 6A-6B illustrate a 6D mouse input device that may be used with the treatment planning system, in accordance with one embodiment of the present invention.
Figure 6B:
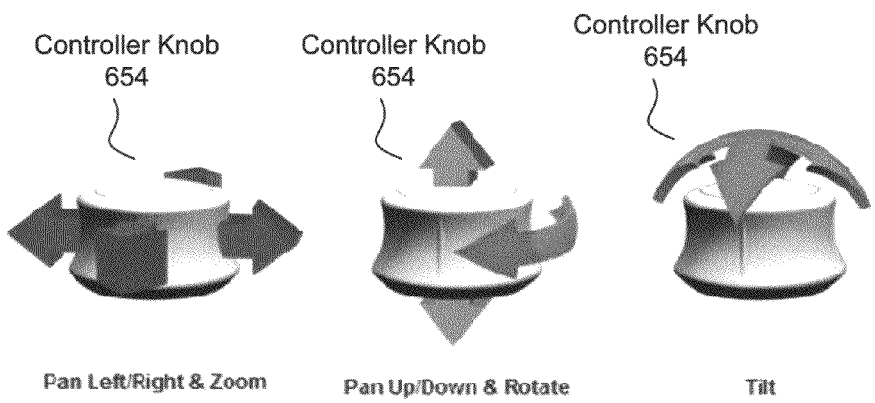

FIG. 6A illustrates a six-dimensional mouse 650, which in one embodiment is used as a 6D input device for the treatment planning system 100 of FIG. 1B. The illustrated 6D mouse 650 is 3Dconnexion's™ Space Pilot™. The 6D mouse 650 includes a 6D control knob 654 that may be tilted or twisted simultaneously to rotate and/or shift 3D imagery (e.g., virtual artifacts representing patient anatomy). The input from the 6D mouse 650 may provide 3D manipulation information that may be used, for example, to change a position, orientation and/or scale of the virtual space, change cutting plane parameters, etc. during treatment planning. With the 6D mouse 650 a user could rotate, tilt, and otherwise manipulate the control knob 654 to simultaneously zoom, pan left/right and up/down and rotate a displayed image. FIG. 6B illustrates how manipulations of the controller knob are translated into pan, rotate, tilt and zoom motion inputs.

Some 6D input devices are capable of providing force feedback (otherwise known as haptics). Haptic technology interfaces allow the virtual environment to provide feedback to the user via the sense of touch by applying forces, vibrations and/or motions to the user. Haptic technology can improve an interaction with virtual objects in the virtual environment by providing a sense of touch to an otherwise visual and/or audio experience. Haptic feedback may be provided based on, for example, intensity and/or density values of the CT image. As a pointer passes through regions of materials having higher intensity/density values, larger forces may be used. Additionally, when a user moves a cursor onto a VOI, haptic feedback may be used to inform the user that he has encountered (e.g., touched) the VOI. This may help a user delineate and/or navigate between different regions of a patient anatomy that are displayed in the virtual environment. Haptic feedback may also be provided based on dose density of an isocenter or isodose contour, based on active use of a bumper tool (e.g., to indicate that a surface has been bumped), etc. This will give the user additional sensory information.

Figure 7:
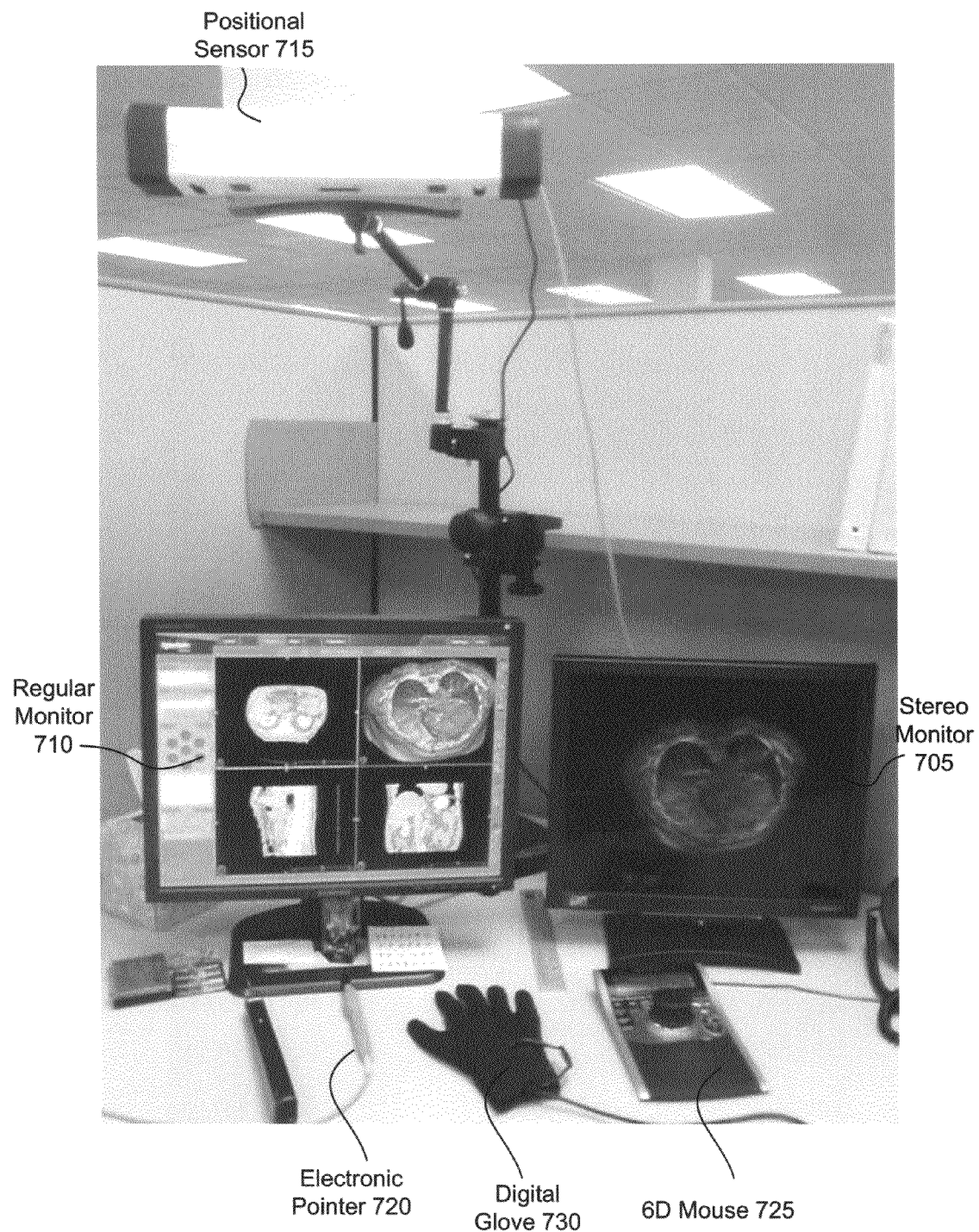
FIG. 7 illustrates an example setup for a treatment planning system, in accordance with one embodiment of the present invention.

FIG. 7 illustrates an example setup for treatment planning system 100, in accordance with one embodiment of the present invention. The example setup includes a stereo monitor 705, a regular monoscopic monitor 710, a tracking system including a positional sensor 715 and electronic pointer 720, a 6D mouse 725, and a data glove 730. As shown, the stereo monitor 705 is displaying a 3D virtual view of a patient anatomy in a 3D virtual space, and the regular monitor 710 is showing a monoscopic version of the same 3D view as well as multiple 2D slice views of the patient anatomy. Multiple 6D input devices (e.g., the data glove 730, 6D mouse 725 and tracking system) are provided to give a user numerous options for manipulating the representations of the patient anatomy and performing treatment planning operations in the virtual environment.

Virtual Environment Calibration and Registration

The terms user space, virtual space and CT space are used throughout this document. As used herein, user space refers to the physical space in which a user moves. This space is tracked using the tracking system described previously, and therefore may also be referred to as a tracking system space. The user space has a frame of reference (coordinate system) that corresponds to a reference frame of the tracking system (e.g., of a positional sensor of the tracking system).

The term virtual space refers to the 3D stereoscopic or virtual space in which images are rendered. The system may include a separate virtual space for each stereoscopic display. Each virtual space has its own reference frame. For a stereoscopic monitor, the virtual space reference frame (coordinate system) is fixed relative to the monitor, with the x-axis and y-axis corresponding to the horizontal and vertical dimensions of the screen, and the z-axis being orthogonal to the screen. Note that monoscopic monitors also include a workspace that is referred to herein as a standard workspace. This standard workspace has a workspace reference frame (coordinate system) that is also fixed relative to the monoscopic monitor, with the x-axis and y-axis corresponding to the horizontal and vertical dimensions of the screen, and the z-axis being orthogonal to the screen. The term monitor space may be used generically to refer to both the virtual space of the stereoscopic display and the standard workspace (standard space) of the monoscopic display.

CT space refers to the reference frame that was used to generate a CT image or CT images. Since treatment is typically performed relative to the CT reference frame, all treatment planning operations may be performed with reference to the CT space.

In order for a user to accurately and precisely interact with the virtual environment, some 6D input devices may need to be calibrated and/or registered with the virtual environment. The 6D input devices may also need to be calibrated and/or registered with the standard workspace of any monoscopic displays that are being used. Additionally, a CT space of a CT image/scan needs to be calibrated with the virtual space(s) of the virtual environment.

In one embodiment, some 6D input devices are calibrated/registered at the beginning of a treatment planning session. Alternatively, calibration and/or registration of the 6D input devices may be performed only when one or more parameters such as a user space changes (e.g., when the position of a tracking device or one or more monitors changes). Some 6D input devices, such as a 6D mouse, may not require any calibration. Other 6D input devices or 6D input systems, such as a tracking system (e.g., an optical tracking system or an electromagnetic tracking system) should be calibrated at least occasionally. Calibrating the 6D input devices ensures that the device's motions (or a user's motions) will be correctly translated into rotations and translations in the virtual environment. Calibration of a 6D input device may include calibrating a user space of the 6D input device to a virtual space (or virtual spaces) of the virtual environment and/or to a standard workspace of a monoscopic display, which is described in detail below with reference to FIGS. 8-9.

Many 6D input devices have sub-millimeter accuracy. However, at this level of sensitivity, a user will typically perform involuntary movements. To address this problem, one initial parameter that may be set for a 6D input device is a movement sensitivity. The movement sensitivity is a sensitivity to changes in position and/or orientation for the 6D input devices. The movement sensitivity may be defined by setting a minimum motion (motion threshold) that is required to cause a motion input to be recognized. If the detected movement is not at or above the threshold, then no movement may be recorded, or represented in the virtual environment. This can reduce or eliminate jitter caused by a shaky hand of a user. Thus, the movement sensitivity setting may cut down on or eliminate errors resulting from involuntary user motions.

In one embodiment, the movement sensitivity is divided into a positional sensitivity and a rotational sensitivity. Separate thresholds may be set for changes in position and for changes in orientation. Such settings may be selected separately for each 6D input device, or a single setting may be used for multiple 6D input devices. In one embodiment, the movement sensitivity for the 6D input device's motion is set in the CT space (e.g., 0.5 mm or 0.5 deg of a CT image), and is independent of the virtual space. However, scale factors may be used for transformation among the virtual space, the user space and the CT space.

In one embodiment, the movement sensitivity settings act as a filter, which simply filters out motions that fall below the thresholds. Alternatively, the movement sensitivity settings may be used to average or otherwise combine multiple readings to determine whether a user input should correspond to a change in position or orientation in the virtual space or the CT space. For example, and not by way of limitation, movement values from a preceding 10 samples, a previous 30 seconds, etc. may be averaged to determine whether the movement thresholds have been satisfied. The average may be a weighted average or a simple average. Other sensor reading combinations may also be used.

The position and orientation tracking mechanisms for each type of 6D input device may differ. Accordingly, each type of 6D input device may be calibrated in a different manner. Calibration of a wired glove may be performed through an interactive process. In one embodiment, this process includes having a user grasp his/her hand into a fist when wearing the glove. This may calibrate finger flexure thresholds for the user. Flexure of one or more fingers while wearing the glove may then trigger different commands or actions. Calibration of the glove may also include calibrating a location in the user space to correspond to an origin of the virtual space(s) of the virtual environment (and possibly any standard workspaces) and/or otherwise calibrating a reference frame of the data glove to a reference frame of the virtual space(s) (and standard workspaces). This may be performed by placing the glove at a certain location, and issuing a calibrate command. That location may then be calibrated to the origin in the virtual space(s) of the virtual environment and/or to the origin in a standard workspace. In one embodiment, the location at which the user first grasps his hands using the gloves is calibrated to the origin(s).

Figure 8:
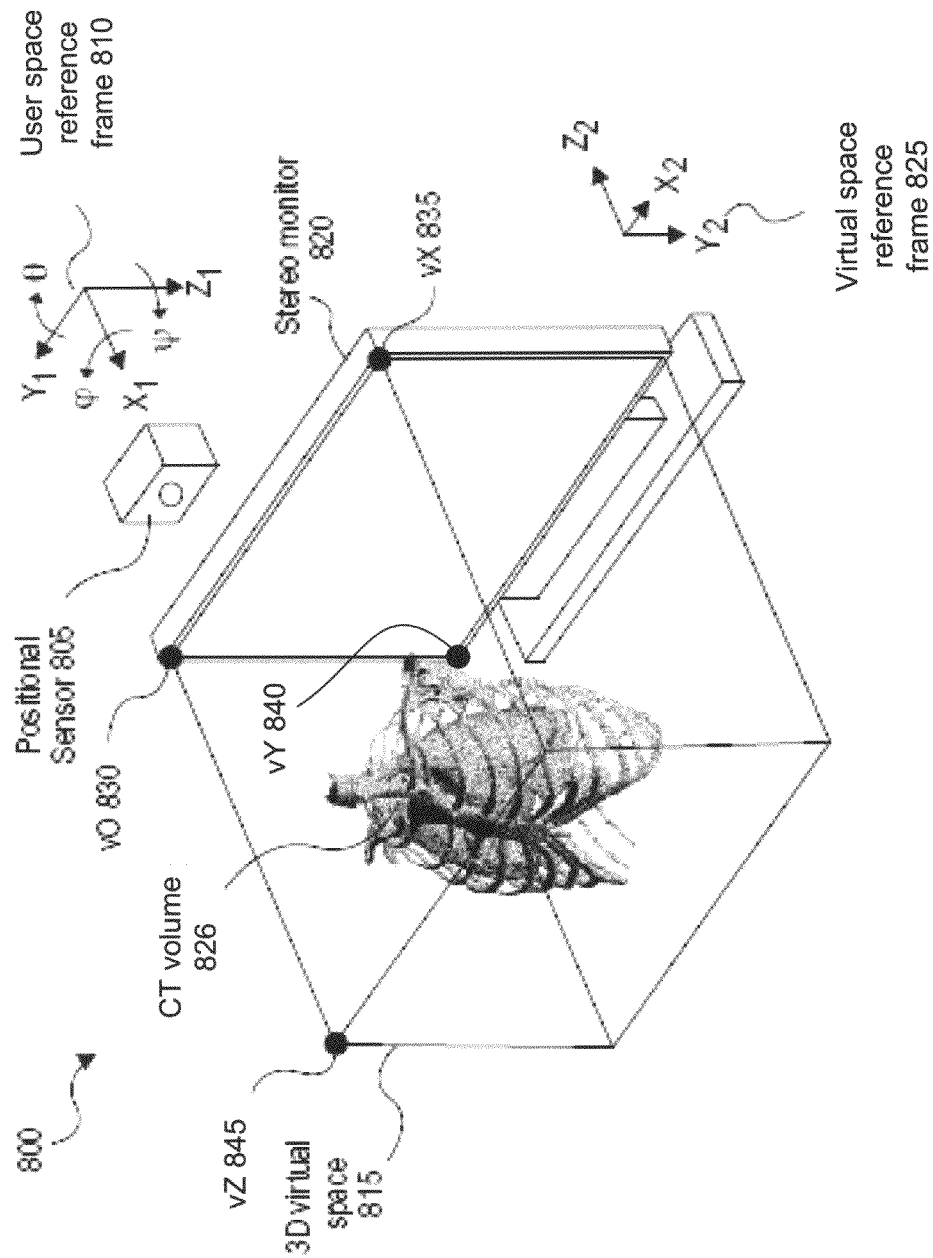
FIG. 8 illustrates a plan view of a virtual environment based on a tracking system and a single stereo monitor.

Calibrating the tracking system may include registering a frame of reference of the tracking system (user space) with a frame of reference of the virtual environment (virtual space) as represented by a stereoscopic display. FIG. 8 illustrates a plan view of a virtual environment 800 based on a tracking system and a single stereo monitor. In FIG. 8, the tracking system has a frame of reference 810 that is aligned with a positional sensor 805 of the tracking system. The virtual environment includes a 3D virtual space 815 that is provided by a stereo monitor 820. The 3D stereoscopic virtual space 815 (and correspondingly the virtual environment) has a frame of reference 825 that is aligned with the stereo monitor 820. The virtual space's frame of reference 825 has a z-axis normal to a screen of the stereo monitor 820. In order for a user's input that is based on a tracked object to accurately translate into motion input for the virtual environment, a relationship between the tracking system's (user space) reference frame and the virtual space reference frame needs to be determined. Such determination includes determining translations and rotations that, when performed on one of the frames of reference, will cause that frame of reference to become aligned with the other frame of reference. In one embodiment, registering the reference frames also includes determining a common origin. Once these frames of reference are registered with one another, a user may move the electronic pointer (or other 6D input device) in the user space in front of the user to cause a digital pointer in the computer-simulated virtual environment (virtual space) to make a corresponding move.

Figure 9:
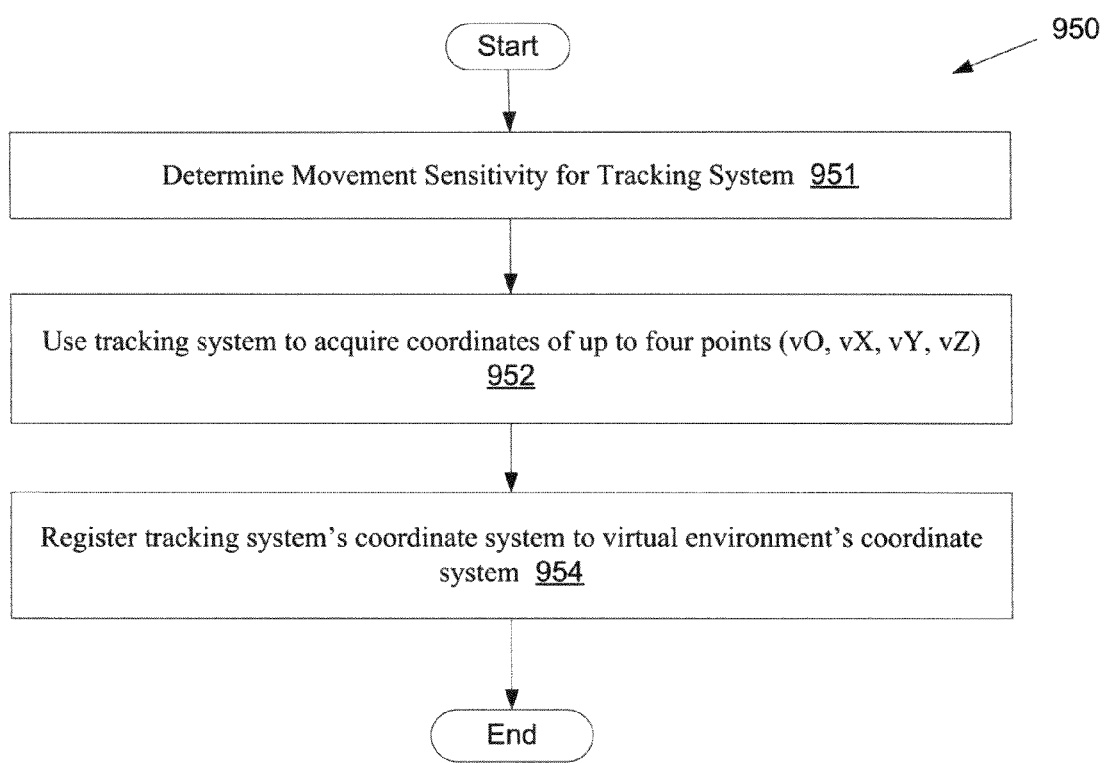
FIG. 9 illustrates a flow diagram of one embodiment for a method of calibrating the stereoscopic virtual space of a virtual environment with a user space of a tracking system, in accordance with one embodiment of the present invention.

One embodiment of registering the virtual space of the virtual environment displayed in a stereoscopic display with a tracking system is described with reference to FIGS. 8-9. FIG. 9 illustrates a flow diagram of one embodiment for a method 950 of registering the virtual space of a virtual environment with a user space of a tracking system. The method is performed by processing logic that comprises hardware (e.g., circuitry, dedicated logic, programmable logic, microcode, etc.), software (such as instructions run on a processing device), or a combination thereof. In one embodiment, method 950 is performed by the computing device 105 of FIG. 1B.

Referring to FIG. 9, at block 951 of method 950 a movement sensitivity for the tracking system is determined. At block 952, as a tracked object (e.g., an electronic pointer) is positioned at multiple different locations, the position sensor of a tracking system acquires coordinates for each of the points and reports the coordinates to a computing device. This may identify the relationship between the virtual space frame of reference (coordinate system) and the tracking system's (user space) frame of reference. In one embodiment, a command to record the coordinates is issued by the user at each of the locations. The command may be issued, for example, by pressing a button on an electronic pointer, flexing a joint of a data glove, etc.

In one embodiment, the electronic pointer is placed at four different locations that correspond to an origin (vO), a point along an x-axis (vX), a point along a y-axis (vY) and a point along a z-axis (vZ), respectively. The vector from vO to vX may represent the x-axis, the vector from vO to vY may represent the y-axis, and the vector from vO to vZ may represent the z-axis (which may be perpendicular to the imaging plane of the stereo monitor). In another embodiment, the electronic pointer is placed at three different locations that correspond to the origin (vO), the point along the x-axis (vX), the point along the y-axis (vY), respectively. When three points are used, depth is automatically set based on an x-axis and y-axis scaling (depth is set proportionate to the x-axis and y-axis). The three points may be used if fixed scaling between the x-axis, y-axis and z-axis is acceptable. If the z-axis will be scaled differently than the x-axis or y-axis, then the fourth point should also be acquired.

In one embodiment, as shown in FIG. 8, three of the points (vO 830, vX 835 and vY 840) are three corners of a stereo monitor 820 (e.g., the upper left corner, upper right corner and lower left corner). Additionally, one of the points (vZ 845) may be at a location between a user and the stereo monitor 820 (for instance on a keyboard). In one embodiment, in which the vO 830, vX 835 and vY 840 points are at three corners of the stereo monitor 820, the coordinates of the points are used to identify the coordinate system of the virtual space presented by the stereo monitor 820.

The stereo monitor generates a magnetic field. In some instances (e.g., when a magnetic tracking system is used) this magnetic field may cause interference that makes detection of the electronic pointer difficult when the electronic pointer is positioned near the monitor (e.g., when the points vO 830, vX 835 and vY 840 are three corners of the stereo monitor). Accordingly, in one embodiment each of these three points is at a known distance in front of one of the three corners of the stereo monitor. For example, a carpenter's square with a known length may be successively placed at each corner, and the acquire coordinates command may be issued while the electronic pointer is placed at the end of the square.

Referring back to FIG. 9, the computing device in one embodiment calculates vectors in the user space coordinate system for the vector between vO and vX, the vector between vO and vY and the vector between vO and vZ. Each vector may have an x, y and z component in the tracking system coordinate system. The computing system may identify each vector as an axis in the virtual space coordinate system of the virtual environment presented by the stereoscopic display. Therefore, this information identifies the relationships between the reference frames.

At block 954, the computing device registers the tracking system's coordinate system to the coordinate system of the virtual space (e.g., as displayed on the stereo monitor) using the data gathered at block 952. In one embodiment, the calibration includes determining translations and rotations that, when performed on one of the coordinate systems, would cause that coordinate system to become aligned with the other coordinate system.

The calibration of the tracking system to the virtual space of the stereo monitor can be represented by a 4×4 transformation matrix, as follows.

$$M_1 = \begin{bmatrix} R_{11} & R_{12} & R_{13} & T_x \\ R_{21} & R_{22} & R_{23} & T_y \\ R_{31} & R_{32} & R_{33} & T_z \\ 0 & 0 & 0 & 1 \end{bmatrix} \quad \text{(equation 1)}$$

Where $R_{11}$-$R_{33}$ represent values that define rotations about the x, y and z axis that would cause each axis of the user space to be parallel to an axis of the virtual space represented in the monitor, and where $T_x$-$T_z$ represent values that define translations that would cause the origin of the user space to be at the same location as the origin of the virtual space. Each of the rotation and translation values may be computed from the coordinates acquired at block 952.

Once the matrix $M_1$ is computed, any position measured in the user space $(X_u, Y_u, Z_u)$ can be transformed into a position in the virtual space $(X_v, Y_v, Z_v)$ by multiplying a vector from the origin to the measured coordinates in the user space coordinate system by the transformation matrix $M_1$, as follows:

$$\begin{bmatrix} X_v \\ Y_v \\ Z_v \\ 1 \end{bmatrix} = M_1 \begin{bmatrix} X_u \\ Y_u \\ Z_u \\ 1 \end{bmatrix} \quad \text{(equation 2)}$$

Rather than matrices, other transformation representations may also be used. For example, quaternion mathematics may be used to represent the transformations. The calibration process described in method 950 provides for an accurate, easy and fast 3D virtual space registration for a 6D input device when a single stereoscopic display is used.

When the treatment planning system uses multiple visual output devices (e.g., one stereoscopic display and one monoscopic display), each visual output device (display) may have its own reference frame. For example, the virtual environment may include a virtual space with its own coordinate system for a stereoscopic display, and a standard workspace may include its own separate coordinate system for a monoscopic display. Therefore, in one embodiment, the tracking system is registered with the frames of reference of each display (e.g., of each monitor).

Figure 10:
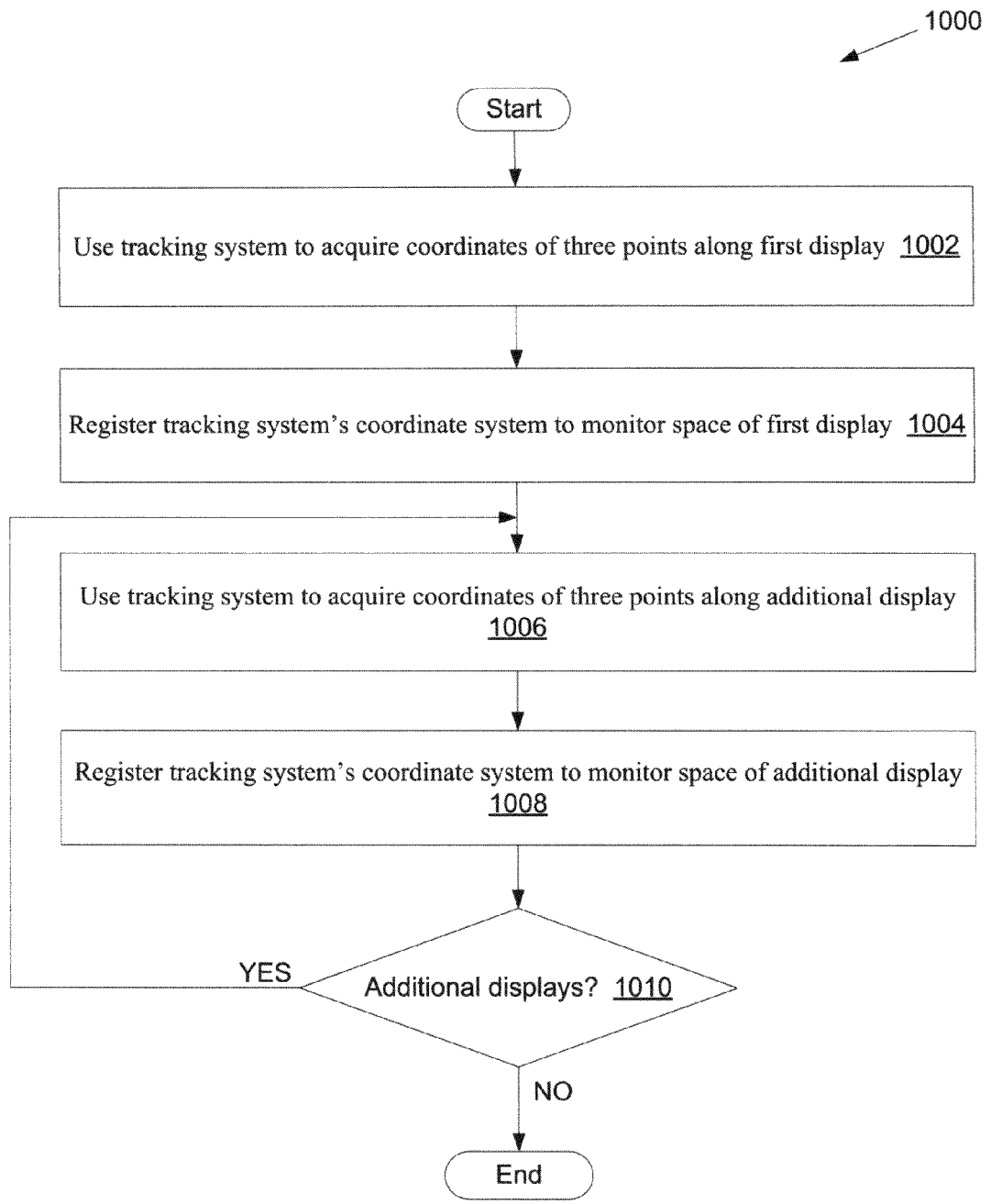
FIG. 10 illustrates a flow diagram of one embodiment for a method of calibrating reference frames of multiple monitors with a tracking system.

FIG. 10 illustrates a flow diagram of one embodiment for a method 1000 of registering reference frames of multiple monitors with a tracking system. The method is performed by processing logic that comprises hardware (e.g., circuitry, dedicated logic, programmable logic, microcode, etc.), software (such as instructions run on a processing device), or a combination thereof. In one embodiment, method 1000 is performed by the computing device 105 of FIG. 1B.

Referring to FIG. 10, at block 1002 of method 1000, as a tracked object (e.g., an electronic pointer) is positioned at three different locations along a first display, the position sensor of a tracking system acquires coordinates for each of the three points and reports the coordinates to a computing device. At block 1004, the computing device detects a first monitor space (e.g., a 3D stereoscopic virtual space) provided by the first display, and dynamically aligns the frame of reference of the first display to the tracking system as explained above with reference to FIGS. 8-9. In one embodiment this includes computing a first transformation matrix, which may resemble the transformation matrix shown above in equation 1. The first transformation matrix may be used to transform coordinates from the user space to a first monitor space of the first display.

At block 1006, as the tracked object (e.g., an electronic pointer) is positioned at three different locations along a second display, the position sensor of the tracking system acquires coordinates for each of the three points and reports the coordinates to the computing device. At block 1008, the computing device detects a second monitor space (e.g., a standard workspace) of the second visual output device, and dynamically aligns the frame of reference of the second display to the tracking system as explained above with reference to FIGS. 8-9. In one embodiment this includes computing a second transformation matrix, which may resemble the transformation matrix shown above in equation 1. The second transformation matrix may be used to transform coordinates from the user space to a second monitor space of the second display.

At block 1010, the computing device determines whether the tracking system's coordinate system needs to be calibrated with the coordinate systems of any additional displays. If the tracking system's coordinate system has not been calibrated to all displays, the method returns to block 1006. If the calibration has been performed with reference to all displays, the method ends.

Once the virtual spaces and/or standard workspaces are calibrated, an input from an input device (e.g., a 6D input device) can accurately adjust what is displayed in one or multiple virtual spaces and/or standard workspaces. Where the input affects multiple monitor spaces, this may be implemented by directly providing the input to each of the monitor spaces. Alternatively, an active monitor space may receive the input and forward the input to one or more additional monitor spaces.

Consider an example in which two virtual spaces are provided, each of which displays a different view of the same patient anatomy. In a first instance, a zoom out command may apply to both of the virtual spaces, zooming out the image of the patient anatomy shown in both virtual spaces. In a second instance, the zoom out command may apply only to one of the virtual spaces, zooming out the image of the patient anatomy shown only in that virtual space.

A user input may apply to one or more monitor spaces (e.g., to particular virtual spaces or standard workspaces) by selecting those monitor spaces. Monitor spaces may be selected, for example, by moving a cursor into that monitor space, by pressing a key assigned to that monitor space, by pointing a 6D input device at the monitor providing the monitor space, or by other means. A single monitor space may be assigned as an active monitor space. Received inputs may be directed to the active monitor space, which may or may not forward those received inputs to other monitor spaces.

In one embodiment, different areas of the user space are assigned to particular monitor spaces (e.g., to particular virtual spaces or standard workspaces). For example, a first region of the user space may be assigned to a first virtual space and a second region may be assigned to a second virtual space. Accordingly, when a tracked object, for example, is detected in the first region of the user space, the first monitor space may become active and user input may affect the first virtual space. Similarly, when the tracked object is detected in the second region of the user space, the second monitor space may become active and the user input may affect the second virtual space.

Often, when multiple monitors are used, those monitors do not have the same resolution. This can cause a cursor to appear to jump vertically when it is moved from one monitor to the other, because the representation of a particular pixel on one monitor is at a different location than the representation of the same pixel on the other monitor. In one embodiment, this apparent jump can be ameliorated by providing a band at an edge (or edges) of one or more of the monitors, as shown in FIG. 2A.

Figure 11:
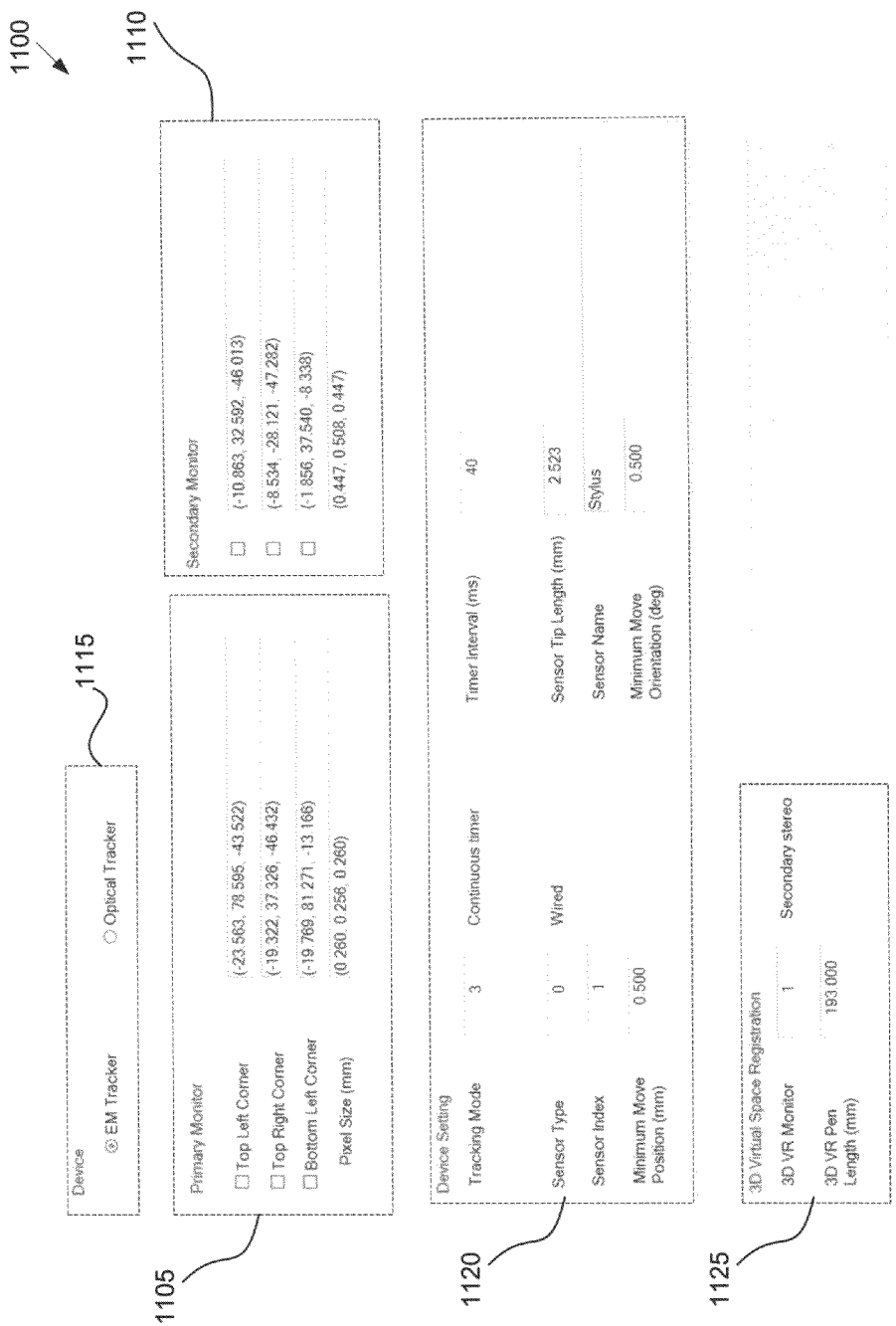
FIG. 11 illustrates a calibration screen that shows multiple calibration settings for an electromagnetic tracking system, in accordance with one embodiment of the present invention.

FIG. 11 illustrates a calibration screen 1100 that shows multiple calibration settings for an electromagnetic tracking system, in accordance with one embodiment of the present invention. The illustrated calibration screen 1100 includes calibration settings for a primary monitor 1105 and calibration settings for a secondary monitor 1110. The calibration settings may be acquired, for example, using method 900 and/or method 1000. As shown, and not by way of limitation, each of the calibration settings 1105, 1110 includes coordinates for a top left corner, a top right corner, and a bottom left corner.

The calibration screen 1100 includes a tracker type 1115, which in the illustrated embodiment can be an electromagnetic (EM) tracker or an optical tracker. The calibration screen further includes device settings/parameters 1120 for the tracking system. The device settings 1120 include a minimum move position (position threshold) and a minimum move orientation (orientation threshold). The example position threshold is 0.5 mm and the example orientation threshold is 0.5 degrees. Detected motions that are below these threshold values will not be reported by the tracking system. The device settings 1120 further include a sensor name, sensor type, sensor index, and sensor tip length. These parameters identify the tracked object that will be detected by the tracking system. For example, the specified tracked object shown in calibration screen is a wired stylus with a sensor tip length of 2.523 mm. The device settings 1120 further include a tracking mode and a timer interval. Example tracking modes include a continuous timer tracking mode (as shown), a wait for report tracking mode, and a combination of these two modes. In a continuous timer tracking mode, the tracking system is polled for new data at a frequency controlled by the timer interval. In a wait for report tracking mode, the tracking system reports data as the data is acquired. When a wait for report tracking mode is selected, no timer interval may be used.

Ultimately, each treatment plan will be used to treat a patient in a reference frame of a treatment delivery system. In one embodiment, the reference frame of the treatment delivery system will be registered with a reference frame of a primary CT volume (e.g., by generating DRRs from the CT volume and registering the DRRs with x-ray images taken of the patient as known to the skilled artisan) used in the treatment plan. This ensures that a target included in the CT volume is at a known position in the treatment delivery system during treatment. Therefore, all data in the treatment plan should be recorded in a coordinate system (reference frame) of the primary CT volume. Accordingly, in addition to the 6D input devices being calibrated to the virtual spaces and/or standard workspaces of displays used, the virtual space(s) (and possibly the standard workspaces) also need to be calibrated to a CT space of an imaged CT volume. The calibration of the virtual space (or standard workspace) to the CT space may be performed before or after the calibration of the 6D input device(s) to the virtual space and/or standard workspace.

Figure 12:
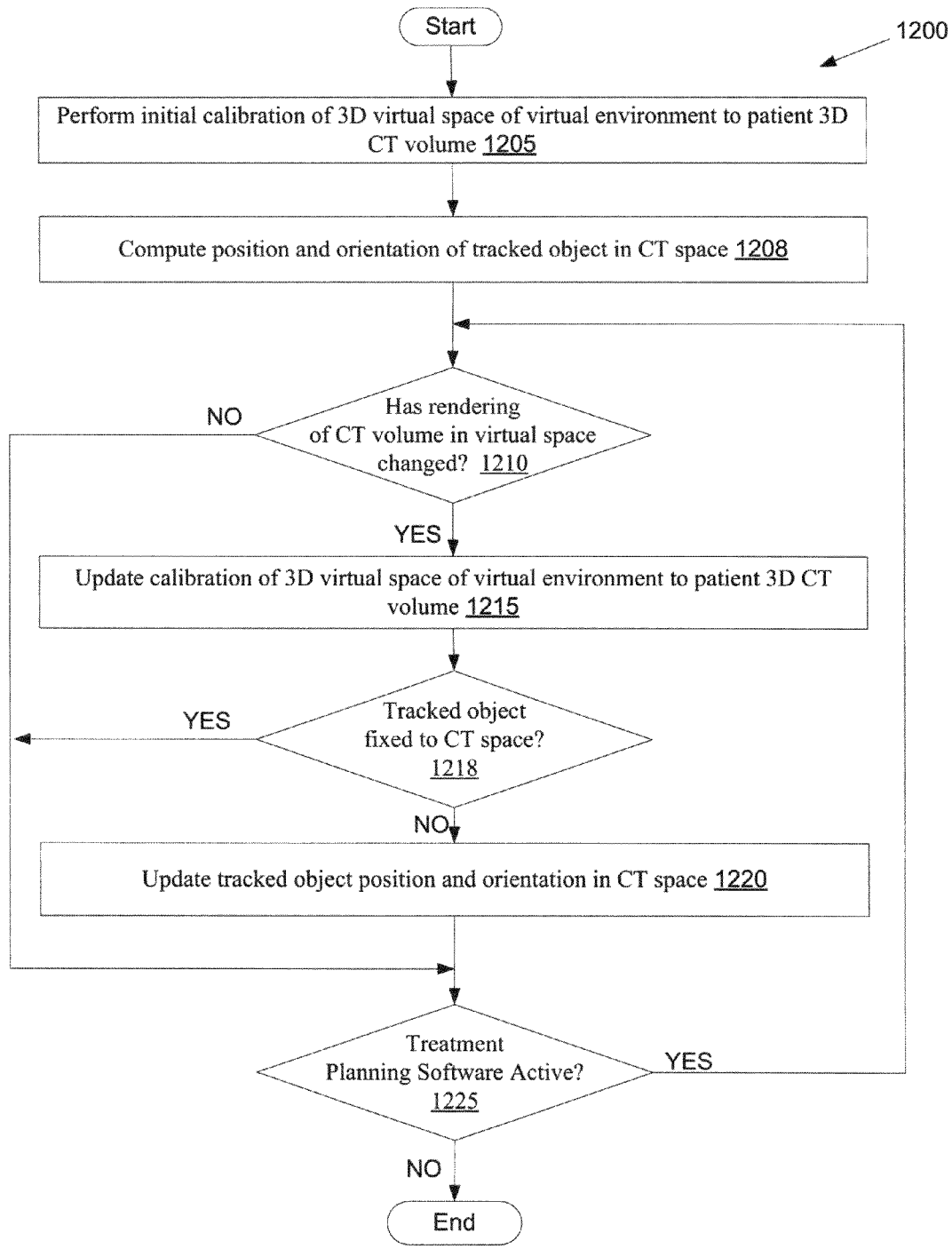
FIG. 12 illustrates a flow diagram of one embodiment for a method of calibrating a CT volume reference frame with a virtual space reference frame.

FIG. 12 illustrates a flow diagram of one embodiment for a method 1200 of calibrating a CT volume (CT space) reference frame with a virtual space reference frame. Method 1200 may also apply to calibrating the CT space reference frame to a standard workspace reference frame (of a monoscopic monitor). The method is performed by processing logic that comprises hardware (e.g., circuitry, dedicated logic, programmable logic, microcode, etc.), software (such as instructions run on a processing device), or a combination thereof. In one embodiment, method 1200 is performed by the computing device 105 of FIG. 1B. If multiple displays are used, method 1200 may be performed separately for the virtual space (or standard workspace) presented by each display.

Referring to FIG. 12, at block 1205 of method 1200, the computing device performs an initial calibration of the 3D virtual space presented by a stereoscopic display to a patient CT volume (CT space). The CT volume may be an image of, for example, a skull, head, lung, liver, prostate, upper torso, etc. of a patient. In one embodiment, the CT volume is initially rendered in the virtual space such that the axes of the CT space are parallel to the corresponding axes of the virtual space. Therefore, the initial calibration may be performed by calculating a scaling factor between the rendered CT volume and the virtual space, and a position of the CT volume relative to an origin of the virtual space. In one embodiment, an initial scaling factor may be computed by determining a vertical and horizontal size of the CT volume (in millimeters), comparing this to a vertical and horizontal resolution of the display, and determining how many millimeters are represented by each pixel in the vertical and horizontal directions, as represented in the following equations:

$$S_{11} = \frac{X_{CT}}{Res_{Horiz}} \quad \text{(equation 3)}$$

$$S_{22} = \frac{Y_{CT}}{Res_{Vert}} \quad \text{(equation 4)}$$

Where $S_{11}$ is the scaling factor along the x-axis, $X_{CT}$ is the length of the CT volume along the x-axis, and $Res_{Horiz}$ is the resolution of the display along the x-axis, and where $S_{22}$ is the scaling factor along the y-axis, $Y_{CT}$ is the length of the CT volume along the y-axis, and $Res_{Vert}$ is the resolution of the display along the y-axis. The scaling factor along the z-axis ($S_{33}$) may be set based on the values of $S_{11}$, $S_{22}$, a combination of $S_{11}$ and $S_{22}$, or some other criteria.

In one embodiment, in which three corners (e.g., vO, vX, vY) of a display are used to perform calibration of the user space to the virtual space, a scale factor between the CT space and the virtual space is automatically set. The CT images have a fixed resolution based on the resolution of the imager that was used to generate the CT images. The stereo monitor also has a set vertical and horizontal resolution. Therefore, the CT dimensions along one plane and the monitor dimensions (in pixels) along one plane are known. These known dimensions may be used to correlate a scaling between the CT space and the virtual space. In another embodiment, in which coordinates of four locations are recorded for calibrating the tracking system to the virtual space, the delta between two of the locations is used to set the scaling factor along the z-axis ($S_{33}$).

In one embodiment, the scaling between the CT space and the virtual space in one or more dimensions may be adjusted by a user. In one embodiment, a scaling slide bar is provided to a user for adjusting the scaling. The scaling slide bar may scale all dimensions, or may scale just one or two dimensions. The slide bar may therefore squeeze or stretch an image along various dimensions.

Initial translations along the x-axis, y-axis and z-axis may be based on predetermined initial translation settings. In one embodiment, the CT volume is initially rendered such that the origin of the CT volume corresponds to the origin of the virtual space. Alternatively, the CT volume may initially be placed at a center of the visual output device (or other predetermined location within the visual output device), and the translations necessary to place the CT volume in the center (or other predetermined location) of the visual output device may be computed.

In one embodiment, the initial calibration of the virtual space to the CT space is represented by the following 4×4 matrix:

$$M_{2i} = \begin{bmatrix} S_{11} & 0 & 0 & T_x \\ 0 & S_{22} & 0 & T_y \\ 0 & 0 & S_{33} & T_z \\ 0 & 0 & 0 & 1 \end{bmatrix} \quad \text{(equation 5)}$$

This matrix can be combined with matrix $M_1$ into a single matrix, or may be applied along with $M_1$ as a matrix chain that can convert data received in the reference frame of the 6D input device(s) to the CT space. This calibration/registration should not be confused with the 2D/3D registration that is performed to align the pre-treatment CT images with in treatment x-ray images during patient radiotherapy treatment.

At block 1208, the computing device computes a position and orientation of a tracked object in the CT space. The position and orientation may be determined by multiplying a vector or vectors representing a position of the tracked object in the user space (e.g., (x, y, z, w), where w represents a scaling value) by the matrix $M_1$ and then by the matrix $M_2$.

When a 6D input causes a rotation/pan/zoom of the image, the image changes. The image is then re-rendered (e.g., using OpenGL, DirectX, or other graphics application programming interface). At block 1210, the computing device determines whether a rendering of the CT volume in the virtual space has changed (or whether a command that will cause the rendering to change has been received). If the rendering has changed, or a command has been received that, once executed, will cause the rendering to change, the method proceeds to block 1215. If the rendering has not changed, the method proceeds to block 1225.

At block 1215, the computing device updates the calibration of the 3D virtual space to the CT space of the CT volume. For example, the calibration may be changed, and a geometric transformation may be performed, when any image manipulation (pan, rotate, zoom) occurs. The transformation matrix includes parameters of rotation, scaling and perspective projection to reflect the geometric linkage among the visualized artifacts in the camera world, in the VR space, and the patient data in the CT space. For example, when a pan operation is performed, the matrix $M_{2i}$ may be updated to matrix $M_{2j}$ to change the values of one or more of $T_x$, $T_y$ and $T_z$ to reflect a new positional relationship between the virtual space and the CT space. Similarly, when a zoom operation is performed, the values of $S_{11}$, $S_{22}$ and $S_{33}$ may be updated to reflect a new scale between the CT volume and the virtual space. Additionally, when a rotation operation is performed, multiple values of the matrix $M_{2j}$ may be changed. Therefore, regardless of a relationship between the CT space and the virtual space, when a user, for example, delineates a contour of a VOI in the virtual space, that contour can be recorded in the CT space, and ultimately be used to treat the patient. In one embodiment, the updated registration matrix has the form:

$$M_{2j} = \begin{bmatrix} M_{11} & M_{12} & M_{13} & T_x \\ M_{21} & M_{22} & M_{23} & T_y \\ M_{31} & M_{32} & M_{33} & T_z \\ 0 & 0 & 0 & 1 \end{bmatrix} \quad \text{(equation 6)}$$

Where $M_{12}$, $M_{13}$, $M_{21}$, $M_{23}$, $M_{31}$ and $M_{32}$ are based on any rotations that have been performed in the virtual space, where $M_{11}$, $M_{22}$ and $M_{33}$ are based on a current scaling factor (including changes in scaling factor based on zoom operations)

and on any rotations that have been performed in the virtual space, and where changes to $T_x$, $T_y$ and $T_z$ are based on pan operations.

At block 1218, the computing device determines whether the tracked object is fixed to the CT space. If the tracked object is fixed to the CT space, as the relationship between the CT space and the virtual space changes, the tracked object maintains its relationship to the CT space. Therefore, the rendering of the tracked object in the virtual space will appear to rotate and pan along with the CT volume. If the tracked object is not fixed to the CT space, then the relationship between the tracked object and the virtual space remains fixed, regardless of how the relationship between the CT space and the virtual space changes. However, it is important to know the relationship between the CT space and the tracked object. Therefore, if the tracked object is not fixed to the CT space, the method continues to block 1220, and the tracked object position and orientation in the CT space is updated. If the tracked object is fixed to the CT space, the method proceeds to block 1225.

At block 1220, the relationship between the tracked object and the CT space is updated. In one embodiment, this is performed by performing the mathematical operation:

$$\begin{bmatrix} X \\ Y \\ Z \\ 1 \end{bmatrix}_{CT} = (P \cdot M_{2j})^{-1} \begin{pmatrix} x \\ y \\ z \\ 1 \end{pmatrix} \quad \text{(equation 7)}$$

Where X, Y, Z are the coordinates of the tracked object in the CT space, where x, y, z are the coordinates of the tracked object in the user space, wherein $(P \cdot M_{2j})^{-1}$ is the inverse matrix of $(P \cdot M_{2j})$, and where P is a 4×4 matrix representing an orthographic projection in the virtual space.

At block 1225, the computing device determines whether treatment planning software that is being used to render the CT volume is still active/running. So long as the treatment planning software is active, the method returns to block 1210. Otherwise, the method ends.

Figure 13:
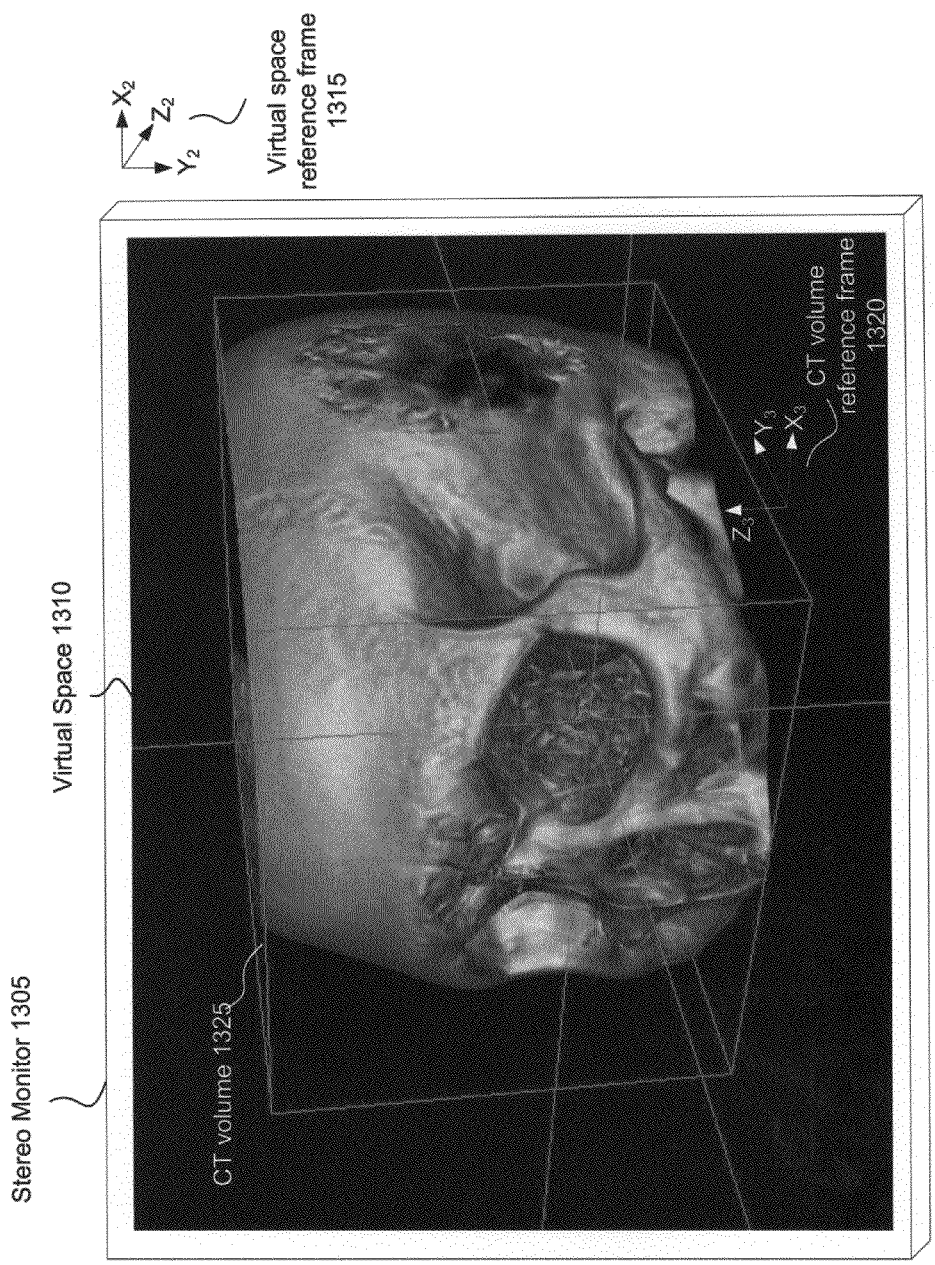
FIG. 13 illustrates a stereo monitor in which a CT volume is rendered in a virtual space, in accordance with one embodiment of the present invention.

FIG. 13 illustrates a stereo monitor 1305 in which a CT volume 1325 is rendered in a 3D stereoscopic virtual space 1310. The CT volume (CT space) 1325 has been calibrated with the virtual space 1310 using method 1200 such that a relationship between a reference frame of the virtual space 1315 and a reference frame of the CT volume 1325 is known. This relationship may be represented by a 4×4 matrix (e.g., matrix $M_{2j}$ above). As shown, the reference frame of the CT volume 1320 is not aligned with the reference frame of the virtual space 1315.

Once the calibration has been performed, as a tracked object is moved within a field of view of the positional sensor, the computing device may track the object and determine a corresponding position and/or trajectory of the tracked object in the virtual environment and in the CT space. In one embodiment, the computing device tracks an orientation of the tracked object in the 3D virtual space 1310 of the virtual environment, and in the 3D CT space. Therefore, as the tracked object is rotated, that rotation is tracked and represented in the virtual space, and in the CT space.

Figure 14A:
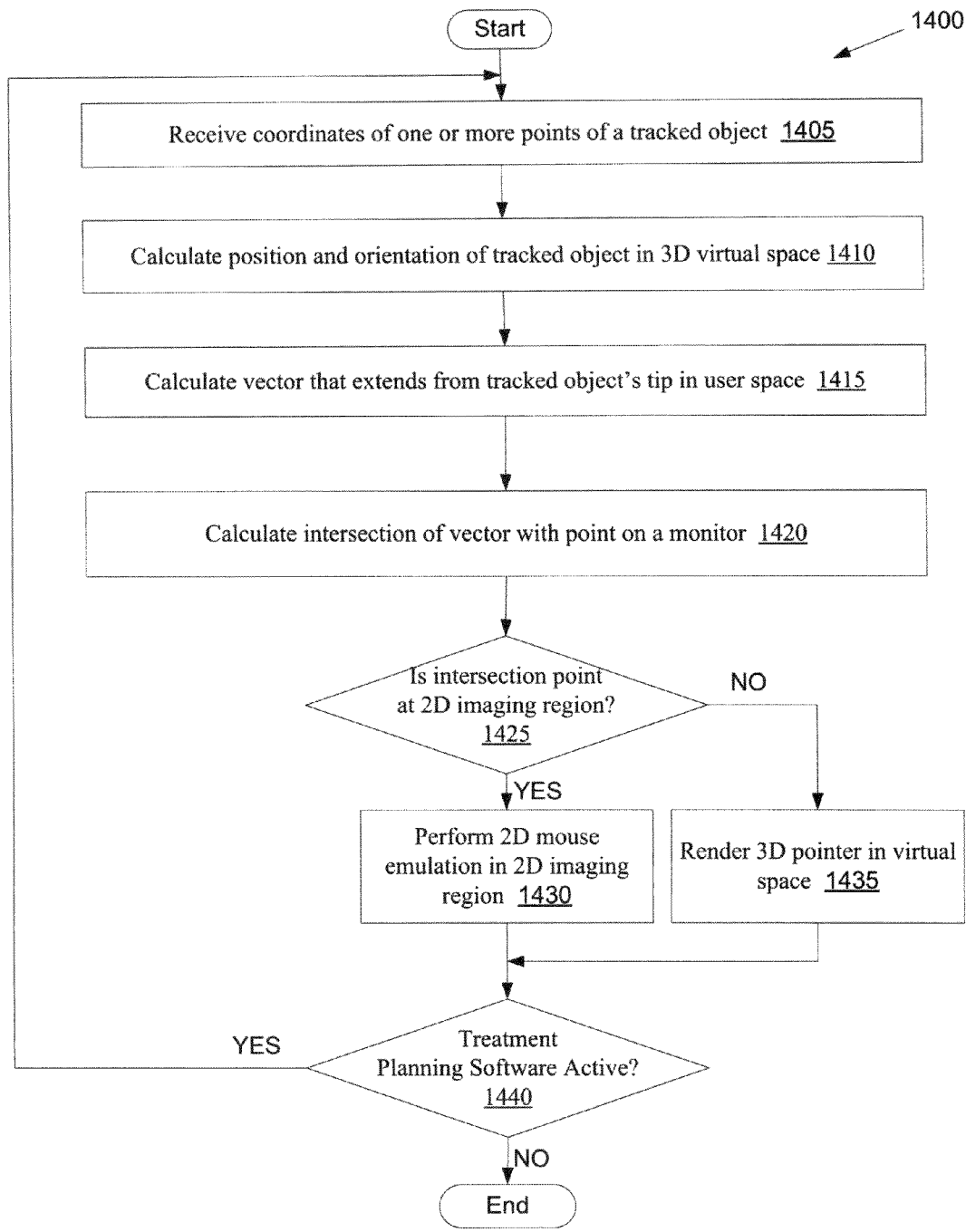
FIG. 14A illustrates a flow diagram of one embodiment for a method of tracking an object, and rendering the tracked object in a virtual space.

FIG. 14A illustrates a flow diagram of one embodiment for a method 1400 of tracking an object, and rendering the tracked object in a virtual space. Method 1400 may also apply to tracking an object and rendering the tracked object in a standard workspace of a monoscopic display. The method is performed by processing logic that comprises hardware (e.g., circuitry, dedicated logic, programmable logic, microcode, etc.), software (such as instructions run on a processing device), or a combination thereof. In one embodiment, method 1400 is performed by the computing device 105 of FIG. 1B. If multiple visual output devices (displays) are used, method 1400 may be performed separately for the virtual space or standard workspace presented by each visual output device.

Referring to FIG. 14A, at block 1405 of method 1400, the computing device receives coordinates of one or more points of a tracked object. For example, and not by way of limitation, the tracked object may be an electronic pointer, data glove, or other object. The computing device may receive the coordinates from a positional sensor, such as an electromagnetic sensor or an optical sensor.

At block 1410, the computing device determines a position and orientation of the tracked object in the virtual space and/or standard workspace. In one embodiment, the position and orientation is determined based on coordinates of at least two points of the tracked object. If the relationship between the at least two points is known, then the location of the at least two points can be used to determine the orientation. Alternatively, the orientation can be determined using coordinates of one or more points along with inclination data received from an accelerometer included in the tracked object. The orientation of the tracked object in the virtual space and/or the standard workspace can be computed by multiplying a vector representing each point by calibration matrix $M_1$. The known physical relationship between the points can then be used to determine the orientation of the tracked object in the virtual space and/or the standard workspace. In one embodiment, the orientation of the tracked object in the CT space is also computed. This may be performed by transforming the orientation from the virtual space to the CT space using calibration matrix $M_{2j}$.

Calculating the position of the tracked object in one embodiment includes calculating a position of a tip of the tracked object in the virtual space and/or the standard workspace. In one embodiment, the tracked object's tip is one of the points of the tracked object. In such an embodiment, the absolute position of the tip can be computed by multiplying the vector that represents the position of the tracked object's tip in the user space by the calibration matrix $M_1$. If the tip of the tracked object does not correspond to one of the tracked points, then the tip position can be computed based on the orientation of the tracked object and a known distance from one or more of the tracked points to the tip of the tracked object. In one embodiment, the absolute position of the tracked object in the CT space is also computed. A change in position and orientation may also be computed in addition to the position and orientation. The change in position and orientation may be computed by subtracting a previous position and orientation in the virtual space and/or the standard workspace from the current position and orientation in the virtual space or the standard workspace. This may also be performed in the CT space.

In one embodiment, the tracked object has its own tracked object coordinate system (reference frame), in which the tip of the tracked object is the origin, and the x-axis is aligned with a vector extending through the center of the tracked object towards the tip of the tracked object. In one embodiment, computing the orientation of the tracked object includes determining a relationship between the tracked object reference frame and the user space reference frame and/or virtual space reference frame (or standard workspace reference frame).

At block 1420, the computing device calculates a vector that extends from the tracked object's tip in the virtual spaces (or standard workspaces) of each of the displays. The vector in one embodiment is aligned with the orientation of the tracked object, which in one embodiment is computed at block 1410. The orientation of the tracked object is then computed, if it has not already been computed. In one embodiment, the vector can be represented by a matrix as follows:

$$\begin{bmatrix} X \\ Y \\ Z \end{bmatrix} = [R] \begin{bmatrix} x_p \\ y_p \\ z_p \end{bmatrix} + \begin{bmatrix} x_0 \\ y_0 \\ z_0 \end{bmatrix} \quad \text{(equation 8)}$$

Where (X, Y, Z) are coordinates in the virtual space coordinate system, ($x_p$, $y_p$, $z_p$) are coordinates in a reference frame of the tracked object, ($x_0$, $y_0$, $z_0$) are coordinates in the user space reference frame, and R is a 3×3 rotation matrix based on the orientation of the tracked object in the user space, as follows:

$$R = \begin{bmatrix} \cos\psi\cos\theta & \cos\psi\sin\theta\sin\varphi - \sin\psi\cos\theta & \cos\psi\sin\theta\cos\varphi + \sin\psi\sin\varphi \\ \sin\psi\cos\theta & \cos\psi\cos\theta + \sin\psi\sin\theta\sin\varphi & \sin\psi\sin\theta\cos\varphi - \cos\psi\sin\varphi \\ -\sin\theta & \cos\theta\sin\varphi & \cos\theta\cos\varphi \end{bmatrix} \quad \text{(equation 9)}$$

Where $\psi$=rotation about the z-axis, $\phi$=rotation about the x-axis and $\theta$=rotation about the y-axis.

At block 1420, an intersection of the calculated vector with a display is computed. Method 950 and/or 1000 describe determining the locations and orientations of one or more monitors relative to a tracking device. The intersection in one embodiment is computed by performing the following operations:

$$\begin{bmatrix} X \\ Y \\ Z \end{bmatrix} = [R_A] \left( [R][R_B] \begin{bmatrix} x_p \\ y_p \\ z_p \end{bmatrix} + \begin{bmatrix} x_0 \\ y_0 \\ z_0 \end{bmatrix} \right) \quad \text{(equation 10)}$$

Where $R_A$ is a 3D to 2D projection matrix, and $R_B$ is a 3D to 1D projection matrix, as follows:

$$[R_A] = \begin{bmatrix} 1 & 0 & 0 \\ 0 & 1 & 0 \\ 0 & 0 & 0 \end{bmatrix} \quad \text{(equation 11)}$$

$$[R_B] = \begin{bmatrix} 1 & 0 & 0 \\ 0 & 0 & 0 \\ 0 & 0 & 0 \end{bmatrix} \quad \text{(equation 12)}$$

After performing the above operations, equation 9 resembles:

$$\begin{bmatrix} X \\ Y \\ 0 \end{bmatrix} = [R] \begin{bmatrix} x_p \\ 0 \\ 0 \end{bmatrix} + \begin{bmatrix} x_0 \\ y_0 \\ z_0 \end{bmatrix} \quad \text{(equation 13)}$$

At block 1425, the computing device determines whether the intersection point of the vector is with a regular monoscopic monitor or with a 2D imaging region of a stereoscopic monitor. If the intersection point is with a 2D imaging region of a stereoscopic monitor or with a monoscopic monitor, the method continues to block 1430. Otherwise, the method continues to block 1435.

At block 1430, a 2D mouse emulation is performed. For the 2D mouse emulation, a 2D pointer is rendered at the intersection point. The method then continues to block 1440. The location of the intersection point may be changed by rotating (changing orientation for) the electronic pointer. Therefore, the electronic pointer can control a cursor in a 2D region simply by tilting the electronic pointer.

At block 1435, a virtual 3D pointer is rendered in the 3D virtual space of the stereoscopic monitor. In one embodiment, the computing device reports 6D tracking data including the tracked object's geometry in a two coordinate system format. In one embodiment, the two coordinate systems include the virtual space coordinate system and the coordinate system of the tracking system (user reference frame). The two coordinate system format may be used for visualization purposes to help orient a user to a relationship between the two coordinate systems. The method then continues to block 1440.

At block 1440, the computing device determines whether treatment planning software is still active/running. So long as the treatment planning software is active, the method returns to block 1405. Therefore, as the tracked object is rotated and/or repositioned, the position and orientation of the tracked object in the virtual space and/or CT space will be updated.

Figure 14B:
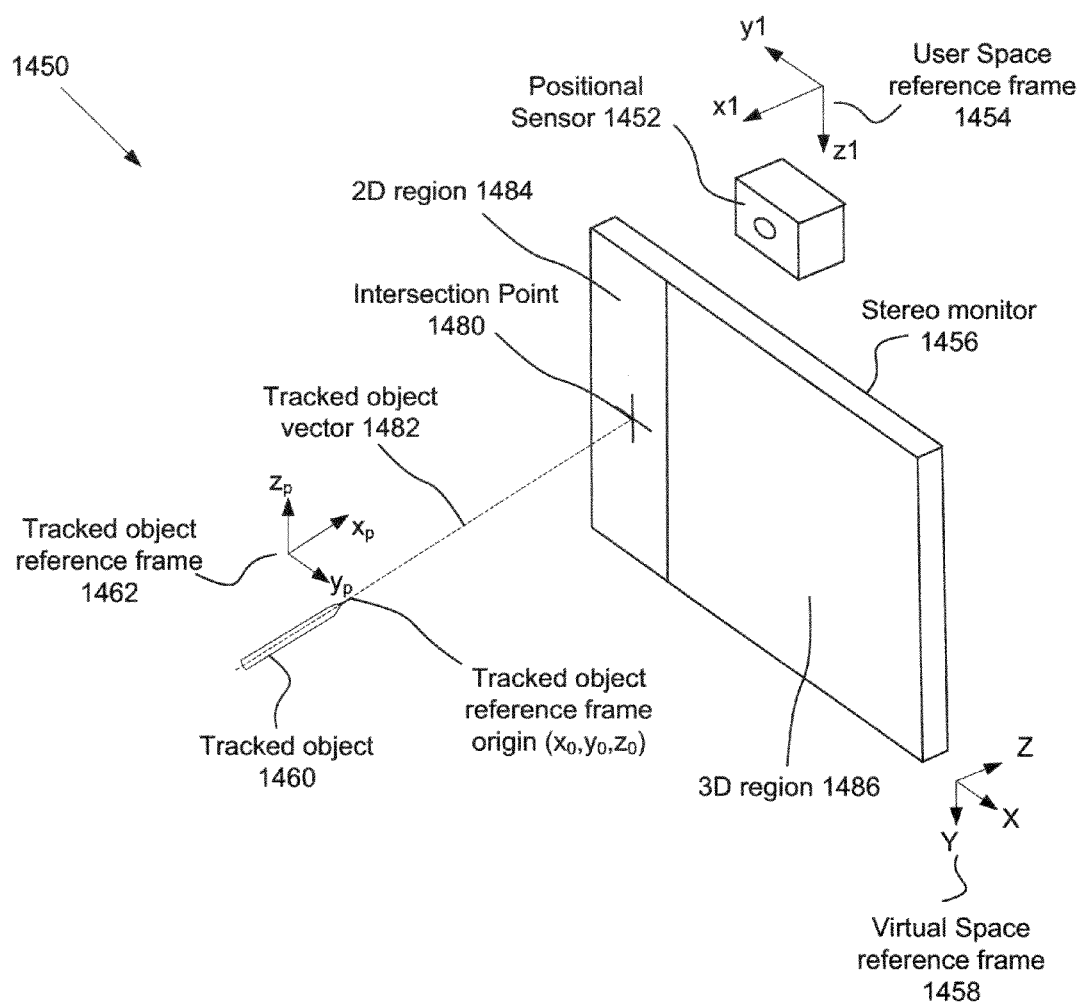
FIG. 14B illustrates an example of 2D mouse emulation, in accordance with one embodiment of the present invention.

FIG. 14B illustrates an example of 2D mouse emulation 1450, in accordance with one embodiment of the present invention. FIG. 14B includes a positional sensor 1452, a tracked object 1460, and a stereo monitor 1458 having a 2D region 1484 and a 3D stereo region 1486. The positional sensor 1452 measures positions and orientations of the tracked object 1460 in a user space reference frame 1454. The stereo monitor 1456 displays a virtual environment in a virtual space reference frame 1458. The tracked object has a tracked object reference frame 1482 in which the $x_p$ axis is aligned with a tracked object vector 1482 that extends from the tracked object 1460. An intersection point 1480 of the tracked object vector 1482 with the stereo monitor 1456 can be computed by setting $z_p$ and $y_p$ to zero, and by setting Z to zero, as mathematically shown in equation 13 above. In the illustrated example, the intersection point 1480 is in the 2D region 1484, and therefore 2D mouse emulation would be performed.

Software Architecture

Figure 15:
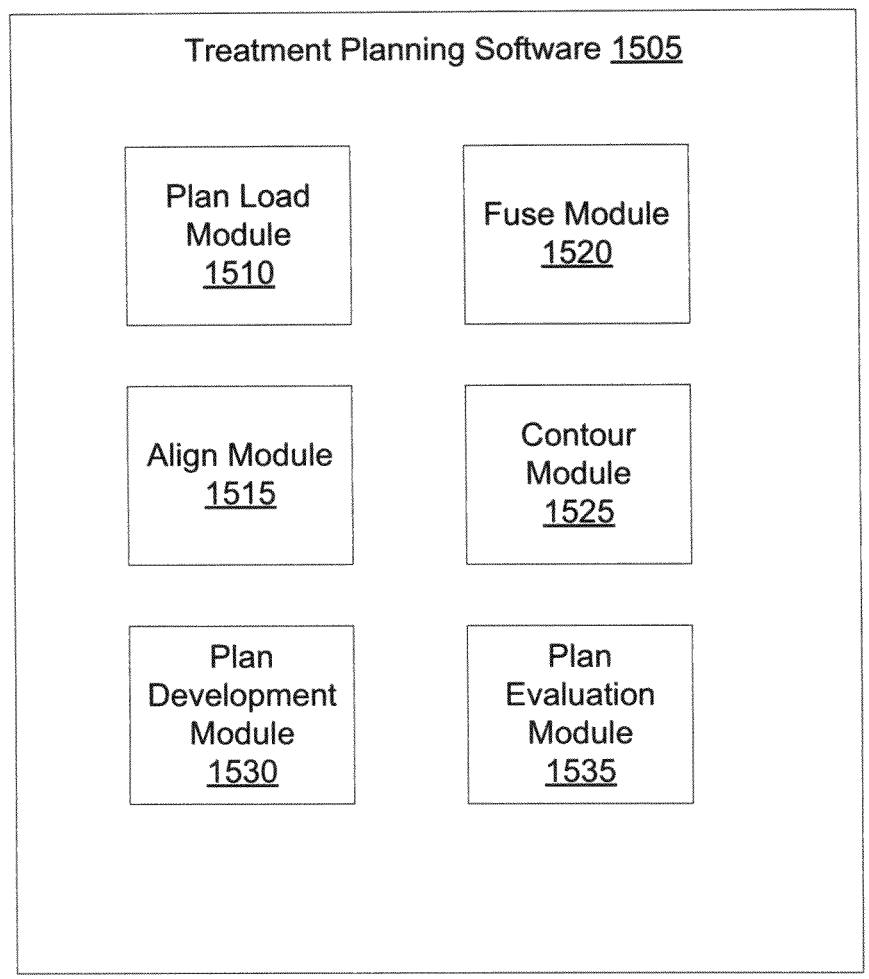
FIG. 15 illustrates a software architecture for treatment planning software, in accordance with one embodiment of the present invention.

FIG. 15 illustrates a software architecture for treatment planning software 1505, in accordance with one embodiment of the present invention. The treatment planning software 1505 may be implemented using hardware, software, firmware or combinations thereof. The treatment planning software 1505 may be written in a variety of programming languages, such as, for example, C/C++ and/or assembly, etc. The treatment planning software 1505 may run on an operating system (OS) such as the Windows® OS from Microsoft Corporation of Washington or a Mac OS from Apple Computer of California. Alternatively, the OS may be a Unix, Linux, or other operating systems (e.g., embedded or real-time operating system), etc. The software and OS may be run on any type of platform, for example, a personal computer (PC) platform, workstation, etc.

The treatment planning software 1505 may be designed for use with an image-guided, robotic-based radiation treatment system (e.g., for performing radiosurgery) such as the CyberKnife® system developed by Accuray Incorporated of California. Alternatively, the treatment planning software 1505 may be used with another type of treatment delivery system, for example, a gantry based (isocentric) intensity modulated radiotherapy (IMRT) system or a stereotactic frame system having a distributed radiation source (e.g., a cobalt 60 gamma ray source) such as the GammaKnife®, available from Elekta of Sweden.

In one embodiment, the treatment planning software 1505 is fully compliant with the DICOM 3.0 standard for the distribution and viewing of medical images and the DICOM-RT standard for viewing radiotherapy information overlain on medical images, and the treatment planning software is preconfigured with these utilities and requires no additional software.

With a unique real-time optimization feedback process, the treatment planning software 1505 allows clinicians to make adjustments in a 3D stereoscopic (or volumetric) virtual environment during plan generation and plan optimization, an advancement that significantly accelerates and simplifies the creation of treatment plans. The treatment planning software 1505 includes advanced image fusion capabilities that enable clinicians to fuse images automatically or manually from multiple modalities, including CT, magnetic resonance (MR), positron emission tomography (PET), and 3D rotational angiography (3DRA). Together with an intuitive user interface and real-time feedback during the image fusion process, the treatment planning software 1505 provides clinicians with the tools by which to create rich patient models (e.g., patient models that are derived from multiple imaging modalities) that can be essential for accurately defining regions of interest during treatment planning.

Treatment planning software 1505 corresponds to treatment planning software 130 that runs on computing device 105 of FIG. 1B. In one embodiment, the treatment planning software 1505 includes a plan load module 1510, an align module 1515, a fuse module 1520, a contour module 1525, a plan development module 1530 and a plan evaluation module 1535. In alternative embodiments, more or fewer modules may be included in the treatment planning software 1505. Each module may perform one or more treatment planning operations and/or enter one or more application modes. Where fewer modules than those described are included in the treatment planning software 1505, some modules may perform treatment planning operations of more than one of the modules depicted in FIG. 15.

The plan load module 1510 loads existing treatment plans and/or initiates new treatment plans. Initiating new treatment plans may include loading diagnostic images. Plan load module 1510 may load treatment plans and/or diagnostic images that are stored locally on a computing device that hosts the treatment planning software 1505. Alternatively, plan load module 1510 may load treatment plans and/or diagnostic images from remote locations, such as from a treatment plan database. Treatment planning operations performed by the plan load module 1510 are described in greater detail below under the heading "load task."

The fuse module 1520 registers multiple virtual artifacts together, where each of the virtual artifacts may be a patient image based on diagnostic image data. The images may be from the same or different image modalities. The image fusion may be performed manually, automatically, or semi-automatically. In one embodiment, the images to be fused are displayed in the virtual environment as image fusion is being performed. Treatment planning operations performed by the fuse module 1520 are described in greater detail below under the heading "fuse task."

The align module 1515 sets treatment parameters (e.g., number of treatment stages, radiation dose, treatment path, etc.) and aligns a machine center of a radiation delivery system with a CT center. The align module 1515 may perform one or more treatment planning operations after the fuse module and/or load module have completed performing treatment planning operations. Treatment planning operations performed by the align module 1515 are described in greater detail below under the heading "align task."

The contour module 1525 designates and delineates volumes of interest based on user input. In one embodiment, the user input is received via 6D input devices. Designation and delineation of the volumes of interest may be displayed in a 3D virtual space of the virtual environment. Contour module 1525 can perform treatment planning operations after the fuse module has completed performing any treatment planning operations. Treatment planning operations performed by the contour module 1525 are described in greater detail below under the heading "contour task."

The plan development module 1530 defines parameters that may be used in the treatment planning process. Such parameters may include a density model for modeling radiation absorption of tissue. The plan development module may perform forward treatment planning (e.g., such as isocentric planning) and inverse treatment planning (e.g., such as conformal planning). The plan development module may also perform 4D planning. Treatment planning operations performed by the plan development module 1530 are described in greater detail below under the heading "plan task."

The plan evaluation module 1535 performs one or more treatment plan evaluation operations. These operations provide a user with in depth information regarding how much radiation will be delivered to different portions of a patient's anatomy. The plan evaluation operations may be used to determine refinements to make to the treatment plan in order to maximize radiation delivery to a target and minimize radiation delivery to surrounding tissue. Treatment planning operations performed by the plan evaluation module 1535 are described in greater detail below under the heading "plan evaluation task."

Figure 16:
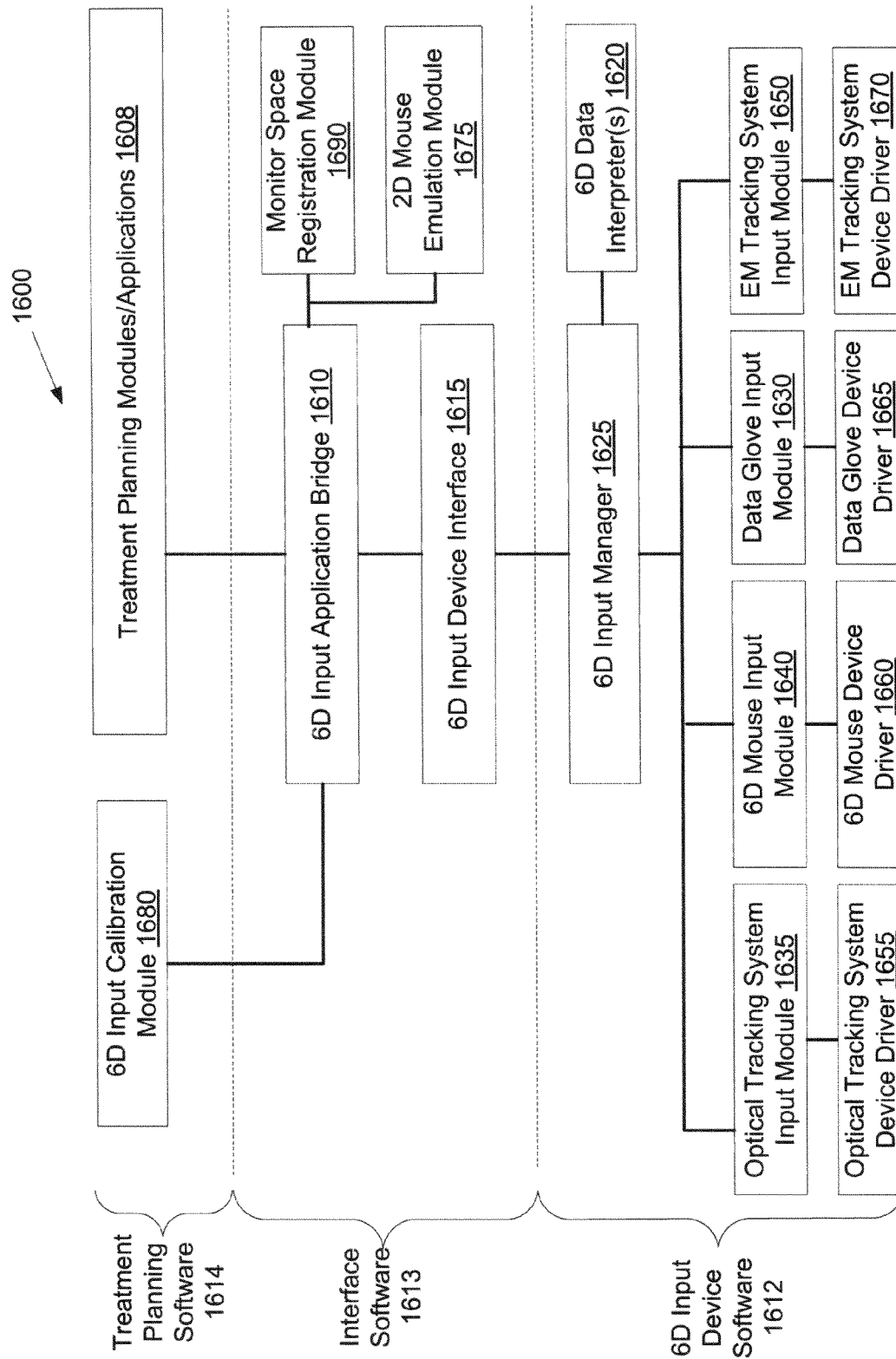
FIG. 16 illustrates a software architecture for interfacing 6D input devices with treatment planning software.

FIG. 16 illustrates a software architecture 1600 for interfacing 6D input devices with treatment planning software 1614. The software architecture 1600 separates 6D input device software 1612 and interface software 1613 from higher level treatment planning software 1614, which may correspond to treatment planning software 1505 of FIG. 15. All of the 6D input device software 1612, interface software 1613 and treatment planning software 1614 may be included in treatment planning software 130 of FIG. 1B.

Referring to FIG. 16, the 6D input software 1612 includes one or more 6D input device drivers 1655-1670. A separate device driver 1655-1670 may be installed on a computing device for each 6D input device that will be used. For example, there may be separate device drivers for a 6D optical tracking system 1655, a 6D mouse 1660, a data glove 1665 and a 6D electromagnetic (EM) tracking system 1670. The 6D input device software 1612 further includes 6D input modules 1635-1650 which are separate software systems (e.g., plugins) that are flexible and extendable for the adding of new 6D input devices. In one embodiment, a separate 6D input module 1635-1650 is used for each 6D input device. Alternatively, a single 6D input module may be used for multiple 6D input devices. As new 6D input devices are added to the treatment planning system, a new 6D input module may be installed for receiving signals from the new 6D input device.

Each 6D input module 1635-1650 may be configured to access/receive input data from a 6D input device driver 1655-1670. Each tracking system input module 1635 may also store configuration parameters such as calibration data that the tracking system input modules 1635-1650 may receive (e.g., from the 6D input manager 1625) at startup. Calibration data may include, for example, movement sensitivity settings (thresholds). For a tracking system input module 1635, 1650, the calibration data may include one or more transformation matrices for transforming positional data from a user space to one or more virtual spaces or standard workspaces (e.g., of multiple monitors). For the data glove input module 1630, the calibration data may include finger flexure thresholds.

The software architecture may include a 6D input manager 1625 that converts the input data from the 6D input devices into a format that is understandable to the treatment planning software 1614 (e.g., to the treatment planning modules/applications 1608). The 6D input manager 1625 can manage each device, which may include receiving data from and sending data to input modules 1635-1650.

The 6D input manager 1625 may collect input data from each input module 1635-1650, and use an appropriate 6D input data interpreter 1620 to determine how to format the input data. In one embodiment, the 6D input manager 1625 includes or is connected with a 6D data interpreter 1620 that either performs the transformation, or provides the 6D input manager 1625 with the information necessary to perform the transformation. There may be one or multiple 6D data interpreters 1620. For example, there may be a different 6D data interpreter 1620 for each 6D input device. Moreover, when a new 6D input device is added, a new 6D data interpreter may be installed, or configuration data for the new 6D input device can be added to an existing 6D data interpreter 1620.

Different input devices take different measurements, and provide those different measurements in various formats. For example, some 6D input devices report delta data, while other 6D input devices report absolute position. Moreover, some 6D input devices provide additional data. For example, the data glove may provide glove orientations, changes in glove position and finger flexion information. The 6D data interpreter(s) 1620 will create a standard format from the input data. The standard 6D input data format in one embodiment consists of position (x, y, z), orientation (yaw, pitch, roll), device ID (identity of input device), data type (delta or absolute), commands (e.g., okay, cancel, rotate image, etc.), device button status (press, hold, release), etc. for the higher level treatment planning software to use. For example, a 6D data interpreter 1620 may translate finger flexure and hand motion data of the data glove into preconfigured gestures (e.g., gesture 1, gesture 2, etc.) and standard commands for image manipulation (e.g., pan, rotate, zoom, OK, Cancel, etc.). The 6D input manager 1625 then reports the formatted input data to the 6D input device interface 1615. Therefore, treatment planning software 1614 can act on all input data in the same manner, regardless from which 6D input device the input data originated.

Higher level treatment planning software 1614 includes multiple treatment planning modules/applications 1608. An application/module may be any software component that operates on top of the virtual environment. In one embodiment, there are multiple levels of application modules, each of which may cause a different application mode to be active. One application module level is based on a current task (as described below). Each task may be performed by a module as described above with reference to FIG. 15. Another application module level is based on an active tool within an active task. For example, within the contour task, a user may select a bumper tool, pen tool, line tool, semi-auto segmentation tool, etc. Another application module level is based on a current step within a task. Some tasks may be divided into multiple steps. Input from the 6D input devices may behave differently depending on the current step in an active task. Depending on the active module or modules, the same input device may behave differently.

Higher level treatment planning software 1614 (e.g., treatment planning modules 1618) can interact with the 6D input device interface 1615 or with the 6D input application bridge 1610. The 6D input device interface 1615 receives input data from 6D input device software, and sends the input data to the 6D input application bridge 1610. Alternatively, or in addition, the 6D input device interface 1615 may temporarily store (buffer) the input data. The 6D input device interface 1615 includes multiple functions for controlling lower level 6D input device software 1612. In one embodiment, the 6D input device interface 1615 includes, without limitation, the functions Create6DInput( ), Calibrate(device), Connect(device), GetData(device), Disconnect(device), IsConnected (device), IsReady(device) and Destroy6DInput( ). These commands enable the 6D input device interface to connect, calibrate, get data from, disconnect, etc. each of the attached 6D input devices. For example, Connect(device) connects a selected device based on recipe parameters, GetData(device) causes data to be gathered from a selected device, and IsReady(device) shows whether the device is ready. The same functions can be used for any 6D input device, even though different input devices may require different inputs, commands, etc. For example, Calibrate(device) is a standard function call for all 6D input devices even though different devices need different calibration parameter recipe settings and report different measurements.

The 6D input application bridge 1610 provides a simplified interface to treatment planning modules/applications 1608. By using the 6D input application bridge 1610, treatment planning software 1614 may not need to directly call the functions included in the 6D input device interface 1615. Treatment planning modules/applications 1608 can choose to interact with the 6D input application bridge 1610 or with the more complex underlying 6D input device interface 1615. For example, when treatment planning software is first initialized, each of the 6D input devices may need to be activated and/or calibrated. The treatment planning software 1614 may make a single call on the bridge to activate all input devices and/or calibrate all input devices rather than make separate calls to the 6D input device interface 1615 for each input device that needs to be activated or calibrated. In one embodiment, a 6D input calibration module 1680 interfaces with the 6D input application bridge 1610 to calibrate one or more attached 6D input devices when the treatment planning software is initialized.

In one embodiment, the 6D input application bridge 1610 temporarily stores (e.g., buffers) latest input data in a common input buffer, and stores latest input data from each input device in separate input device buffers. A treatment planning module 1608 may receive the contents of the common input buffer, or may receive input data from one or more input device buffers. For example, if a treatment planning module only needs 6D mouse data, it may request input data stored in a 6D mouse input buffer. A current application mode (e.g., active application module, task, step, tool, etc.) may determine from which buffer to get input data. When new data is available in the common input buffer or a specific input buffer, the data may be reported to an active treatment planning module/application via messaging. Alternatively, or in addition, treatment planning modules/applications may poll one or more buffers for new info at a designated frequency (e.g., every 20 ms).

The details provided via the 6D input application bridge 1610 may be based on a loaded recipe file. In one embodiment, the 6D input application bridge 1610 manages the loading and saving of parameters/recipes for each 6D input device. Also, in one embodiment, application modules such as a 3D virtual space registration module 1690 and a 2D mouse emulation module 1675 are connected with or included in the 6D input application bridge 1610.

The 2D mouse emulation module 1675 receives 6D input position and orientation information from one or both of the optical tracking system and EM tracking system, and converts this data into a 2D format for 2D mouse emulation. This may enable the 6D input devices to also be used to control input for the standard 2D output devices. For example, the signal from the 6D input devices can be mouse emulated with a trajectory fashion to enable a user to select icons, views, treatment planning settings from dropdown windows, etc. in a 2D display region. This may obviate a need to switch between a 6D input device and a 2D input device when interacting with data displayed on the monoscopic display or in a 2D display region of a stereoscopic display.

The 2D mouse emulation module 1675 may transform input data into a 2D trajectory format. In one embodiment, the 2D Mouse emulation mode maintains a transformation matrix that it applies to input received from tracking devices to transform the input into the 2D trajectory format. The 2D trajectory formatted input data may be stored in a 2D mouse emulation buffer by the 6D input application bridge 1610. Therefore, when an application determines that it needs 2D mouse emulation data, it may request the data from the 2D mouse emulation buffer. 2D mouse emulation is described in greater detail above with reference to FIG. 14A.

The monitor space registration module 1690 transforms input data from a virtual space or standard workspace to the CT space. In one embodiment, this is performed when the 6D input application bridge 1610 receives new input data. The new input data is calibrated to the CT space before it is stored in the appropriate buffer or buffers in one embodiment. Alternatively, the monitor space registration module 1690 maintains a transformation matrix (or multiple transformation matrices) for transforming coordinates between the CT space and virtual space (or between the CT space and the standard workspace). When a rendering of the CT volume in the virtual space (or standard workspace) changes (e.g., when the virtual space is rotated, zoomed or panned), the transformation matrix may be updated as described above. An inverse of the new transformation matrix may then be applied to a rendering of a virtual pointer/cursor in the virtual space (or standard workspace) to ensure that the virtual pointer maintains a fixed position relative to the virtual space (or standard workspace) when the rendering of the CT volume is changed.

The above described software architecture 1600 provides for various configurations of 6D input devices in different customer environments.

Treatment Planning Operations in a Virtual Environment

The following sections will introduce examples of several treatment planning operations that can be improved through use of a virtual environment. It should be noted, though, that the virtual environment can also make other treatment planning operations and tasks both easier and more intuitive. Additionally, the skilled artisan will appreciate that most all operations performed in the virtual environment can be applied equally for 3D rendered images displayed as orthographic projections in a standard workspace on a monoscopic display.

In one embodiment, the treatment planning software includes interactive tools and a stereoscopic "at-a-glance" display that allows clinicians to observe and easily respond to feedback throughout the plan generation and optimization process, assuring the desired result is achieved quickly and efficiently. The virtual environment of the treatment planning system is preferably presented via high resolution 3D graphics, which make it possible for clinicians to visualize treatment doses at extremely high resolution, although the skilled artisan will appreciate that other resolutions will suffice to practice embodiments of the present invention. The user interface of the treatment planning software may be organized, for example, into six planning tasks, which may be enhanced via the virtual environment. Each of these planning tasks are listed below, and then described in more detail following the list. Note that the presented order of the tasks is for example only.

(1) LOAD. The user selects and loads patient data.

(2) FUSE. If the user chooses two or more medical images (e.g., different types of image modalities such as CT and PET images) to generate a treatment plan, this task allows the user to fuse, or visualize (e.g., by overlaying or otherwise combining), the images so they are aligned to the same reference frame.

(3) ALIGN. The user sets the treatment modes, identifies fiducials (if any are present), and aligns the nominal patient position within detectors (e.g., x-ray imagers) of an imaging system.

(4) CONTOUR. The user contours anatomical volumes of interest.

(5) PLAN. The user can generate and modify isocentric and non-isocentric plans. The user can also evaluate the dose distribution for the plan.

(6) VISUALIZE/REVIEW. The user can view one or more 3D images of the patient, and a developed treatment plan for the patient. The user can also merge and filter volume renderings of the patient anatomy.

Load Task

The Load task is the first step of the treatment planning software, in accordance with one embodiment of the present invention. In one embodiment, the Load task is performed by plan load module 1510 of FIG. 15. This task allows the user to load previously saved plans, start a new plan by loading DICOM formatted patient data, including volumes of interest pushed as DICOM RT structure sets, recover the last plan worked on, or delete a previously saved plan. The load task may import 3D images from a diagnostic imaging source, for example, magnetic resonance imaging (MRI), positron emission tomography (PET) scans, angiograms and computerized x-ray tomography (CT) scans. These anatomical imaging modalities are able to provide an accurate three-dimensional model of a volume of interest (e.g., skull or other tumor bearing portion of the body) and, thereby, the volume requiring treatment can be visualized in three dimensions.

Figure 17:
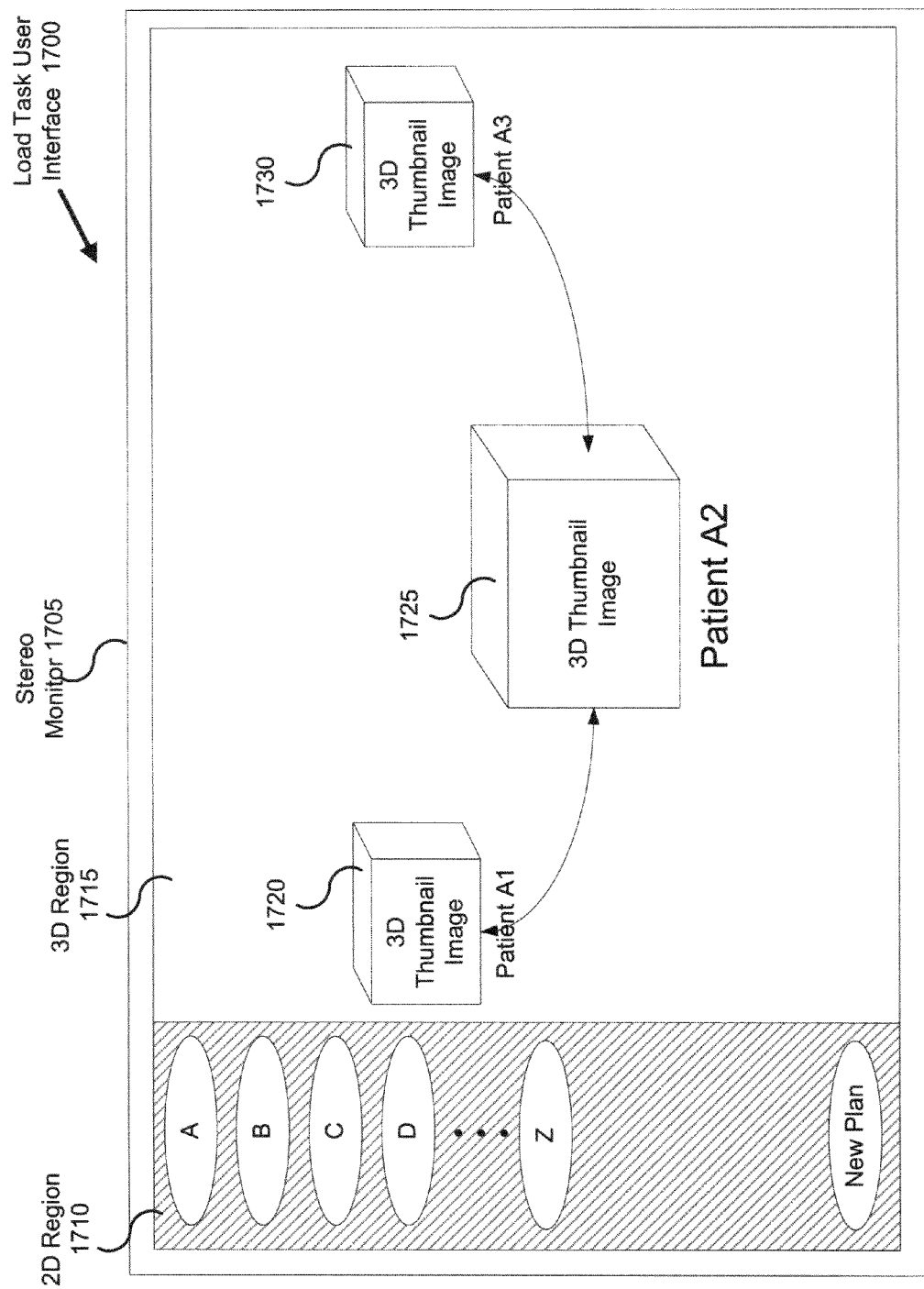
FIG. 17 illustrates a user interface for the Load task in a virtual environment, which may be displayed on a stereoscopic display, in accordance with one embodiment of the present invention.

For exemplary purposes only, the following method of creating a treatment plan using the treatment planning software is described with respect to a newly created plan. FIG. 17 illustrates a user interface for the Load task 1700 in a virtual environment, which may be displayed on a stereoscopic display. The illustrated user interface is just one possible arrangement and visualization of various buttons, tabs, data, etc. The user interface for the Load task 1700 in one embodiment is divided into a 2D region 1710 and a 3D region 1715. Objects are presented two-dimensionally in the 2D region 1710, while objects are presented three-dimensionally in the 3D region 1715. The 2D region may include one or more buttons and/or tabs that are user selectable, which may include buttons corresponding to the letters of the alphabet. Multiple letters may be represented by a single button. For example, the button currently labeled A could instead be labeled A-C. When a button representing one or more letters of the alphabet is pressed, plans for patients whose names begin with the selected letter or letters are shown in the 3D region 1715. In one embodiment, a separate 3D thumbnail image of one or more images included in a plan is shown for each displayed plan. For example, if the button A is pressed, plans for patients A1 1720, A2 1725 and A3 1730 may be shown. The user may use 6D input devices to scroll through the patient plans illustrated in the 3D region 1715. A currently selected patient plan (e.g., patient A2 1725 in FIG. 17) is shown near the center of the 3D region 1715. To the left and right of the currently selected patient plan, patient plans that alphabetically precede and follow the currently selected patient plan may be shown.

The use of multiple image modalities is beneficial for treatment planning. A CT image may be selected because its data is used to track patient movement. MR or PET images may provide improved views of the pathological anatomy compared to CT images. For example, once a particular patient is selected, a list of information and files (not shown) corresponding to that patient may be displayed, either in the 3D region 1715 or the 2D region 1710. The displayed information may include a list of images, which may be represented using virtual artifacts in the 3D region 1715. As with the first image, the user may select a second image by first selecting the patient and one or more additional images.

Fuse Task

With one or more images loaded by the treatment planning software, the next step is to fuse (if desired), or visualize (e.g., by overlaying or otherwise combining) the images together. Alternatively, the next step may correspond to a different task described herein, such as the align task, contour task, etc. In order for the user to contour structures such as the pathological and critical structures, the images are aligned together in a common space so that one image can be overlaid over the other image. Both of the images may be three-dimensional reconstructions when viewed on a stereoscopic display.

Image fusion is a task to help a user register multiple patient images together. Each patient image is a virtual artifact that may be shown in the virtual environment. Registration involves a transformation that maps one or more additional images to a primary CT volume. Once this transformation has been determined and the registration has been completed, the images may be visually fused onto the CT coordinate space, which acts as a common coordinate space for the images. This maximizes the mutual information of two or more loaded images. These images may be of the same or of different image modalities. Image fusion makes it easier to identify anatomical structures based on information provided by each of the individual modalities.

For image fusion, users can load a primary planning CT series (e.g., a CT volume) with diagnostic secondary image series, such as an MRI series, and then register the MRI to the CT using either an intensity-based image registration based on initial seed points or manual registration. Image fusion may be performed manually, automatically, or semi-automatically. Manual image fusion, automatic image fusion and semi-automatic image fusion may all be simplified and improved via a virtual environment. In one embodiment, the image fusion task is performed by fuse module 1520 of FIG. 15.

Manual Image Fusion in a Virtual Environment

Manual fusion performed in a virtual environment can be controlled in 3D virtual space rather than using a set of many 2D image slices. 6D input devices can help acquire and manipulate an object's (e.g., virtual artifact's) position and orientation in the 3D virtual space. The information provided by the 6D input devices (or 3D input devices, 4D input devices or 5D input devices) can be used in registration, transformation, or to modify 3D viewing parameters. Thus, a user can view the immediate result of alignment via the virtual environment as image fusion is being performed. The results of alignment (3D fusion) can be viewed along any cutting plane directions during and after image fusion.

6D input devices can control image translation and rotation along six degrees of freedom. Some 6D input devices (e.g., a data glove) are good at gross motion control, and some 6D input devices (e.g., a 6D mouse) are good at fine motion control. The information passed by 6D input tools will be interpreted as rotation information and translation information. The rotation information and translation information can be applied to a registration matrix between the primary CT volume and the target image being aligned with the CT volume. The rendering of the target image volume will be updated correspondingly.

Figure 18A:
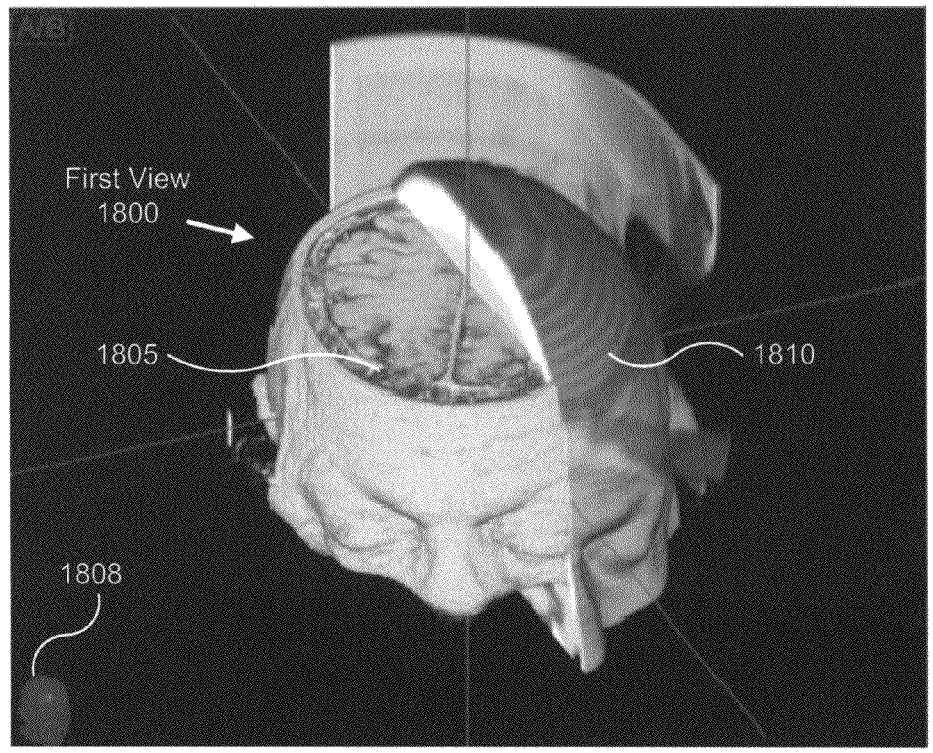
FIGS. 18A and 18B illustrate a first stereoscopic view and second stereoscopic view of digital artifacts in a virtual environment during image fusion.
Figure 18B:
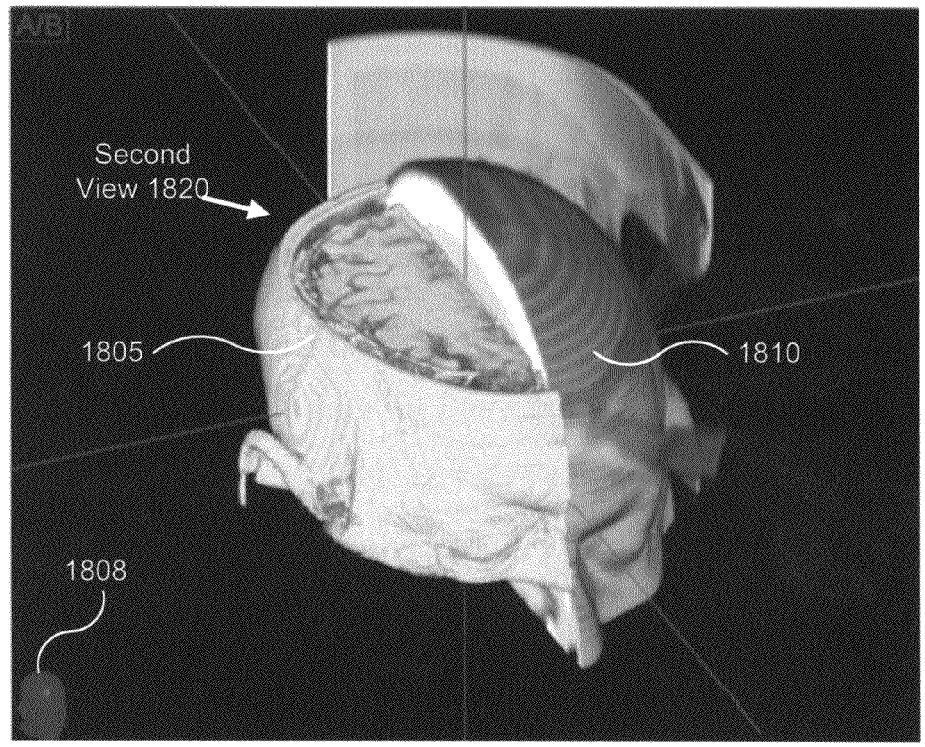

FIGS. 18A and 18B illustrate a first view 1800 and second view 1820 of digital artifacts in a virtual environment during image fusion. A first virtual artifact 1805 that is a simulation of a patient's head based on diagnostic image data from a first image modality (primary CT volume) and a second virtual artifact 1810 that is a simulation of the patient's head based on diagnostic data from a second image modality are shown. At the lower left corner of FIGS. 18A and 18B is a depiction of a head 1808 facing a particular direction. The direction in which the head 1808 faces indicates the reference frame of the primary CT with which the additional image is being fused.

The virtual artifacts 1805, 1810 are shown together using a half-half mode separated by a cutting plane. The cutting plane divides each virtual artifact so that only the portion of the virtual artifact on one side of the cutting plane is visible. Therefore, the portion of the first virtual artifact that is on a first side of the cutting plane is shown, but the portion of the first virtual artifact that is on the opposite (second) side of the cutting plane is not shown. Similarly, the portion of the second virtual artifact that is on the second side of the cutting plane is shown, but the portion of the second virtual artifact that is on the first side of the cutting plane is not shown. As illustrated, in FIG. 18A, the two images are out of alignment by a rotation along the vertical axis.

In FIG. 18B, the two images have been correctly aligned by performing a rotation along the vertical axis. In the manual fusion process, the user can translate or rotate one or both of the images (virtual artifacts) both roughly (with gross changes) and with fine control (with fine changes). This allows the user to align the images correctly near a target position even though they may not be correct in other regions of the images. Note that rotating the primary CT image may cause the entire reference frame to be rotated as well since the CT space may be fixed to the primary CT image. In one embodiment, the user may select a setting that causes the rendering of a secondary image to remain unchanged when the CT image is rotated, repositioned and/or zoomed. If this setting is not selected, rotating the primary CT image will also cause the secondary image to rotate by the same amount.

In summary, by using 6D input information, the user is provided an innovative and intuitive way to manually align two medical image volumes in the 3D stereoscopic virtual workspace of the virtual environment. This manipulation can be more direct, efficient and informative than a 2D fusion routine.

Figure 18C:
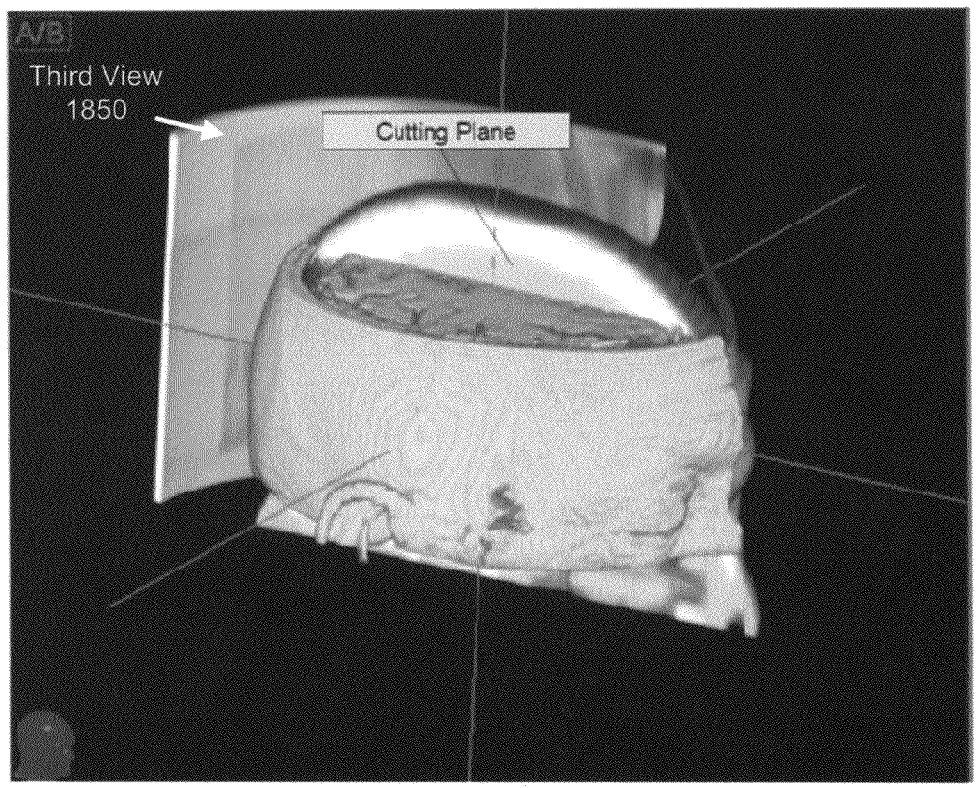
FIG. 18C illustrates a third stereoscopic view of a virtual environment showing two fused images in a half-half display mode.

FIG. 18C illustrates a third view 1850 of a virtual environment showing two fused images in the half-half mode described above. As shown, a cutting plane is used to visualize both images, and the relationship between the images. In one embodiment, a source image volume (first three-dimensional simulation of a patient anatomy) and target image volume (second three-dimensional simulation of the patient anatomy) are rendered together in the 3D stereoscopic virtual space in the half-half mode so as to be separated by the cutting plane. By using the input of 6D input tools, a user may modify the orientation and position of the cutting plane. The user may then review the image information in the region where the two image volumes are merged together to confirm the alignment accuracy of the image fusion.

Automatic Image Fusion in a Virtual Environment

Automatic and semi-automatic image fusion use algorithms and/or models to align two different virtual artifacts (e.g., two images of the same patient anatomy). By initiating a register or fuse command, the image registration/fusion is performed (either automatically or semi-automatically). The images may be fused by employing a matrix algebra solution that performs an initial alignment of the two images based on an initial placement of one image over the other. The user may then have the treatment planning software perform a refinement process after the initial register/fuse step. The treatment planning software may also execute an algorithm to improve the alignment of the two images. During the refinement process, the user can manipulate the split views (e.g., shown in the half-half mode in FIG. 18C) to evaluate the quality of the fusion.

There are multiple ways to do automatic or semi-automatic image fusion, but most of them require a user to identify an initial seed position or positions to reduce a searching space. The closer the initial seed positions are to the final alignment, the smaller the searching space may be. In one embodiment, the initial position is identified by the user by performing a brief manual fusion, as described above. The manual fusion may be very rough, and may be used to simply let the automatic fusion algorithms start the automatic registration process. 6D input devices may be used to perform gross motion control to roughly align images in the virtual environment. Automatic or semi-automatic fusion operations may then be performed. Alternatively, a user may select one or more points on each of the images shown in the 3D virtual space. Fusion may then begin by first aligning the two images along the selected point or points. The points may be chosen along the surface of the images or at a location within the shown volume of the images.

After the automatic registration process, a 6D input device can be used to fine tune the fused images manually. For example, for a spine study, the CT image is obtained with the patient lying in one particular position, and the MR image is obtained with the patient lying in a different position. Because the images were obtained using different positions, the automatic fusion process may not be possible, or may be error prone, because it is difficult to match the two images together rigidly.

The above described auto fusion enables users to register two image series automatically using 6D input devices, such as a glove device, to grasp the 3D volume of a secondary image and then drop it onto the 3D volume of the primary planning CT in the 3D virtual space. The initial registration from the 6D input device's input may be input to an intensity-based image registration. This may simplify the designation of initial seed points, and automate the fusion task in an intuitive manner.

Align Task

After fusion of images is completed, the next step is to establish parameters that describe the treatment to be performed on the patient. The first parameter may be the total number of fractions in the treatment. In radiosurgery, the overall treatment is typically divided into a set of steps instead of giving the patient the entire radiation dose in one session. This is referred to as fractionation. For example, the incidental treatment dose may be divided over five treatment fractions, because there may be critical structures adjacent to the pathological anatomy that may not be able to tolerate the total radiation dose if performed in one fraction. By dividing the treatment into multiple fractions, the critical regions that may be exposed to radiation are given time to recover and heal prior to the next fraction. Depending on the dose delivered to the critical structures, it may not be necessary to divide the treatment into multiple fractions, which may depend upon both the quality of the treatment plan and the ability to accurately and precisely deliver the treatment plan. The user is allowed to define the number of fractions, for example, by typing in a number or incrementing or decrementing the number of fractions.

In one embodiment, the next parameters that the user may set, in sequence, are Treatment Anatomy and Template Path Set. Treatment Anatomy informs the treatment planning and delivery system of the general anatomical area (e.g., head) to be treated. Path Set defines the set of positions for the robotic arm (e.g., robotic arm 4052 or other treatment delivery modality, e.g., gantry) from which to activate the radiation beam from the LINAC. The treatment planning software may provide a number of templates with different sets of beam positions, depending on the treatment anatomy selected.

In one embodiment, the next parameter that the user may set is a Tracking Method option. Tracking Method (e.g., 6D_Skull) defines how the imaging system automatically takes diagnostic x-ray shots of the patient while the patient is being treated, and the treatment delivery system uses the data from the resulting x-ray images to determine the position of the patient during treatment, allowing the robot to make adjustments in case the patient and/or target moves during treatment. This ability to track during treatment is unique to the Cyberknife® System, but is not limited to such a system.

It should also be noted that the treatment planning parameters setting user interface may be a stereoscopic virtual interface shown in the virtual environment via a stereoscopic display. Alternatively, the interface may include a first portion shown in a monoscopic display and a second portion shown in a stereoscopic display of the virtual environment.

During treatment delivery, the machine center should be aligned with the CT image so that the imaging system may function correctly. This is accomplished by defining the CT image center and the position of the patient during treatment. In one embodiment, the position of the patient on the treatment couch is used to define the CT center. Cross-hairs may be moved by the user to adjust the CT center of the patient. As the user moves the CT center, the Current CT Center Point coordinates will appear in the control view.

In one embodiment, the user must confirm the CT center before the user can proceed to the Contour and Plan Tasks. If the coordinates have been confirmed, the coordinates appear in a Confirmed CT Center Point table. The confirmed coordinates may also be graphically shown in the 3D view of the virtual environment. By aligning the machine center with the CT center, the treatment delivery and imaging systems can produce the desired images (e.g., x-ray images) of the patient during treatment when the patient is properly aligned with the treatment delivery system.

Contour Task

The next task of treatment planning is creating and modifying anatomical volumes of interest (VOI). This task includes two steps: Delineate and Set Properties. The Delineate step includes drawing tools for the user to draw and edit volumes of interest. The Set Properties step allows the user to change specific tags and display settings associated with each volume of interest. The volume of interest (VOI) is a user-defined region overlain on the medical images that typically represents a distinct anatomical feature such as the pathological anatomy targeted for treatment or critical structures to avoid radiation. For example, using a 3D stereoscopic (or volumetric) image in the virtual environment, the user identifies and designates the pathological anatomy as the target region by drawing or contouring a volume around the pathological anatomy. This process may be performed separately for the pathological anatomy and any critical structures.

Volume of interest structures may include target regions and critical regions. A target region is a volume of interest structure to which radiation is directed for therapeutic or surgical purposes. A critical region is a volume of interest structure for which radiation treatment is avoided. For example, a CT slice of a spinal region may include a pathological anatomy (e.g., tumor, legion, arteriovenous malformation, etc.) target region to be treated and an adjacent normal anatomy (e.g., internal organ) critical region to be avoided.

A VOI (also referred to as a contour) inside an object volume (e.g., inside of a CT volume) is defined as a geometry object. In radiosurgery applications, for example, tumor and critical structures can be defined as a volume of interest based on the patient image, such as CT or MRI. There are different ways to render VOI information on top of volume information. In one embodiment, an embedded geometry rendering may be used, which uses a surface rendering technique to render the embedded geometry information into the volume rendering image. In an alternative embodiment, VOI information may be rendered on top of volume information by converting the VOI geometry to special volume information before the rendering. The VOI and volume information may be rendered in the virtual environment by using a volume rendering method at the same time.

The treatment planning software enables the generation of a critical region contour around a critical region and a target region contour around a pathological anatomy. Conventionally, a user manually delineates points along many 2D slices of a patient anatomy to generate contours. While this may seem an easy task, such delineation can be difficult due to the three-dimensional nature and irregularities of the pathological and normal anatomies. Moreover, the user may need to designate the contour along many slices, which can be a time consuming process.

Manual Contour Generation

In one embodiment of the present invention, contouring of complex volumes of interest (VOIs) is facilitated with the use of drawing and segmentation tools in a virtual environment. Lesions and critical structures of all sizes—large, small or odd shaped—can be contoured in relatively small periods of time in comparison to conventional methods.

As mentioned above, in a traditional treatment planning environment, a user would delineate a collection of 2D planes or slices, which were typically cardinal planes (e.g., sagittal, axial, coronal, etc.). Thus, the user needs to page through the slices, and draw the VOI contour on each of the slices one by one. In a virtual environment, on the other hand, and in accordance with embodiments of the present invention, using 6D input devices, a user can manually contour a volume of interest (VOI) in the 3D stereoscopic virtual space of the virtual environment directly. Alternatively, the user may manipulate the volume in the 3D stereoscopic virtual space (e.g., by rotating, panning, zooming, etc.) to identify oblique slices that can have any orientation (e.g., that do not align with any of the cardinal planes). The user may then contour on the oblique slices.

Using 6D tracking input tools, a user may trace the VOI contour in the virtual space (or on the oblique slices). When drawing directly in 3D virtual space, a user has more options and increased control in the process of contouring. A user drawing on oblique slices also has increased options and control in the process of contouring. Both the direct contouring in 3D virtual space and the contouring on user defined oblique slices can save much time spent generating a treatment plan, especially when users encounter cases which have complex and irregular shape structures. For example, one type of VOI that is difficult to contour is a blood vessel. Blood vessels can go in any direction, and can be relatively small and very difficult to see in the cardinal 2D slices (e.g., sagittal, axial, coronal, etc. slices). In the 3D virtual space of a virtual environment (e.g., as presented on a stereoscopic display), however, blood vessels can be much easier to see and delineate.

For example, referring back to FIG. 1A, contour 40 is manually delineated in the virtual environment 2 based on user input. User 30 moves an electronic pointer 35 from a starting location 74 to an ending location 76 along a motion path while the user presses a button on the electronic pointer which activates a bumper tool. Positional sensor 5 tracks the electronic pointer 35 in a positional sensor reference frame 10 as the electronic pointer 35 moves through the motion path 70, and sends position data to a computing device (not shown). The computing device transforms the position data to a virtual space reference frame 25 of the stereo monitor 20, and generates the contour 40 in the virtual space 15. The computing device continually updates a rendering of the contour 40 and a virtual pointer 50 as the position data is received.

Figure 19:
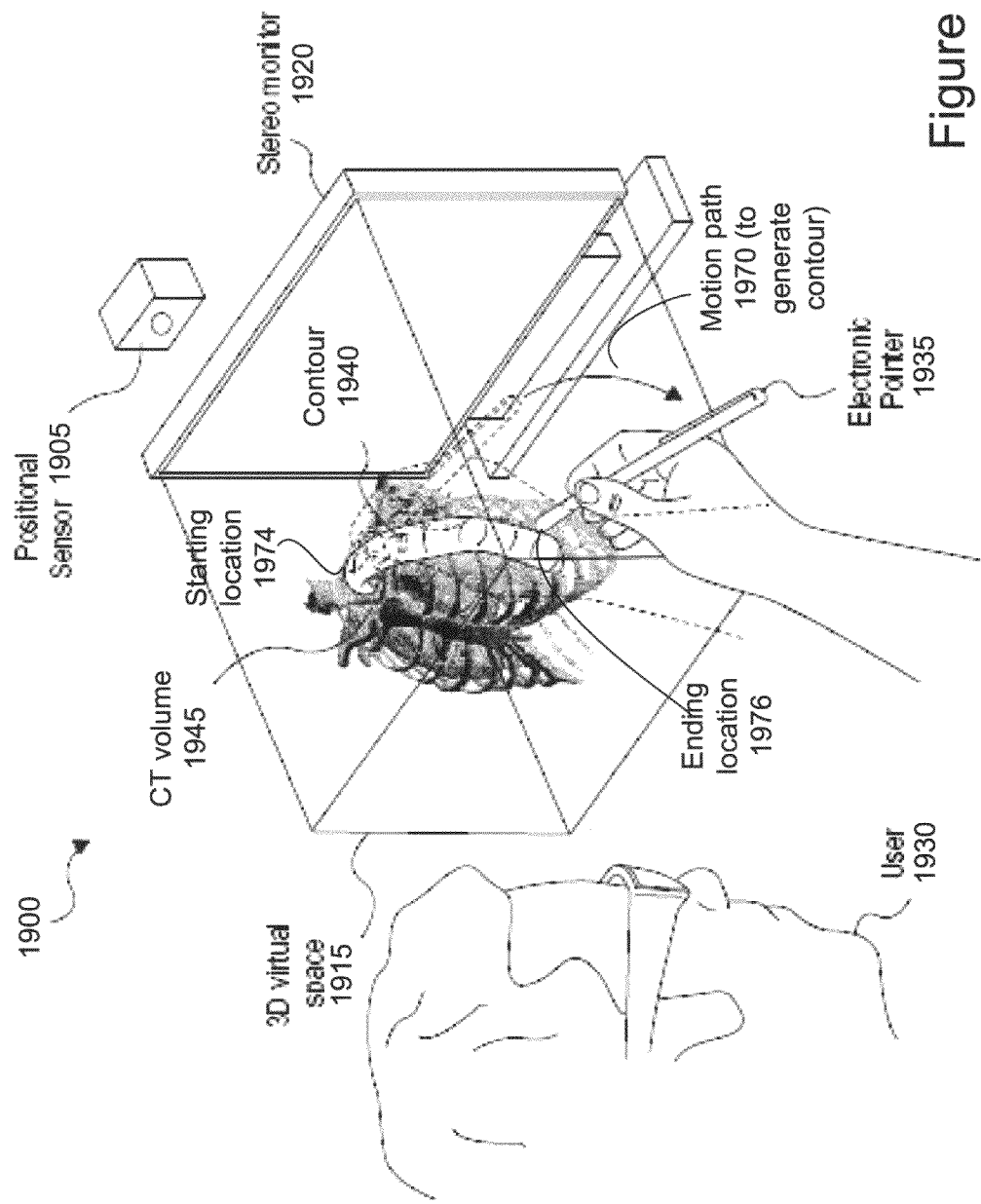
FIG. 19 illustrates another example of a user generating a contour via a virtual environment, in accordance with one embodiment of the present invention.

FIG. 19 illustrates another example of a user 1930 generating a contour 1940 via a virtual environment 1900. The virtual environment 1900 includes a 3D stereoscopic (or volumetric) virtual space 1915 that includes a CT volume 1945. The 3D stereoscopic virtual space (including the CT volume 1945) are presented by a stereo monitor 1920 (or alternatively a volumetric display). In FIG. 19, the user 1930 moves an electronic pointer 1935 from a starting location 1974 to an ending location 1976 via a motion path 1970. In contrast to the example shown in FIG. 1A, however, the starting location 1974 and ending location 1976 are perceived by the user to be inside the stereoscopic virtual space 1915 presented by the stereo monitor 1920. In one embodiment, the electronic pointer 1935 includes haptic feedback, increasing the realism that that user is actually interacting with a physical torso that is represented by CT volume 1945.

Figure 20A:
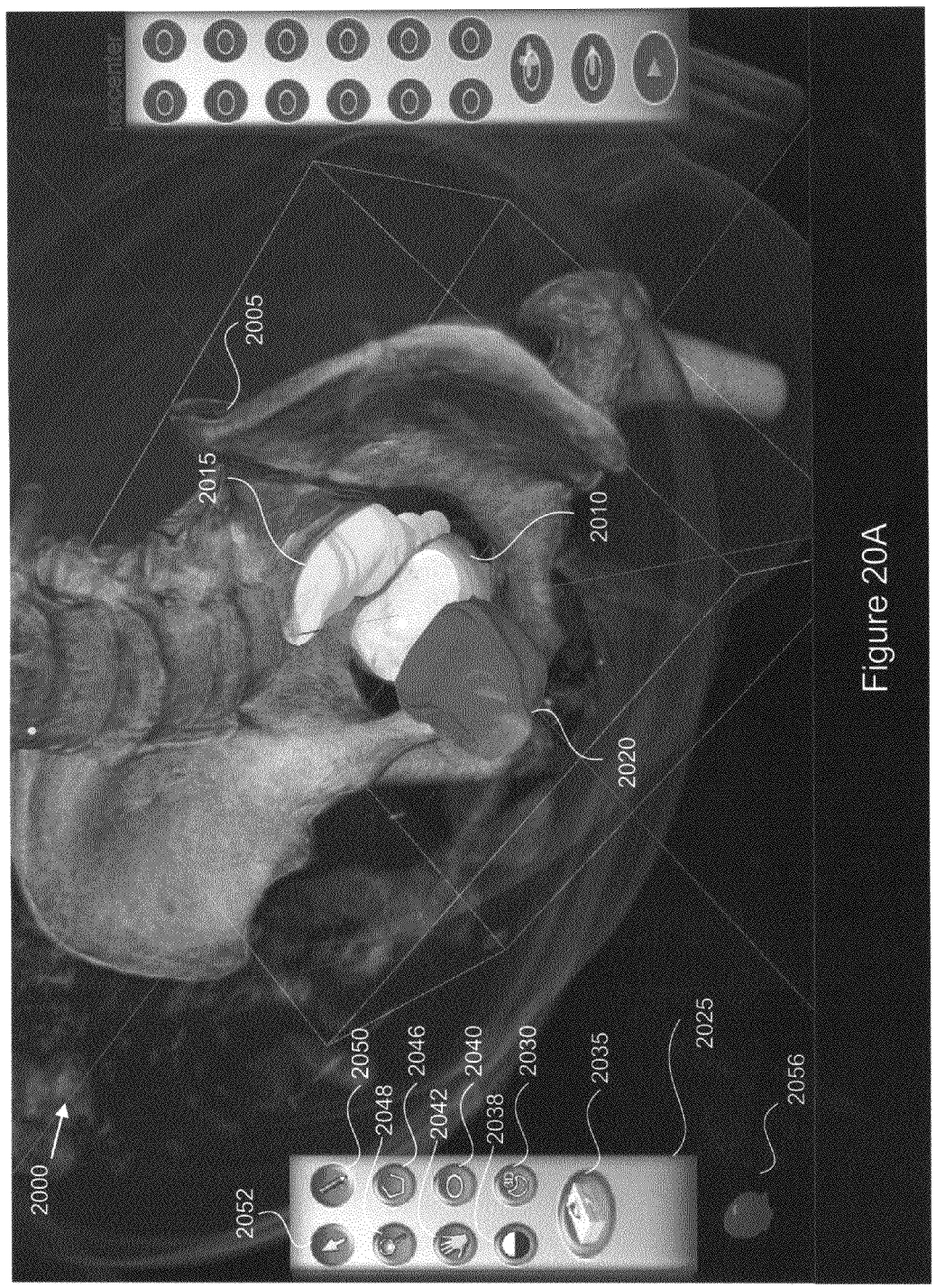
FIG. 20A illustrates a user interface for the contour task as displayed in a stereoscopic display of a treatment planning system, in accordance with one embodiment of the present invention.

FIGS. 20A and 20B illustrate a user interface for the contour task as displayed in a treatment planning system that includes a stereoscopic display (or volumetric display) and a monoscopic display, in accordance with one embodiment of the present invention. FIG. 20A illustrates the user interface of the contour task in the stereoscopic display, while FIG. 20B illustrates the user interface of the contour task in the monoscopic display. The treatment planning system may include the stereoscopic display and the monoscopic display side by side, such that the user can see both user interfaces simultaneously.

FIG. 20A includes an example stereoscopic (or volumetric) user interface 2000 for the contour task, which shows a 3D stereoscopic (or volumetric) virtual space that includes a CT volume 2005, a target region 2010, and two critical structures 2015 and 2020. FIG. 20B includes an example monoscopic user interface 2058 that shows one or more views 2060, 2062, each of which may also include the CT volume 2005, target region 2010 and critical structures 2015, 2020. Each view 2060, 2062 may include an orthographic projection of the images in the stereoscopic virtual space onto a plane or a 2D slice of the images shown in the stereoscopic virtual space. The orthographic projections may have the same perspective as that of the 3D stereoscopic virtual space shown in the 3D stereoscopic user interface 2000, or may have different perspectives (e.g., be from different viewing angles, different pan settings and/or different zoom settings). The 2D slices may be taken from a cardinal view of the CT image (e.g., a coronal, sagittal, or axial views). Alternatively, one or more 2D slices may be taken of an oblique view. The oblique view is a 2D view along any plane (not just the cardinal views). The user can choose the plane along which the oblique view is shown, for example, by selecting a cutting plane in the 3D virtual space. The cutting plane may be rotated about any axis and panned in any direction. The user can then contour on the oblique slice (e.g., draw a 2D shape in the plane shown in the oblique view) using a drawing tool. In one embodiment, if the user wishes to retain the same oblique view point, but wishes to reposition the cutting plane along a vector normal to the cutting plane, this can be performed using a scroll in/out command (e.g., via a mouse wheel of a 2D mouse).

Each of the CT volume 2005, target region 2010 and critical structures 2015, 2020 may be virtual artifacts rendered in the 3D stereoscopic virtual space. Delineation of the target region 2010 and critical structures 2015, 2020 facilitates inverse planning by independently identifying the target region 2010 and the critical structure 2015, 2020. During inverse planning, volume of interest (VOI) structures corresponding to the target region 2010 and critical structures 2015, 2020 are used to distinguish between structures to be targeted or avoided with respect to the administered radiation dose. That is, the radiation source is positioned to localize the radiation dose into a volume that conforms as closely as possible to the target region 2010 intended for radiation treatment, while avoiding exposure of the nearby critical structures 2015, 2020 and other healthy tissue.

The VOIs may be updated in real-time in the 3D virtual space on a stereoscopic display as the VOIs are delineated. The virtual environment provides users a comprehensive perception of an overall image volume of patient anatomies and VOI position. Additionally, the stereo and/or volumetric 3D rendering delivers better depth information than standard monoscopic monitors, which will help a user make more accurate judgments in the delineation task.

In one embodiment, the contour task includes a 3D drawing palette 2025 for delineating VOIs (e.g., 2010, 2015, 2020) in the 3D virtual space 2000 and a 2D drawing palette 2028 for delineating VOIs in one of the views 2060, 2062. The 3D drawing palette 2025 and 2D drawing palette 2028 may each include standard drawing tools such as a pen tool 2050, polyline tool 2046, and oval tool 2040. The pen tool 2050 is a freehand drawing tool that enables random shapes to be drawn. The polyline tool 2046 enables continuous line segments to be drawn, and the oval tool 2040 enables circular and oval shapes to be drawn. These drawing tools can be used to draw shapes and contours in the views of the monoscopic user interface 2058 and directly in the 3D virtual space of the stereoscopic user interface 2000.

In one embodiment, the 3D drawing palette 2025 and 2D drawing palette 2028 include a 3D bumper tool 2030. The 3D bumper tool 2030 provides a 3D virtual object (e.g., a sphere, ellipse, square, triangle, etc.) that can draw 3D structures and manipulate (change the shape of) existing 3D structures. The change in shape of a 3D structure is dependent on the shape and size of the 3D bumper. In one embodiment, both the shape and size (e.g., radius) of the bumper can be user selected. The bumper tool 2030 is capable of making both rough and fine changes to a 3D structure.

Figure 21:
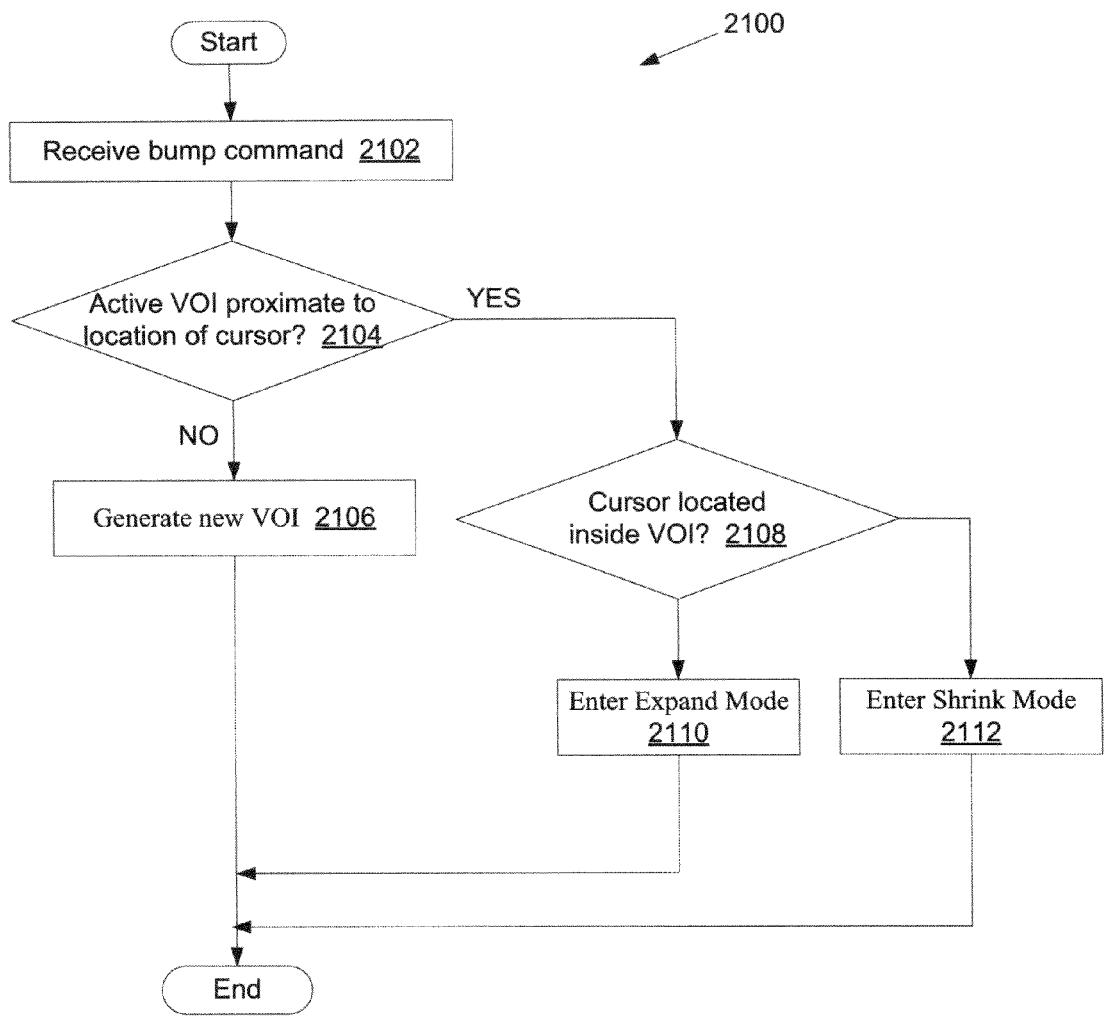
FIG. 21 illustrates a flow diagram of one embodiment for a method of performing a 3D bumper tool operation during treatment planning, in accordance with one embodiment of the present invention.

FIG. 21 illustrates a flow diagram of one embodiment for a method 2100 of performing a 3D bumper tool operation during treatment planning, in accordance with one embodiment of the present invention. The method is performed by processing logic that comprises hardware (e.g., circuitry, dedicated logic, programmable logic, microcode, etc.), software (such as instructions run on a processing device), or a combination thereof. In one embodiment, method 2100 is performed by the computing device 105 of FIG. 1B. Method 2100 is performed in one embodiment once a 3D bumper tool has been selected from a drawing palette (while a 3D bumper tool is active).

Referring to FIG. 21, at block 2102 of method 2100, the computing device receives a bump command. The bump command may be generated by a user pressing a button of a 6D input device, of a 2D mouse, etc. For example, a bump command may be issued whenever a user presses a specific button of an electronic pointer.

At block 2104, upon receiving the bump command, the computing device determines whether there is an active VOI proximate to a location of a cursor in 3D virtual space. In one embodiment, an active VOI is any VOI that has been previously generated. In another embodiment, an active VOI is a specific VOI or VOIs that have been user selected. In a 3D virtual space, the cursor may be a 3D cursor such as a virtual pointer. If the cursor is proximate to an active VOI, the method continues to block 2108. Otherwise, the method continues to block 2106.

At block 2106, the computing device generates a new VOI. The new VOI in one embodiment has the dimensions and shape of the selected bumper tool. For example, if the selected bumper tool is a sphere with a radius of 30 pixels, then the VOI will initially be a sphere with a radius of 30 pixels. Note that in one embodiment the bumper tool size is calibrated to the virtual space, however, contours generated by the bumper tool are calibrated to the CT space. Therefore, the size of a contour generated using the bumper tool may be dependent upon a zoom setting of the virtual space. For example, a bumper tool size of 5 pixels may be equivalent to 3 mm in the CT space when zoomed in, or 30 mm in the CT space when zoomed out.

As a user moves a 6D input device, so long as the bump command remains active (e.g., the button remains depressed), the shape of the generated VOI is updated, similar to a volumetric version of a draw command in a standard image editing program. For example, if the user draws an egg shape while the bump command is active, then the VOI will have an egg shaped volume. An example of a contour being generated using the bumper tool is shown in FIGS. 1A and 19.

Returning to FIG. 21, at block 2108, the computing device determines whether the cursor (pointer) is located within the active VOI in the 3D virtual space. If the cursor is located within the active VOI, the method proceeds to block 2110. If the cursor is not located within the active VOI, the method proceeds to block 2112. In one embodiment, a visual indication is provided as to whether the cursor is inside or outside of an active VOI. For example, the VOI may be displayed using a first color if the cursor is inside of the VOI and a second color if the cursor is outside of the VOI.

At block 2110, an expand bumper tool mode is entered. While the expand bumper tool mode is active, when the cursor is moved against the surface of the VOI, the VOI is expanded based on an interaction of the bumper tool shape with the VOI.

At block 2112, a shrink bumper tool mode is entered. While the shrink bumper tool mode is active, when the cursor is moved against the surface of the VOI, the VOI is dented/shrunk based on an interaction of the bumper tool shape with the VOI. Thus, the bumper tool can be used to change a shape of the active VOI. The method then ends.

Returning to FIGS. 20A and 20B, in one embodiment, VOIs can be interpolated between two or more drawn 2D or 3D structures. Once two or more 2D or 3D structures have been drawn (in the 3D virtual space or in views of the 2D user interface 2058), using an interpolate operation, the computing device can then combine the two or more shapes into a single VOI by interpolating the space between the shapes. The computing device then interpolates the region between the two drawn shapes to delineate the structure when the interpolate command is issued.

Automatic and Semi-Automatic Contour Generation

In addition to the manual contour delineation described above, automatic and semi-automatic segmentation may be performed to delineate contours. One such semi-automatic segmentation that may be used is a Smart Curve Fitting option 2064. The Smart Curve Fitting option 2064 is a contouring algorithm that can be used in conjunction with pen, line, ellipse, and bumper drawing tools. For example, the user first draws a line around a target to create an initial contour using a pen tool (for example), or a volume around a target to create an initial contour using the 3D bumper tool. If used with a drawn 2D structure, the smart curve fitting algorithm will reshape the line around the target to fit the boundary based on the contrast within the display in the plane in which the structure was drawn. If used with a drawn 3D structure, the smart curve fitting algorithm will reshape the volume around the target to fit the 3D boundaries of the target based on the contrast, intensity, or other values of the regions included in the 3D structure. In one embodiment, the user designates approximate boundaries of the target, and the smart curve fitting algorithm finds the appropriate surface of the target automatically. This allows the user to draw a less than perfect line and/or volume around the target during the initial stage of contouring.

Additional specialized semi-automatic segmentation tools for delineating contours for specific structures may also be provided. In one embodiment, specialized semi-automatic segmentation tools are provided for generating contours for a lung 2066, skin 2068, spine 2070, and ball or cube shaped target 2072 (e.g., an eyeball), as shown in FIG. 20B. Based on an interaction of a user with the data displayed in the 3D virtual space via a 6D input device, these semi-automatic segmentation tools can greatly simplify the generating of contours for these structures. In one embodiment, when a semi-automatic segmentation tool is selected, a user selects a seed point at the target, and the tool searches for a structure having a given set of properties. For example, if the lung semi-auto segmentation tool is selected, the tool will search the area around the selected seed point for changes in intensity or other characteristics that distinguish the lung from other structures.

In one embodiment, semi-automatic segmentation tools use adaptive thresholding (otherwise known as local thresholding) to determine the borders of a target structure. A critical structure or target structure can have distinct variations of the intensity distribution throughout the structure and the surrounding areas. To account for the intensity distribution that may be present in a single structure, adaptive thresholding adaptively determines multiple thresholds to use throughout the structure.

Adaptive thresholding may be performed by estimating the signal to noise ratio (SNR) of a local region to its surrounding background, and determining an intensity threshold value for segmenting this local region based on the SNR. For example, for each pixel, the surrounding pixels (e.g., that represent surrounding tissues) are used to determine what threshold to set for the pixel. In one embodiment, an intensity distribution is determined for a 5×5 grid centered at the pixel in question. Other grids, such as a 7×7 grid, 9×9 grid, 5×8 grid, etc. may also be used. A SNR ratio of intensity for the 5×5 grid (or other sized grid) can then be estimated from the intensity distribution, and an intensity threshold can be set for the pixel in question based on the SNR. The intensity threshold for that pixel can then be used to differentiate between the background and the region of interest at that pixel. Therefore, for each pixel a separate threshold can be determined and used to identify whether the pixel is part of the background or the region of interest.

Some semi-automatic segmentation may require that only a single seed point be selected. Other semi-auto segmentation tools may require that multiple actions be taken by the user (e.g., multiple seed points be selected). The following example shows how a spine VOI is designated and delineated using the semi-automatic spine segmentation tool 2070, in accordance with one embodiment of the present invention. In another embodiment, semi-automatic spine delineation may be performed by selecting a single seed point. The below example illustrates some advantages of delineation in a virtual environment.

Figure 22:
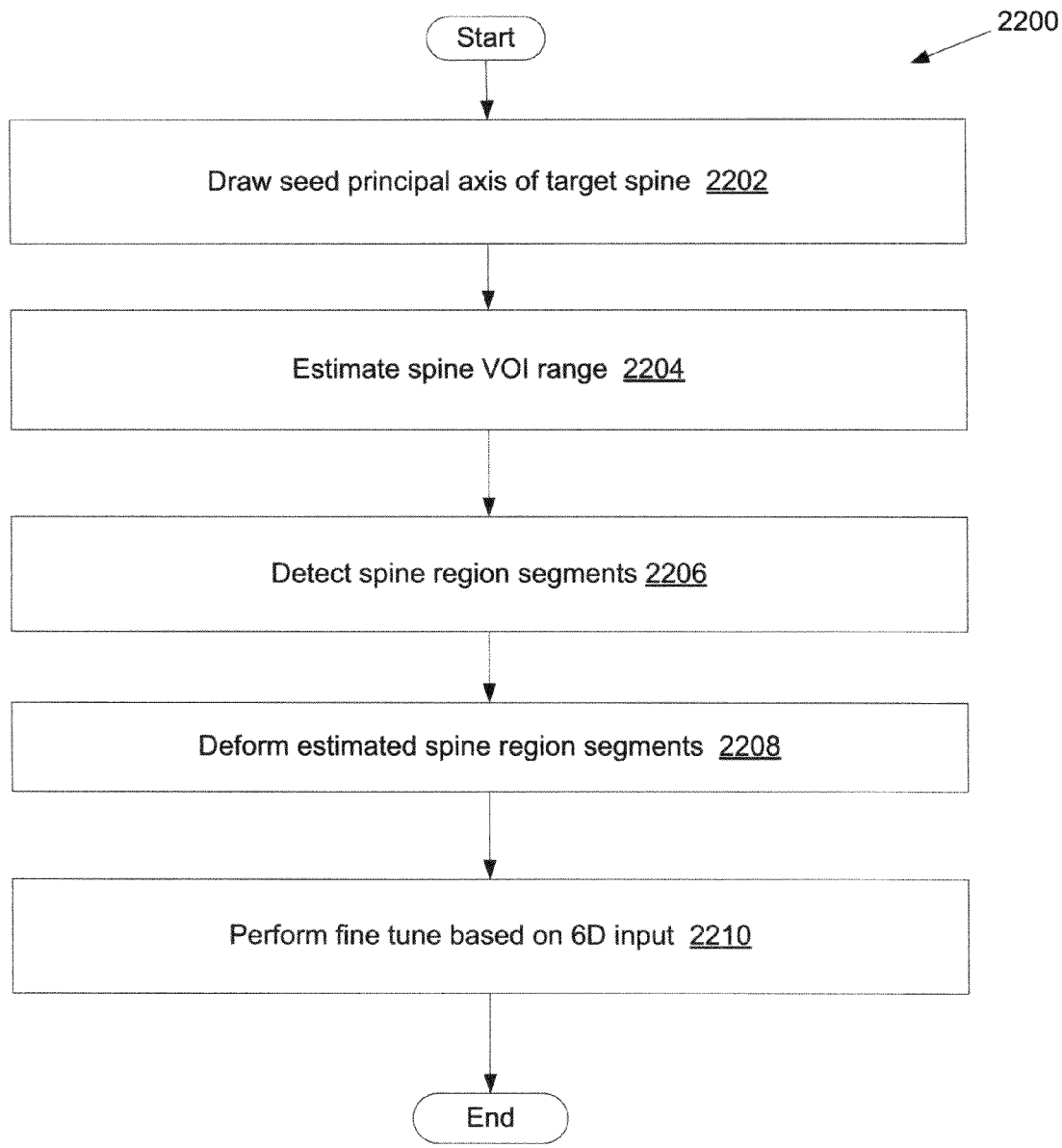
FIG. 22 illustrates a flow diagram of a method for performing VOI delineation for a spine in a virtual environment, in accordance with one embodiment of the present invention.

FIG. 22 illustrates a flow diagram of a method 2200 of performing VOI delineation for a spine in a virtual environment, in accordance with one embodiment of the present invention. Method 2200 includes an accurate, fast and easy to use algorithm for 3D spine VOI detection and delineation for spine cancer radiosurgery. The 3D spine VOI detection and delineation is performed in a full 3D sense by using 6D input devices and 3D computer imaging techniques. The method 2200 is performed by processing logic that comprises hardware (e.g., circuitry, dedicated logic, programmable logic, microcode, etc.), software (such as instructions run on a processing device), or a combination thereof. In one embodiment, method 2200 is performed by the computing device 105 of FIG. 1B.

Referring to FIG. 22, at block 2202 of method 2200 a seed principal axis of a target spine is drawn in 3D virtual space based on input from a 6D input device. The user may be asked to draw a simple line along the length of an illustrated spine to designate the seed principal axis. Once the user draws the line, the line may be used to determine the principal axis, which may be graphically illustrated in the 3D virtual space.

At block 2204, a computing device estimates a spine VOI range with the defined seed principle spine axis. The VOI range may be determined using features included in a CT volume that includes the spine (e.g., by differentiating between image colors, intensities, etc.). The VOI range may also be determined using prior patient knowledge, such as patient height, length of spine, etc.

Figure 23:
FIG. 23 illustrates a spine VOI that has been delineated, in accordance with one embodiment of the present invention.

At block 2206, adaptive thresholding techniques are used to detect spine region segments in the estimated spine VOI of the CT volume. At block 2208, the computing device deforms the estimated spine VOI to the detected spine regions by using constraints of the spine surface smoothness and curvature. At block 2210, the deformed spine VOI is fine tuned or edited based on user input from the 6D input devices as necessary to cover all the critical structures. The method then ends. The proposed methods and algorithms can be expected to accurately detect and delineate a 3D spine VOI from CT volumetric images with very high speed. FIG. 23 illustrates a spine VOI that has been delineated using method 2200, in accordance with one embodiment of the present invention.

Figure 24A:
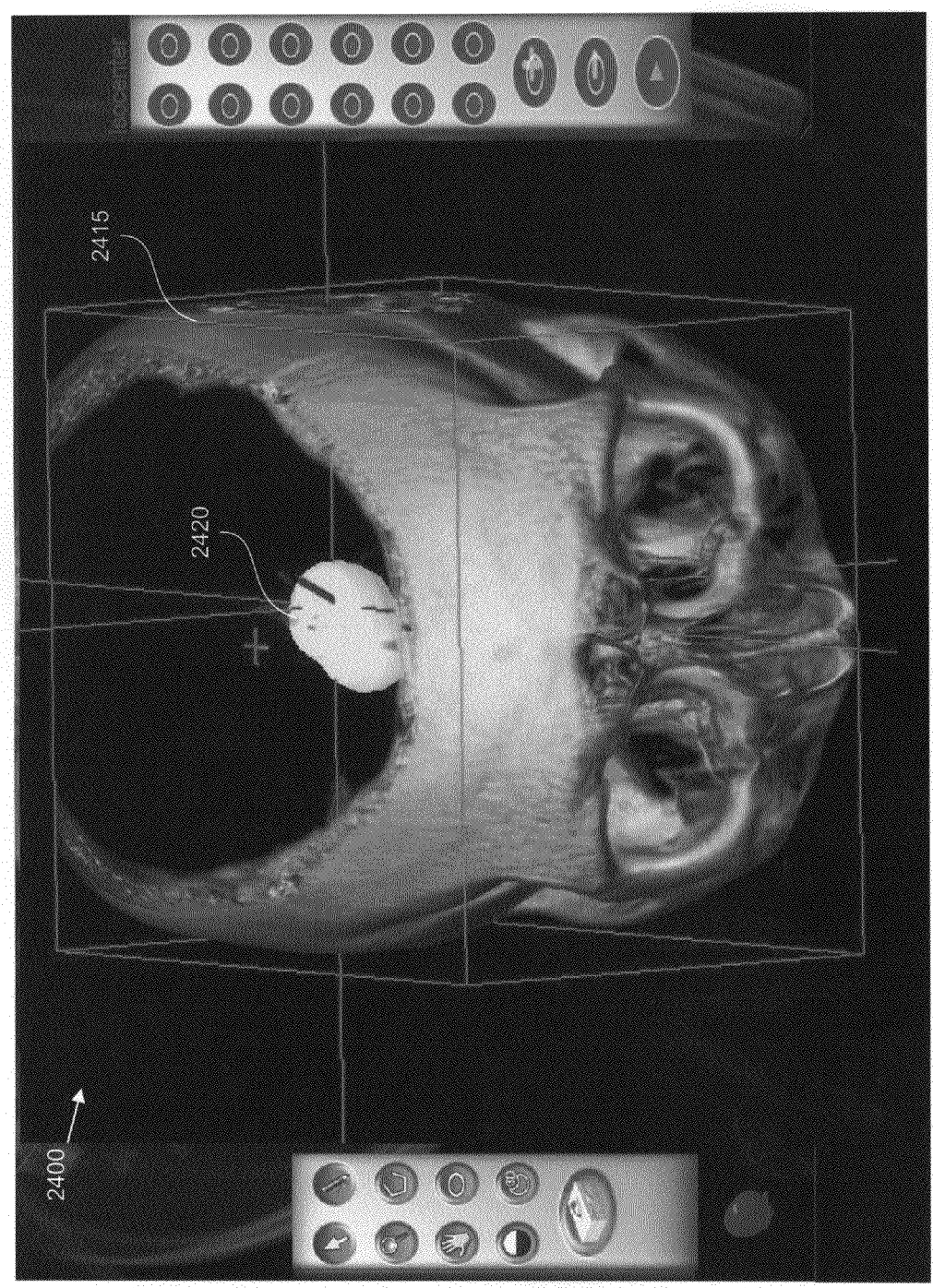
FIG. 24A illustrates a user interface for the contour task as displayed in a stereoscopic display of a treatment planning system, in accordance with one embodiment of the present invention.
Figure 24B:
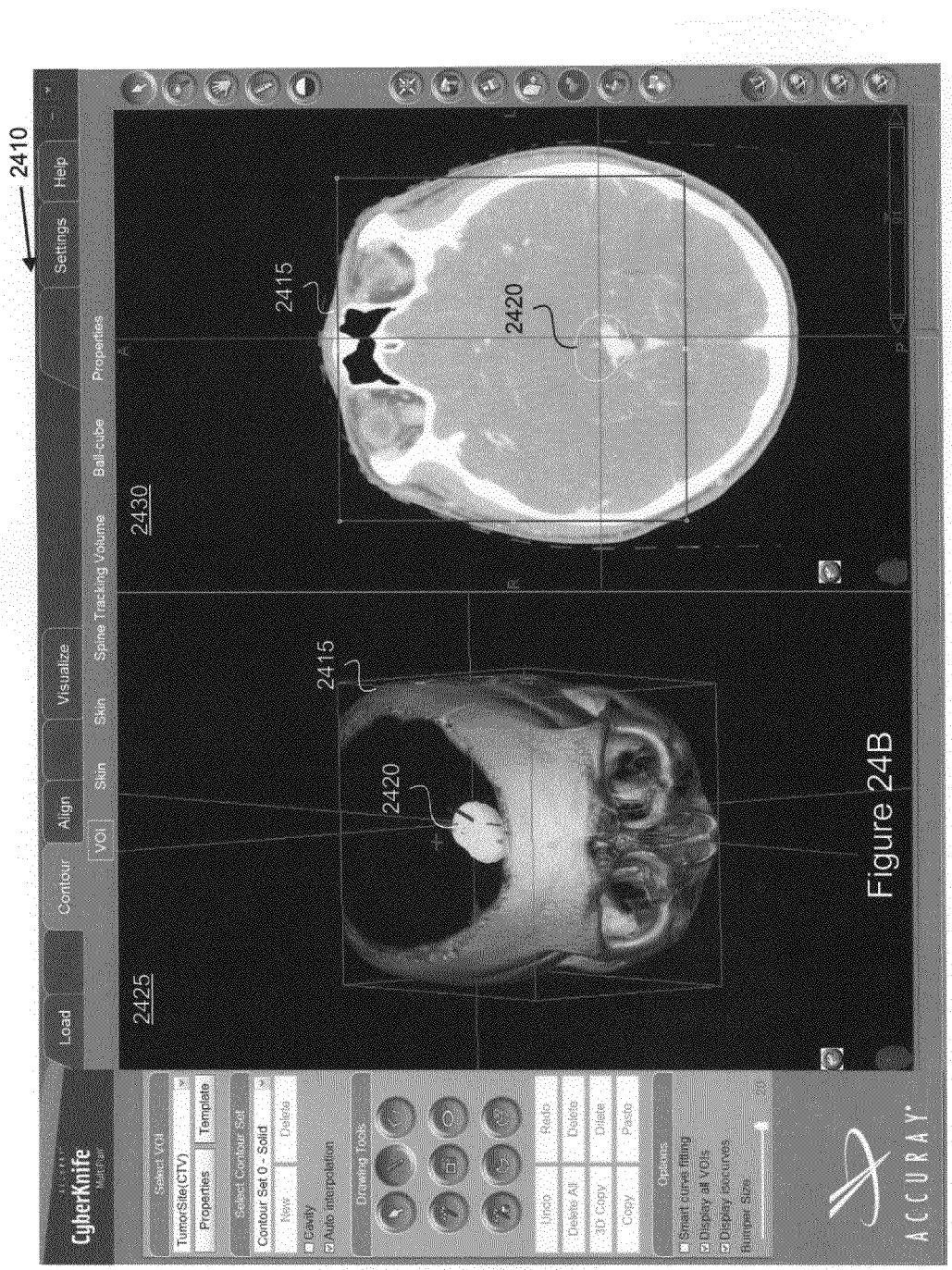
FIG. 24B illustrates a user interface for the contour task as displayed in a monoscopic display of a treatment planning system, in accordance with one embodiment of the present invention.

FIGS. 24A and 24B illustrate a 3D stereoscopic user interface 2400 and a monoscopic user interface 2410 for the contour task, respectively, in which a CT volume 2415 is of a patient skull, and where a single contour 2420 has been delineated. As shown, the monoscopic user interface 2410 includes two views. A first view 2425 reflects the image shown in the 3D stereoscopic user interface 2400, and a second view shows a horizontal slice of the CT volume 2415.

Figure 25A:
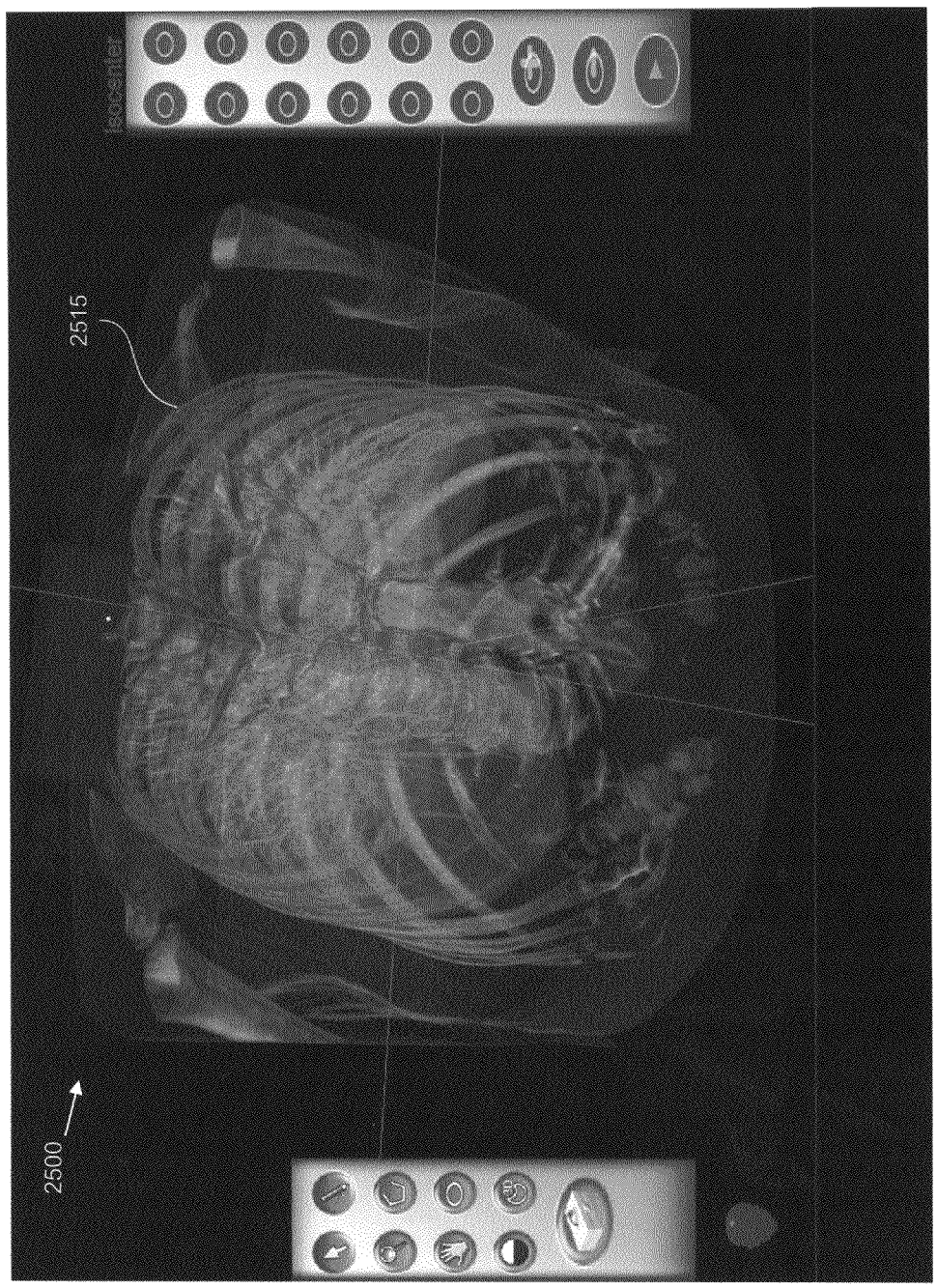
FIG. 25A illustrates a user interface for the contour task as displayed in a stereoscopic display of a treatment planning system, in accordance with another embodiment of the present invention.
Figure 25B:
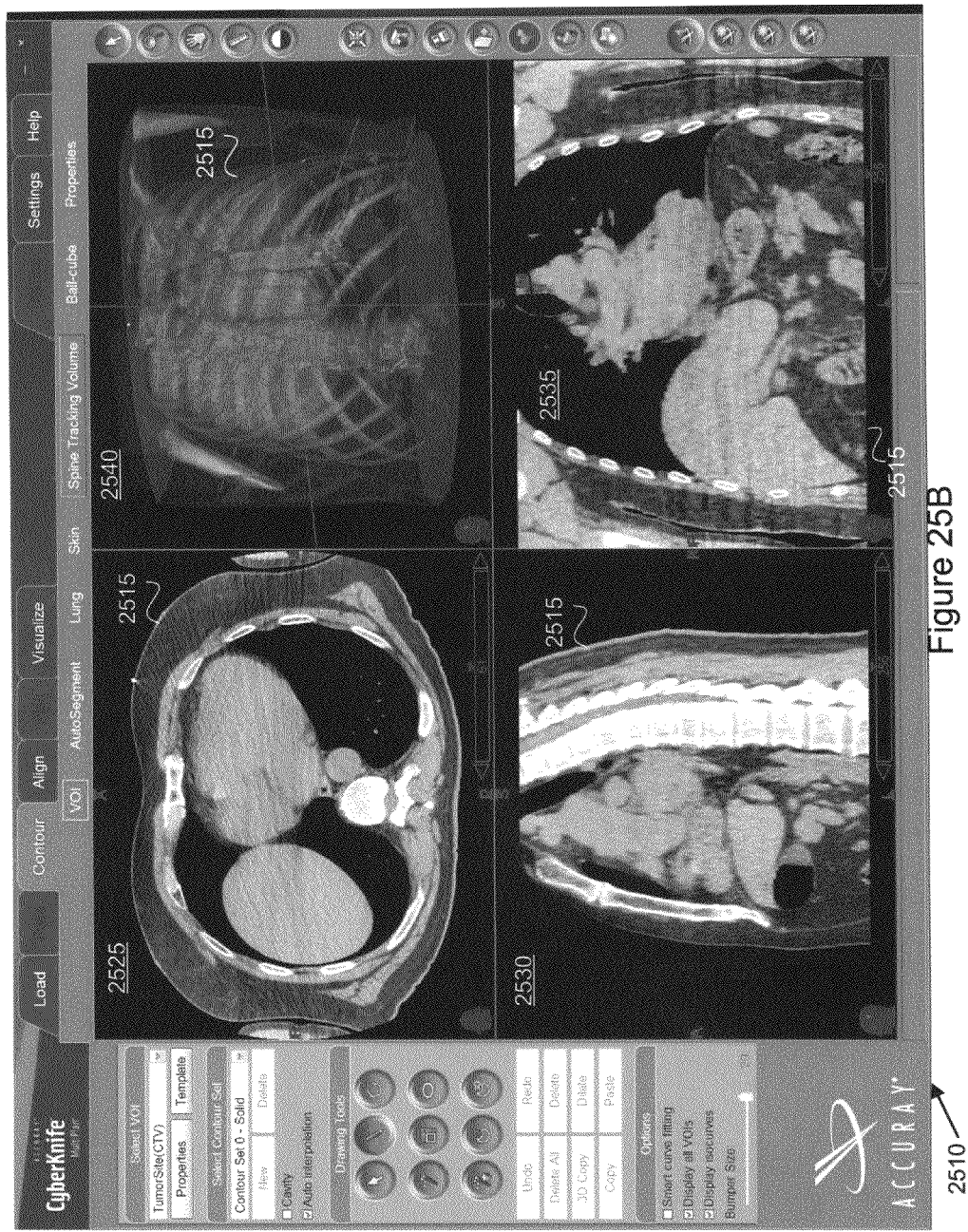
FIG. 25B illustrates a user interface for the contour task as displayed in a monoscopic display of a treatment planning system, in accordance with another embodiment of the present invention.

FIGS. 25A and 25B illustrate a 3D stereoscopic user interface 2500 and a monoscopic user interface 2510 for the contour task, respectively, in which a CT volume 2515 is of a patient torso, and where no contours have yet been delineated. As shown, the monoscopic user interface 2510 includes four views. A first view 2525 shows an axial slice of the CT volume 2515, a second view 2530 shows a sagittal slice of the CT volume 2515, a third view 2535 shows a coronal slice of the CT volume 2515, and a fourth view 2540 shows an orthographical view of the CT volume at a different viewing angle than is shown in the stereoscopic user interface 2500.

Model Based and Atlas Based Contour Generation

Model based contour generation and atlas based contour generation are based on pre-generated contours that are derived from previous treatment plans. In model based and atlas based contour generation, the user may specify a type of anatomy and/or body region that he is attempting to contour. The user may then be presented with a list of pre-generated contours for that type of anatomy and/or that region. The user may select a pre-generated contour that most closely matches an anatomy that he wishes to contour. The user may then place the pre-generated contour over the anatomy in the 3D virtual space using 6D input devices. Once placed, the pre-generated contour may be moved, resized and shaped until it matches the underlying anatomy that it is meant to represent. Such moving, resizing and shaping may be performed manually in the 3D virtual space, or may be performed automatically or semi-automatically.

Plan Task

The Plan task contains the functionality for creating, refining, and reviewing treatment plans. In one embodiment, the plan task is performed by plan development module 1530 of FIG. 15. The treatment planning software supports forward treatment planning (e.g., isocentric treatment planning), inverse treatment planning (e.g., conformal treatment planning), mixed forward/inverse treatment planning and sequential planning methods to treat lesions throughout the body. In one embodiment, with one or both of two distinct planning optimization algorithms (e.g., iterative and non-iterative), the treatment planning software assures that clinicians can maximize the unparalleled flexibility of the treatment planning system.

In one embodiment, forward treatment planning is used for generating an isocentric treatment plan. In forward treatment planning, a medical physicist determines the radiation dose (an isocenter or dose sphere) to be applied to a tumor and then calculates how much radiation will be absorbed by critical structures (i.e., vital organs) and other healthy tissue. Isocentric planning is a type of forward treatment planning. For isocentric planning, all the beams carry an equal weight of monitor unit (Mu) of dose. Therefore, there is no independent control of dose levels for a given number of beams, because the volumetric energy density at any given distance from the isocenter is a constant, no matter where the isocenter is located.

In another embodiment, inverse planning is used for generating a treatment plan such as a conformal treatment plan. In inverse planning, in contrast to forward planning, the medical physicist specifies the goals and constraints (e.g., such as minimum dose to the tumor and the maximum dose to other healthy tissues), and the treatment planning software then selects the direction, distance, and total number and energy of the beams in order to achieve the specified goals and conditions. One conventional treatment planning system that utilizes inverse planning is the On-Target™ Treatment Planning System produced by Accuray, Inc. of California.

During inverse planning, a volume of interest (VOI) is used to delineate structures to be targeted or avoided with respect to the administered radiation dose. That is, the radiation source is positioned in a sequence calculated to localize the radiation dose into a VOI that, as closely as possible, conforms to the tumor requiring treatment, while avoiding exposure of nearby healthy tissue. Once the target (e.g., tumor) VOI has been defined (see contour operation), and the critical and soft tissue volumes have been specified (see contour operation), the responsible radiation oncologist or medical physicist specifies the minimum radiation dose to the target VOI and the maximum dose to normal and critical healthy tissue. The software then produces the inverse treatment plan, relying on the positional capabilities of the radiation treatment system, to meet the min/max dose constraints/requirements of the treatment plan. Conformal treatment planning is a type of inverse treatment planning.

Figure 26A:
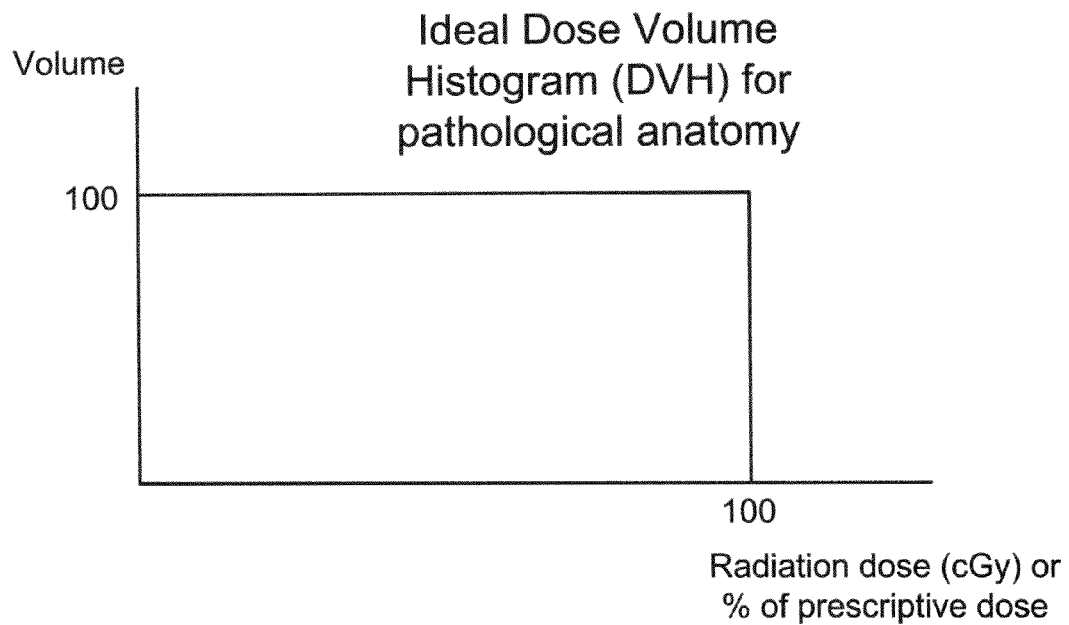
FIG. 26A illustrates an ideal DVH profile for a pathological anatomy, in accordance with one embodiment of the present invention.
Figure 26B:
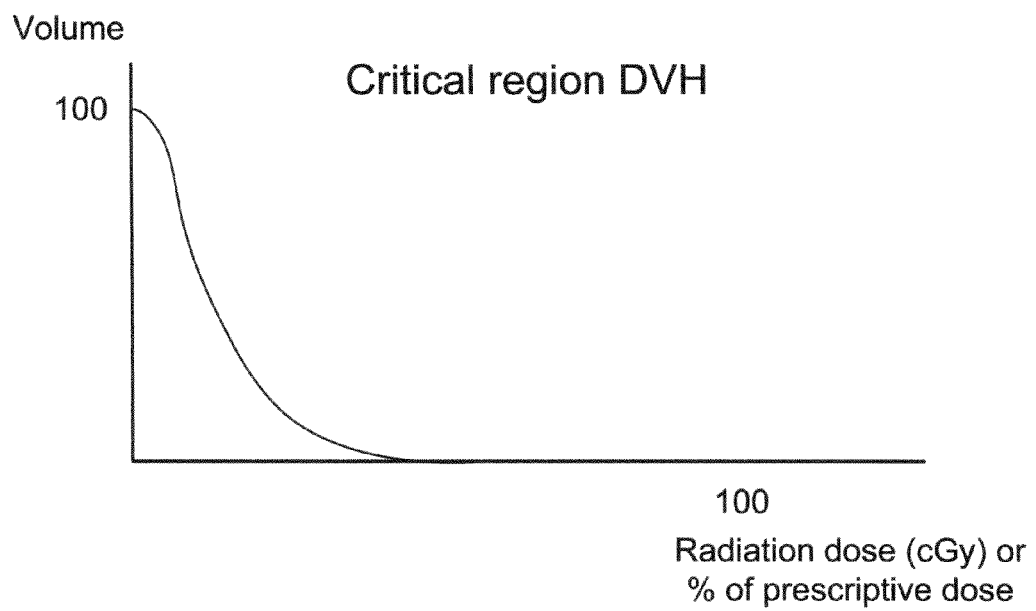
FIG. 26B illustrates a desirable DVH profile for a critical region, in accordance with one embodiment of the present invention.

The two principal requirements for an effective radiation treatment plan are homogeneity and conformality. Homogeneity is the uniformity of the radiation dose over the volume of the target (e.g., pathological anatomy such as a tumor, lesion, vascular malformation, etc.) characterized by a dose volume histogram (DVH). An ideal DVH for the pathological anatomy would be a rectangular function as illustrated in FIG. 26A, where the dose is 100 percent of the prescribed dose over the volume of the pathological anatomy and zero elsewhere. A desirable DVH for a critical region would have the profile illustrated in FIG. 26B, where the volume of the critical anatomical structures receives as little of the prescribed dose as possible.

Conformality is the degree to which the radiation dose matches (conforms to) the shape and extent of the target (e.g., tumor) in order to avoid damage to critical adjacent structures. More specifically, conformality is a measure of the amount of prescription (Rx) dose (amount of dose applied) within a target VOI. Conformality may be measured using a conformality index (CI)=total volume at >=Rx dose/target volume at >=Rx dose. Perfect conformality results in a CI=1.

The first step of the Plan task is defining certain parameters that will be used in the treatment planning process. One parameter that may be used is density model, which reflects the modeling of the radiation absorption by the tissue. Depending on the type of tissue being exposed to radiation, the plan should account for how the CT intensities map into absorption coefficients of radiation. For example, the homogenous model is selected for the cranial region because the tissue is fairly consistent. The homogenous model treats dark intensity regions as air so no radiation is absorbed, and everything else as one type of tissue, which is a fair assumption of the cranial region (i.e., the brain). Other predefined models that are available include lung standard and body standard.

Figure 27A:
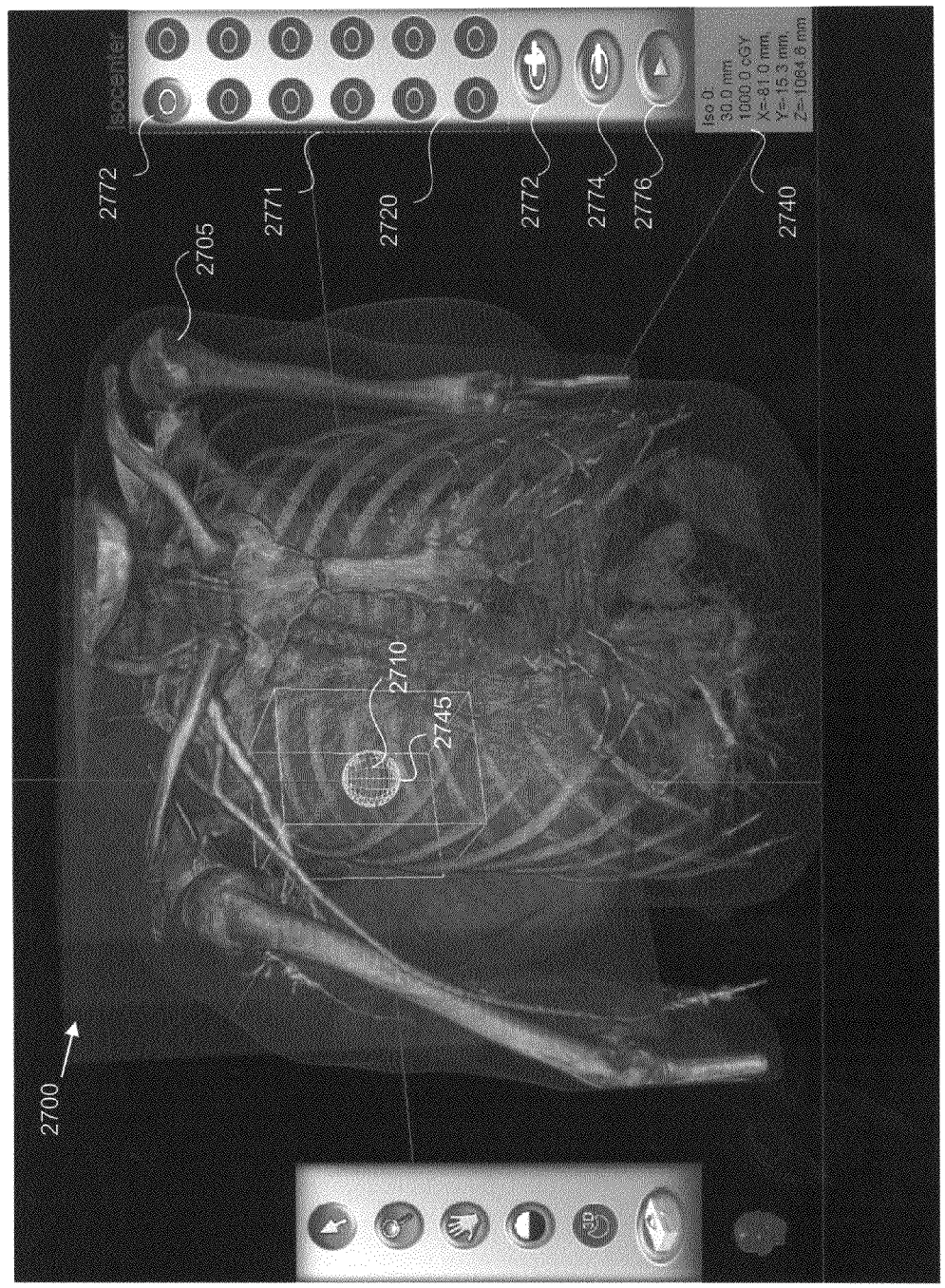
FIG. 27A illustrates a user interface for the plan task as displayed in a stereoscopic display of a treatment planning system, in accordance with one embodiment of the present invention.
Figure 27B:
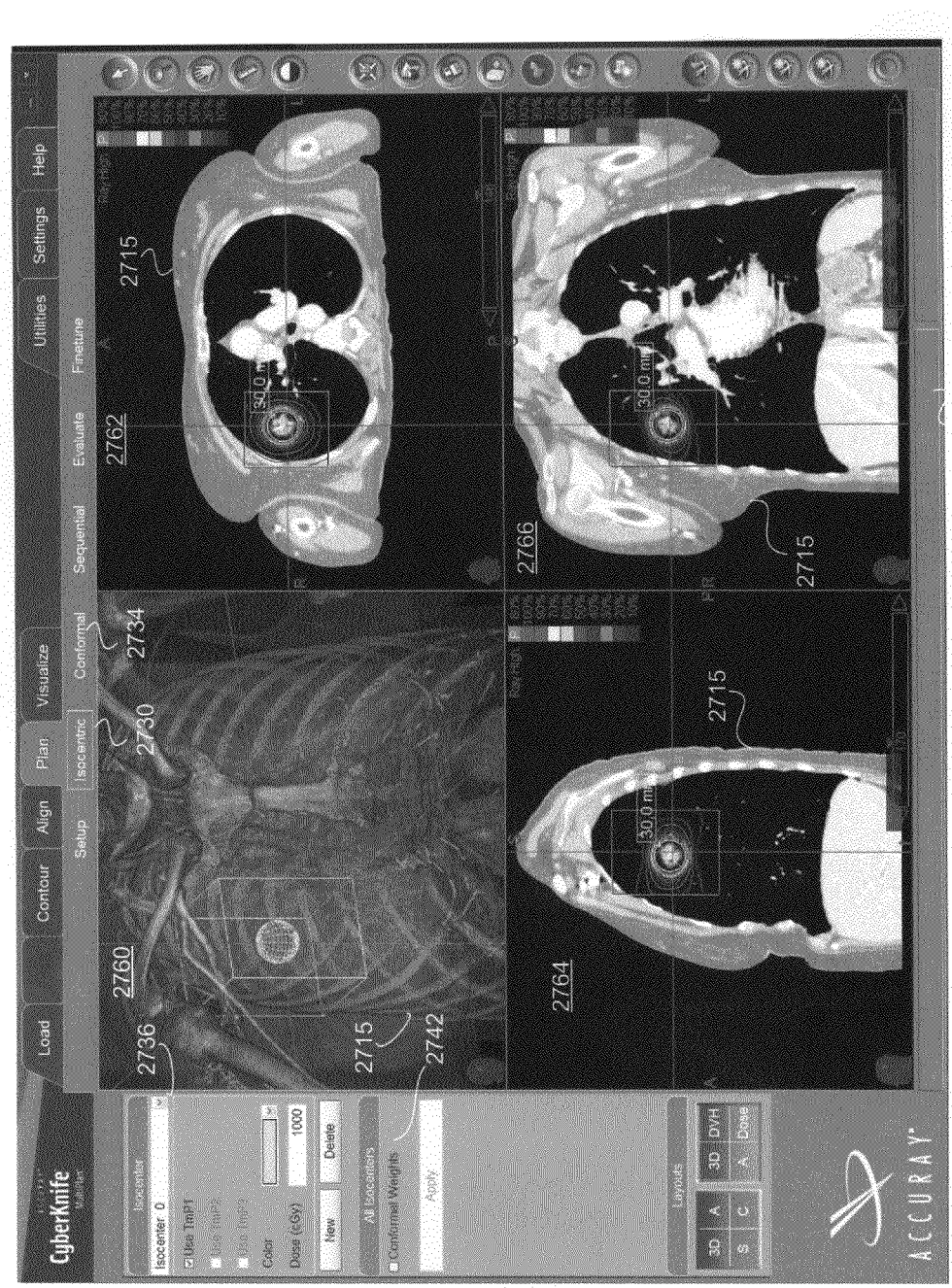
FIG. 27B illustrates a user interface for the plan task as displayed in a monoscopic display of a treatment planning system, in accordance with one embodiment of the present invention.

FIGS. 27A and 27B illustrate a user interface for the plan task as displayed in a treatment planning system that includes a stereoscopic display and a monoscopic display, in accordance with one embodiment of the present invention. FIG. 27A illustrates the user interface of the plan task in the stereoscopic display, while FIG. 27B illustrates the user interface of the plan task in the monoscopic display. The treatment planning system may include the stereoscopic display and the monoscopic display side by side, such that the user can see both user interfaces simultaneously.

FIG. 27A includes an example 3D stereoscopic user interface 2700 for the plan task, which shows a 3D virtual space that includes a CT volume 2705 and a target region 2710. FIG. 27B includes an example monoscopic user interface 2758 that shows a first view 2760, second view 2762, third view 2764 and fourth view 2766 of a CT volume. First view 2760 includes an orthographical visualization the CT volume 2715. Second view 2762, third view 2764 and fourth view 2766 show an axial slice, sagittal slice, and coronal slice, respectively, of the CT volume 2715.

Via the 3D stereoscopic user interface 2700 and/or monoscopic user interface 2710, an isocentric planning option 2730 or a conformal planning option 2734 may be selected. In the embodiment illustrated in FIGS. 27A and 27B, the isocentric planning option 2730 has been selected. FIGS. 28 and 29 (described below), show a stereoscopic user interface 2900 and monoscopic user interface 2910 for the plan task, in which the conformal planning option 2734 has been selected.

Forward Planning in a Virtual Environment

FIGS. 27A and 27B illustrate one embodiment of a forward planning user interface (e.g., for isocentric planning) shown on a stereoscopic display, and a monoscopic display, respectively. In isocentric planning, multiple beams are directed to a single target, forming a dose sphere. The size of the sphere may depend on the collimator size, and in one embodiment, the collimator may have a diameter of about 30 millimeters as measured at about 800 millimeters from the radiation source. To treat a target pathological anatomy, multiple dose spheres may be superimposed on each other in an attempt to obtain a contour that closely matches the shape of the pathological anatomy. Isocentric planning may be best applied when treating a pathological anatomy that has a substantially spherical shape.

In one embodiment, a pull-down menu 2736 provides a listing of all the current isocenters. The selected isocenters become active and are shown in color (e.g., in yellow) on the 3D images and 2D images, and their properties 2740 may also be displayed on the stereoscopic display and/or monoscopic display. Isocenters may be created, resized, moved, or deleted from the user interfaces shown in FIGS. 27A-27B. The user interfaces also allow for the changing of an isocenter's properties, such as dose (cGy), color, and path sets. In one embodiment, aspects of inverse planning may be integrated with forward planning. For example, by checking the Conformal weights box 2742, the beam geometry (i.e., the target and collimator size of the beam set) will be created with isocentric planning, but the weights of the beams will be assigned later during conformal planning.

Isocentric planning uses a forward planning technique to place beams in the radiotherapy treatment planning process. An isocenter palette 2720 is provided for placing and editing isocenters directly in the 3D stereoscopic virtual space. Without a virtual environment, users would normally select an isocenter with its desired dosage to place in 2D axial/sagittal/coronal slices, and then adjust a size of the isocenter in the 2D slices. The virtual environment, on the other hand, allows users to place isocenters described above directly in the 3D stereoscopic (or volumetric) virtual workspace using 6D input devices, such as a data glove or electronic pointer and tracking system, along with the isocenter palette 2720.

The isocenter palette 2720 includes an isocenter list 2771. The isocenter list 2771 shows symbols for all isocenters that have been placed for a selected treatment plan. In the illustrated embodiment, only a single isocenter 2745 has been placed, so only one isocenter symbol 2772 is shown in the isocenter list 2771, and is presently active. To identify that the isocenter 2745 is active, the isocenter symbol 2772 is highlighted in green, and the isocenter 2745 is displayed in the 3D virtual space using a colored (e.g., yellow) wireframe sphere. A status bar 2740 displays information on an active isocenter. The status bar 2740 indicates an identifier for the active isocenter, a collimator size (in mm), a dose (in cGY), and a center of the isocenter (in the CT reference frame).

The isocenter palette 2720 further includes a new isocenter button 2772. When the new isocenter button 2772 is selected, a new isocenter may be generated at a cross hair position (e.g., position of a cursor). New isocenters may be generated with a default collimator size and dose. The isocenter palette 2720 further includes a delete isocenter button 2774, which deletes an active isocenter. The isocenter palette 2720 further includes a play (calculate) button 2776, which generates beams for all existing isocenters included in the isocenter list 2771, and performs dose calculations based on the generated beams. Once all isocenters are placed and sized appropriately, the user may click on a calculate/play button 2776 to view a 3D dose cloud with the 3D tumor volume and the CT image volume.

Users may use an electronic pointer along with the isocenter palette 2720 to generate and place an isocenter with a desired size and dosage. In one embodiment, users may also use an electronic glove device to grasp the isocentric sphere 2745 to adjust its size by opening and/or closing their hand from a palm to a fist and vice versa.

Figure 27C:
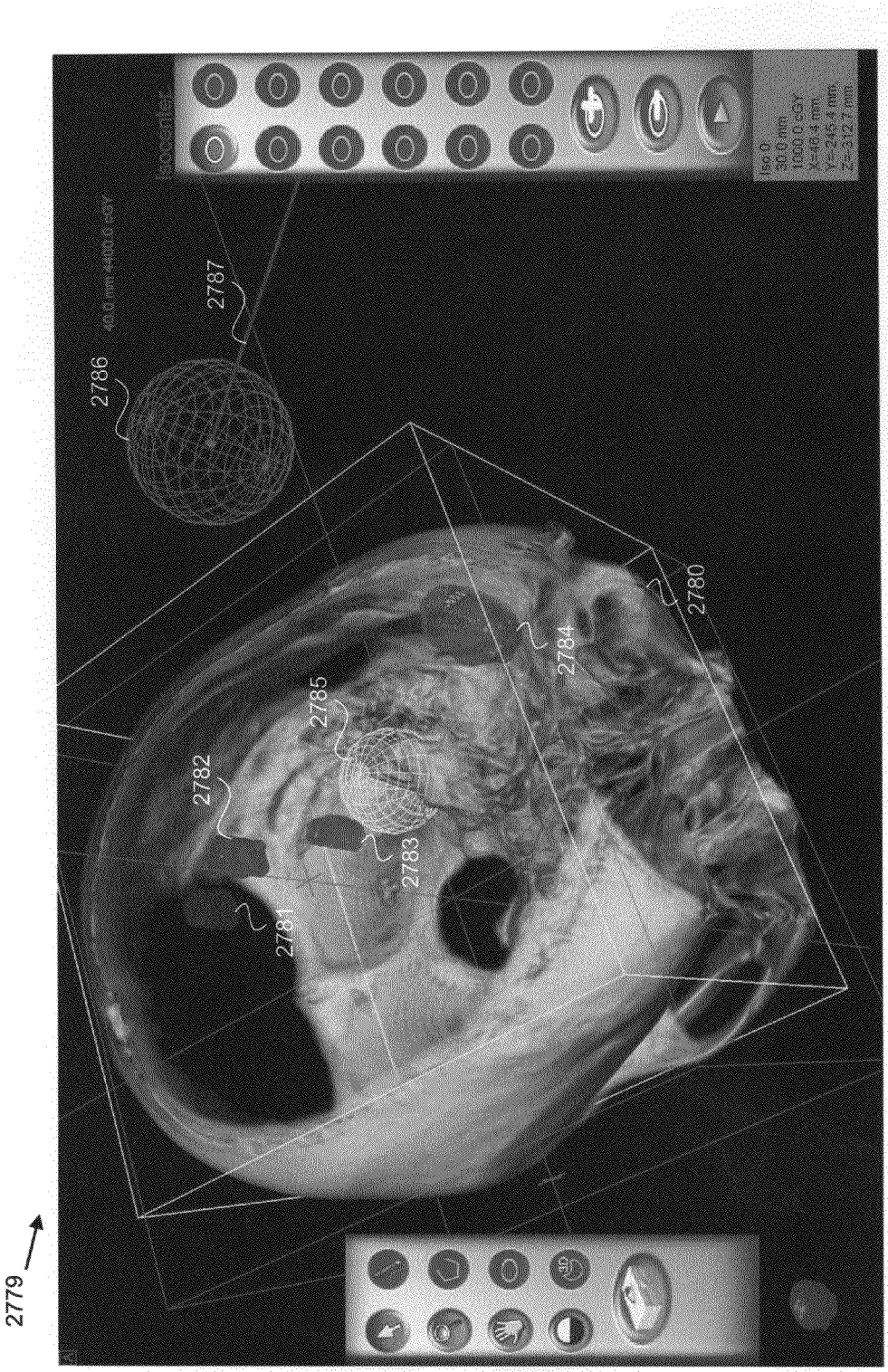
FIG. 27C illustrates a user interface for the plan task as displayed in a stereoscopic display of a treatment planning system, in accordance with another embodiment of the present invention.

Referring to FIG. 27C, a 3D stereoscopic user interface 2779 for forward planning is illustrated, in accordance with one embodiment of the present invention. Illustrated in FIG. 27C is a CT volume 2780, in which contours 2781-2784 have been delineated for numerous tumors. A single isocenter 2785 has been generated. A "create-new-isocenter" command has been issued, causing another isocenter 2786 to appear at the tip of a virtual pointer 2787. A 6D input device (e.g., an electronic pointer) may be moved in a user space to cause the virtual pointer 2787 and the new isocenter 2786 to be repositioned.

Figure 27D:
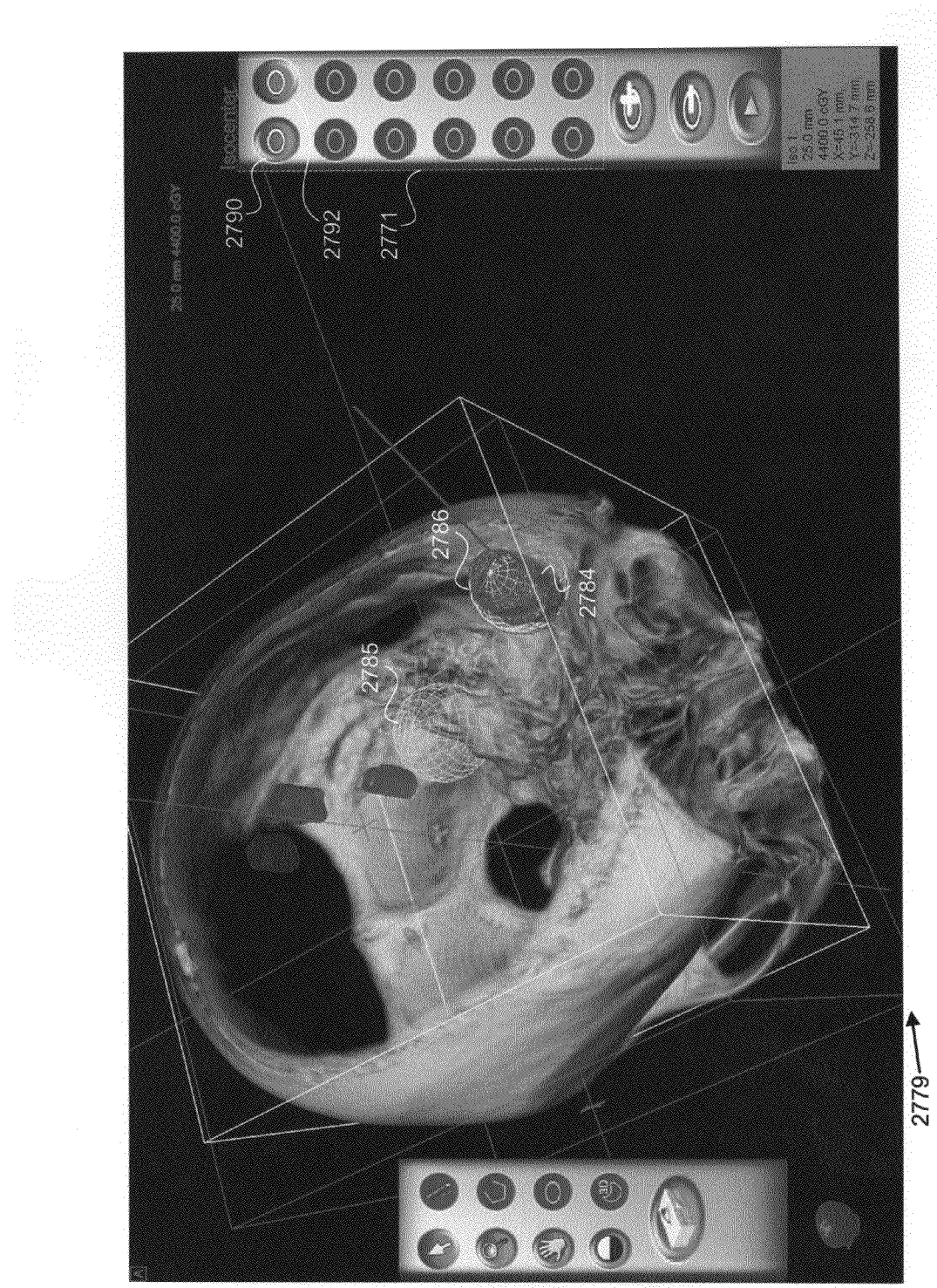
FIG. 27D illustrates a user interface for the plan task as displayed in a monoscopic display of a treatment planning system, in accordance with another embodiment of the present invention.

FIG. 27D illustrates the same user interface of FIG. 27C after the new isocenter 2786 has been moved to contour 2784 and resized. Note that in FIG. 27D the new isocenter 2786 is active (represented as a colored (e.g., yellow) wireframe), and the preexisting isocenter 2785 is inactive (represented as a colored (e.g., white) wireframe). Note also that isocenter list 2771 contains two isocenter symbols. A first isocenter symbol 2790 represents inactive isocenter 2785, and a second isocenter symbol 2792 represents active isocenter 2786.

In one embodiment, isocenters may be generated using a manual mode or a smart mode. Using the manual mode, a user places a new isocenter at a desired location, and then manually adjusts a size and dose of the isocenter (e.g., using 6D input devices). Using the smart mode, the user places a new isocenter proximate to a target (e.g., such that at least a portion of the isocenter overlaps a portion of the target). The size of the isocenter, collimator size for the isocenter, and center position of the isocenter are then automatically computed. This causes the isocenter to automatically be repositioned and resized. For example, an isocenter may be resized so that it just covers an entire target, and repositioned on the center of mass of the target (e.g., as computed using intensity values).

Inverse Planning in a Virtual Environment

Figure 28A:
FIG. 28A illustrates a user interface for the plan task as displayed in a stereoscopic display of a treatment planning system, in accordance with still another embodiment of the present invention.
Figure 28B:
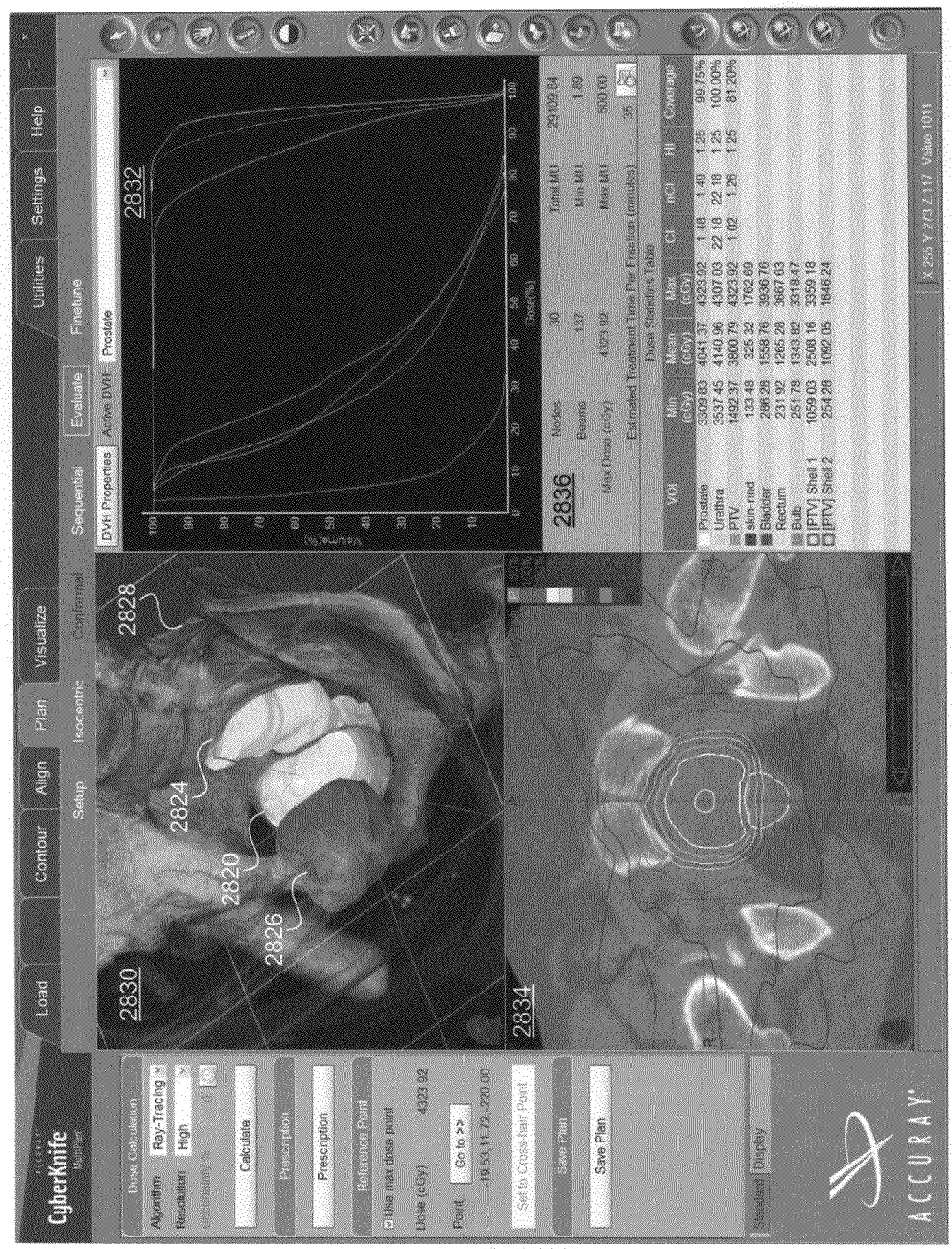
FIG. 28B illustrates a user interface for the plan task as displayed in a monoscopic display of a treatment planning system, in accordance with another embodiment of the present invention.
Figure 29:
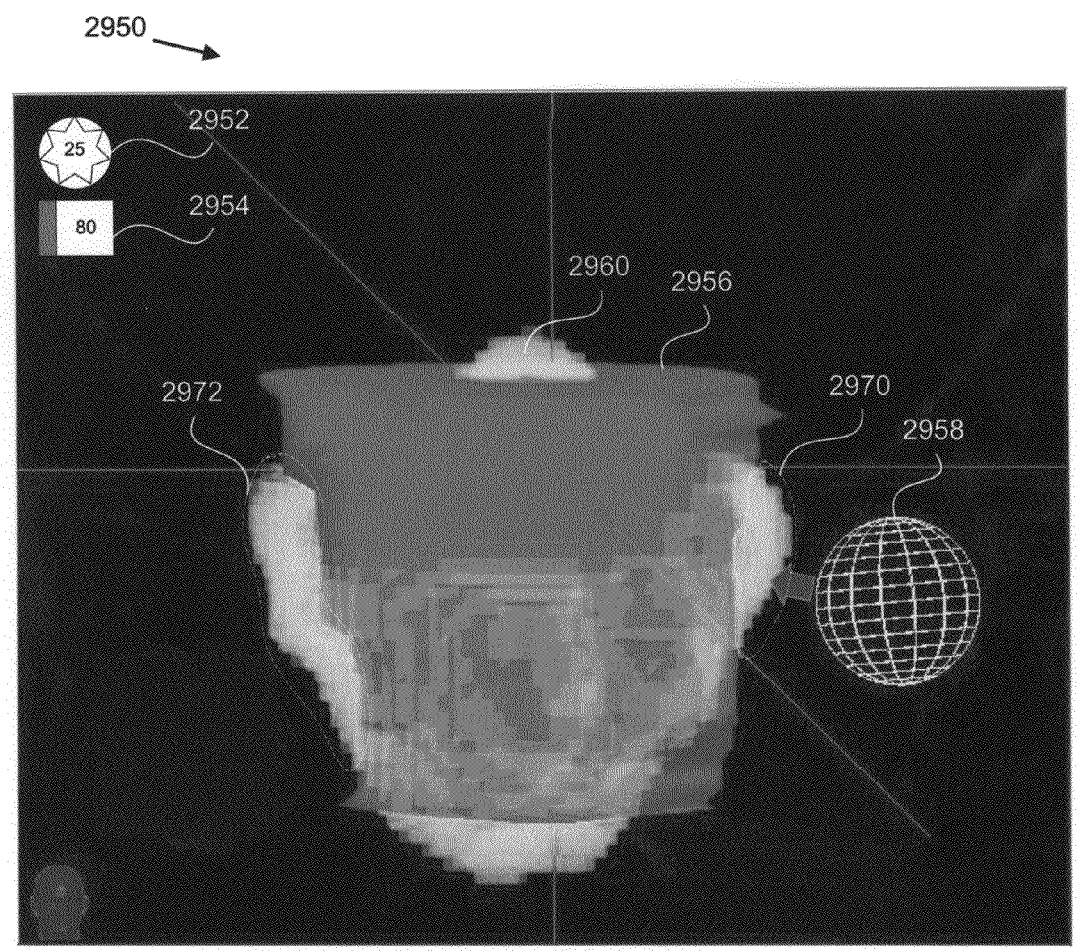
FIG. 29 illustrates a 3D user interface for the plan task that includes a dose bumper tool, in accordance with one embodiment of the present invention.

FIGS. 28A and 28B show a 3D stereoscopic user interface 2800 and monoscopic user interface 2810 for the plan task, in which an inverse planning option (e.g., a conformal planning option 2734) has been selected, in accordance with one embodiment of the present invention. Inverse planning is a method for creating treatment plans for more recent radiotherapy and radiosurgery systems. The inverse planning process is often a multi-iteration process. After each of the iterations, the constraints (or the input) to the planning algorithm may be refined by the user. With high quality constraints, the inverse planning can generally generate better plans than isocentric planning in a shorter amount of time.

In conformal planning (so-called because of the goal of having the generated isocontours conform to the shape of the target), the treatment planning software may use an iterative or non-iterative optimization algorithm to produce conformal plans giving a balance of homogeneity and conformality. In one embodiment, in order to start a conformal plan, at least one region designated as a target is defined. For example and without limitation, conformal planning takes advantage of an image-guided, robotic-based radiation treatment system (e.g., for performing radiosurgery) such as the CyberKnife® System, because the LINAC positioning mechanism (e.g., robotic arm 4052 of FIG. 32) can move around freely with multiple degrees of freedom, allowing the radiation beams of the LINAC to point anywhere in space.

When a critical structure and target volume are close together, conformal planning (or another form of inverse planning) may be performed to spare the critical structures. The virtual environment can be used to modify the planning constraints for use in inverse planning interactively, and in a more intuitive way than a standard display environment. The virtual environment may provide a user with tools for manipulating constrain points, adjusting dose shells, and painting the dose directly (as may be necessary for a low dose or cold spot).

Referring to the inverse planning user interface of FIGS. 28A-28B, some of the planning constraints that can be refined interactively by the user in a virtual planning environment include prescription dose volume, volume constraints, VOI constraints and shell constraints. 3D delineation tools may also be used, for example, to define and/or edit the volume, VOI and shell constraints in the virtual environment.

Based on specified minimum dose to the target region and the maximum dose to the critical region, the treatment planning software generates the dose isocontour for the target region. The dose isocontour represents a given dose percentage (e.g., 60%, 70%, 80%, etc.) of a specified prescription dose for the target region. Ideally, the dose isocontour should perfectly match the contour of the target region. In some cases, the dose isocontour generated by the treatment planning software is not optimal, and can include portions of the critical region.

FIGS. 28A-28B illustrate a 3D target volume 2820, a first critical structure 2824 and a second critical structure 2826 after completing the plan task using conformal planning. The 3D target volume 2820 is targeted for treatment, and the critical structures 2824, 2826 are positioned near the pathological anatomy of the 3D target volume 2820. Therefore, selection of the position and dose delivered for each radiation beam delivered to the patient during treatment can be critical. A user can pan, rotate and zoom the virtual space shown in FIG. 28A to view where the critical structures are receiving radiation. In one embodiment, areas in which the radiation isocontour intersects the critical structures are shown in a different color than the isocontour and/or the critical structures.

In one embodiment, A VOI dose constraint panel (not shown) is provided in the 3D user interface 2800 that allows the user to add, delete, or delete all of the point constraints and/or surface constraints. After a point constraint or surface constraint is added, the user may then define whether that constraint point is a minimum or maximum constraint, the limit value, and the weight. A user may click on a position on the displayed image and a point constraint may appear, for example, as a small dot or cross-hair planar view. The point constraint may be displayed with its associated values (e.g., position, percentage, and dose).

FIG. 28B includes a first window 2830, second window 2832, third window 2834 and fourth window 2836. First window 2830 shows an orthographical view of a CT structure 2828, along with the target 2820 and critical structures 2824, 2826. Second Window 2832 illustrates dose volume histograms (DVH) for the target 2820 and/or the surrounding critical structures 2824, 2826. Target volume DVH and a critical volume DVH may shown one at a time or side by side in the interface for conformal planning. For example, using an iterative algorithm, with each optimization iteration, the resultant updated DVH information may be displayed in target volume DVH and a critical volume DVH. Alternatively, the DVHs may be updated after a predetermined amount of time (e.g., five seconds). In another embodiment, the DVHs may be updated after each iteration, or the predetermined time, whichever is longer.

In one embodiment, the inverse planning user interface may also display beam statistics, for example, the total MU and number of beams, the minimum non-zero MU of all currently existing beams and the maximum MU. These statistics may also be continually updated by the treatment planning system at the end of each optimization iteration.

In one embodiment, each dose isocontour for the target region may be represented by a unique color, which in turn corresponds to the percentage of the maximum dose to the entire target volume. For example, orange isocontour represents 80% dose, which indicates that everything contained within the orange dose isocontour will receive at least 80% of the maximum dose.

One parameter for inverse planning may be collimator size, which may be provided by a collimator size table. Collimator size refers to the thickness (e.g., diameter) of the radiation beam originating from the linear accelerator (e.g., LINAC 4051). For a selected target (e.g., pathological anatomy), a collimator size (e.g., 15.0, 30.0) and one or more paths available for that collimator size may be selected. In one embodiment, another parameter is minimum/maximum monitor units (MU) allowed for the beams aimed at the selected target. The user also defines a minimum dose constraint for the target region and a maximum dose constraint for a critical region. For example, a minimum dose constraint of 2400 cGy may be set for the target region and a maximum dose constraint of 1200 cGy may be set for one or both surrounding critical structures.

The treatment planning software may provide either of two types of algorithms for optimizing the dose distribution based on the user defined minimum/maximum dose constraints.

One algorithm is an iterative algorithm that optimizes deviations above the maximum dose constraint and below the minimum dose constraint. The iterative planning algorithm first generates a set of beams and performs an initial dose distribution calculation, and subsequently attempts to improve the initial dose distribution calculation by altering one or more beams. Another algorithm performs convex optimization, for example the Simplex algorithm, which involves minimizing the number of MUs subject to the minimum/maximum dose constraints. A Simplex algorithm is known in the art; accordingly, a detailed description is not provided. Alternatively, other iterative and non-iterative optimization algorithms may be used.

A combination of both algorithms may be used. For example, the plan optimization may begin with the Simplex algorithm to determine the minimal MU required, followed by the iterative algorithm. The Simplex algorithm may minimize the number of monitor units subject to the constraints and thereby require fewer monitor units than with the iterative algorithm. Weights set to 100 are exact constraints. Multiple exact constraints and/or a low value of a maximum dose may lead to issues. Relaxing these constraint weights (by setting the weight to a value less than 100) may improve the chances of finding a solution. The iterative algorithm optimizes deviations above maximum dose constraints and below minimum dose constraints. The penalty is based on the amount of deviation at each constraint point and the weight applied to each constraint. The iterative optimization may begin with a defined set of beam geometries. In one embodiment, as the optimization proceeds, beams with little dose may be retargeted to colds spots in the tumor in order to update the dose during optimization and re-optimize from the last configuration solved by the optimizer. The iterative algorithm may tend to achieve a more homogeneous solution. Beginning with the simplex method and then, after finding the first solution, using the iterative method, may enable the user to refine the plan beginning with a minimal MU solution.

The inverse planning user interface may include the ability to add or delete constraint points to improve the shape of a dose isocontour. Such constraint points may be placed at any 3-dimensional point within the 3D virtual space. Additionally, constraint surfaces may be drawn in the 3D space, or predefined constraint surfaces may be selected and placed in the 3D space using a 6D input device.

Mixed Forward and Inverse Planning

In one embodiment, the treatment planning process may involve aspects of both forward and inverse planning techniques, thereby combining the strengths of forward and inverse planning techniques. For example, the operator can utilize isocentric beam geometries or a mixture of non-isocentric and isocentric beam geometries as part of forward planning and subsequently modify the topology of isodose contours directly during inverse planning using aspects of the optimization process. The operator can control each beam for use in the treatment plan in terms of radiation emission point, a distance to the target region, an orientation, and a radiation dose weight. The treatment planning software can allow the operator to specify a set of beams (and associated paths, emission points, and dose weights) to be used as part of a forward planning process, and another set of beams to be used as part of inverse planning. The set of beams reserved for inverse planning may be optimized by utilizing one or more envelope of constraint points generated automatically by the treatment planning software.

Sequential Optimization in Virtual Environments

In standard forward planning and inverse planning, treatment-planning objectives are grouped together and optimized in a single cost function. In sequential optimization of treatment plans, on the other hand, multiple treatment-planning objectives are ordered into a sequence of individual optimization steps (referred to herein as an optimization script). Each optimization step optimizes one or more treatment-planning objectives. The ordered sequence of optimization steps may be defined by the user to prioritize the treatment-planning objectives, instead of manually defining weighting factors for each objective in the conventional single cost function approach.

For the purpose of the present description a treatment planning objective comprises three things: (i) an optimizable parameter; (ii) an optimization instruction; and (iii) a goal value. An optimizable parameter is a treatment-planning parameter that can be optimized. Optimizable parameters include (without limitation) total MU per treatment plan, MU per node, MU per beam, minimum doses for one or more targets, minimum doses for derived structures (e.g., the target), and maximum doses for one or more targets or critical structures. An optimization instruction is a direction of optimization (e.g., maximize value or minimize value).

In one embodiment, each treatment-planning objective is optimized by means of a linear programming algorithm applied to a single optimizable parameter. The optimization process comprises optimizing each of the treatment planning objectives in the ordered sequence, while obeying constraints related to values of other planning parameters (these constraints may be applied for the entire optimization process, or may be related to values of other parameters achieved through previous optimization steps). The linear programming optimization includes, for example and without limitation, a Simplex CPlex algorithm to perform the sequential optimization, or, as will be recognized by the skilled artisan, a variety of algorithms may be used to perform the sequential optimization. For example, additional optimization objectives or steps, which may not be efficiently optimized with linear programming algorithms, may use other types of optimization algorithms.

Examples of treatment-planning objectives include, without limitation, maximizing target volume coverage by a defined dose level, maximizing the minimum dose within a target volume, attempting to reduce maximum or mean dose delivered to critical structures (e.g., healthy tissue, organs, bone structures, etc) to a goal value, attempting to reduce total MUs delivered to a goal value, attempting to increase target volume dose homogeneity to a goal value, and attempting to increase conformality of the dose distribution around the target volume to a goal value. Each of these treatment-planning objectives has an associated optimizable planning parameter (e.g. maximum dose to the bladder), an optimization direction (e.g., minimize) and a goal value (e.g., 5 Gy). Alternatively, other types of treatment-planning objectives may be accomplished using sequential optimization steps. In this manner, each optimizable parameter is optimized separately and in sequence.

In one embodiment, during sequential optimization, the results of each optimization step (e.g., an optimized parameter) are applied as an additional constraint to the next optimization step as further explained below. In this manner, the treatment-planning parameter optimized at each step cannot degrade as a result of subsequent optimization steps; although, embodiments of the present invention do permit subsequent optimization steps to change a previously optimized treatment-planning parameter by at most a pre-set amount (a relaxation value, described below).

Sequential optimization is discussed in greater detail in co-pending patent application Ser. No. 12/492,793, entitled "Sequential Optimization For Treatment Planning," which is hereby incorporated by reference.

Graphical Manipulation of Dose Constraints

In treatment planning, be it forward planning, inverse planning, or a combination thereof, a user configures a set of constraints, and a treatment plan is generated from those constraints. The initially generated treatment plan may not have optimal results. For example, portions of a critical structure may receive too much radiation, or portions of a target may receive too little radiation. In such instances, a user typically changes one or more of the original constraints, and then re-computes the treatment plan. A user may need to execute multiple iterations of a planning algorithm to obtain an optimal plan. However, in typical treatment planning, a previously computed result may not be used as an input to compute a new result after one or more constraints have been added or modified.

In one embodiment of the present invention, between each iteration, the user may graphically make adjustments to the planning parameters (e.g., using tools such as a bumper tool, pen tool, etc.) via the virtual environment. These adjustments can change dose limits of a VOI, change parameters of a sequential optimization script (if a sequential optimization algorithm is used), add new constraint points, or subtract existing constraint points. In one embodiment, a previously computed final result is used as a first input, and the one or more adjustments are used as a second input to compute a new final result. This provides a more intuitive adjustment to treatment plans, and can render more accurate results in a shorter amount of time then traditional treatment planning methods.

One of the operations that can take advantage of the virtual environment is a dose bumper tool. FIG. 29 illustrates a 3D stereoscopic planning user interface 2950 that includes a dose bumper tool 2958, in accordance with one embodiment of the present invention. The stereoscopic user interface 2950 includes a 3D virtual space, in which a target VOI 2956 is displayed with an overlaid distribution of a particular dose level 2960. As shown, the dose level 2960 includes regions 2970 and 2972 that lie outside the boundary of the target 2956. The target VOI 2956 and the current dose level 2960 can be displayed in a semi-transparent mode or a wireframe mode. In either mode, the user can see both structures clearly in the 3D virtual space of the virtual environment.

In one embodiment, the stereoscopic user interface 2950 includes a bumper tool selector 2952 and a dose level selector 2954. The bumper tool selector 2952 allows the user to change properties of the bumper tool 2958, such as a size and/or shape of the bumper tool 2958. The number shown in the bumper tool selector 2952 may indicate a current size of the dose bumper tool 2958. The dose level selector 2954 allows the user to change a dose level 2960 that is currently displayed in the 3D virtual space.

The dose bumper tool 2958 is controlled by a 6D input device. For example, the user may control the dose bumper tool 2958 using a data glove, or any other 6D input device.

The dose bumper tool 2958 is used to shape the boundary of the dose level 2960. If the bumper tool 2958 is placed inside the dose level 2960 boundary initially, moving the bumper tool toward the dose level boundary will push the shape of the dose level 2960 out (expand the dose level). If the bumper tool is placed outside the dose level boundary initially, moving the bumper tool 2958 toward the dose level will push the shape of the dose level in (dent the dose level).

As the user modifies the shape of the dose level using the dose bumper tool 2958, the stereoscopic user interface 2950 displays the updated shape of the dose level on the fly. In one embodiment, once the user has finished modifying the shape of the dose level 2960, the user can start a new iteration of the optimization process (e.g., the final result of the dose distribution may be recomputed).

In one embodiment, at the beginning of the optimization process, a delta region between the original dose level boundaries and the new modified dose level boundaries is calculated. Dose constraints may be generated based on this delta region. In one embodiment, for each of the voxels on the boundary of the delta region, a new point constraint is created, with the dose value of the dose distribution selected by the bumper tool assigned to the constraint point. For inner voxels in the delta region, if the voxel is inside the new boundary of the dose level, a point constraint with a higher (than the dose level selected by the bumper tool) dose value is created. Otherwise, if the voxel is outside the new boundary of the dose level, a point constraint with a lower (than the dose level selected by the bumper tool) dose value is created.

Typically, a current prescription dose level is selected as the default dose level. By applying the bumper tool 2958 to the prescription dose level, the point dose constraints generated by the process will have a great contribution to the conformality of the generated treatment plan. However, the user may also apply the dose bumper tool 2958 to a dose level that is different from the current prescription dose level. Additionally, the user may apply the dose bumper tool 2958 to multiple dose levels. In this case, a set of point constraints is generated for each level of the dose that has been used with the dose bumper tool.

In one embodiment, the dose bumper tool 2958 can also be used to initiate a plan by painting a target dose volume from scratch. In this case, there is no existing dose volume since the planning process has not started yet. The user can choose a desired prescription dose as the dose level, and use the bumper tool as a paintbrush to paint a region that the desired prescription dose is going to cover. The system can also initialize the dose level with the same region of the target VOI 2956. After the painting process, point constraints may be generated on a boundary of the painted dose region, as well as an interior of the region. The dose values for the constraint points may be assigned with a designated prescription dose. The interior point constraints may be assigned with a higher dose value.

The result of the dose bumping process can also be translated into other types of constraints to be used in a planning algorithm. For example, the delta region from a dose bumper operation can be translated into a volume constraint. The dose bumper tool described above is just one of the tools (operations) that can take advantage of the immersive planning environment.

Plan Evaluation Task

Reviewing contour and dose accuracy is one of the most important steps in the treatment planning process. In the virtual environment, a dose cloud is rendered with 3D image data using stereoscopic (or volumetric) technology. Stereoscopic and/or volumetric rendering gives the user a better depth perception as opposed to a standard workspace of a monoscopic display. This enables the user to make a better judgment about dosages near critical areas. Also, use of 6D input devices to navigate the 3D virtual space of the virtual environment can help review of the whole dosage coverage more efficiently. For example, the user may rotate the scene, and zoom in to view proximity of the dose isocontour or isocenter to one or more critical structures. By rotating, zooming and panning the view, the user may be able to accurately identify whether the dose isocontour overlaps the critical structure.

Three-dimensional filter controls may be used to operate on the opacity of the 3D image. As such, anything in the image having intensity less than a selected intensity may be transparent in the volume rendering. Anything with intensity greater than that of the selected intensity may be fully opaque. By manipulating the three-dimensional filter, different structures in the image may be hidden or highlighted.

In order to help a medical clinician delineate a volume of interest structure, the treatment planning software may apply a filter to the three-dimensional CT volume and/or other 3D images to assign different gray-scale values or colors and opacities to each voxel of the intensity of the various structures. For example, a tumor may have an opacity that is different from a vascular critical structure. The opacity may be related to a frequency response of the structure resulting from the imaging radiation. In one embodiment, the three-dimensional images (e.g., CT volume) may be displayed using different colors to indicate the different structures. One example of a filter that may be used is a window level (W/L) filter. Alternatively, other filters such as a curve-based filter may be used. Filtering offers flexibility in viewing the three-dimensional images because a medical clinician may select certain filter layers to be displayed and other filter layers to be hidden. For example, the three-dimensional structure corresponding to the skin of a patient may be assigned to a filter that may be turned off and, thus, not displayed. Turning filter layers on or off within the three-dimensional image allows a user to isolate specific target regions and critical structures that may be used for forward and/or inverse planning delineation. Each critical structure may be on an individual filter layer, depending on the type of filter used and the structure characteristic used by the filter.

Sub-Volume Adjustment

One of the new ways to help the user to review the volume of interest and dose distribution coverage is to use sub-volumes to reveal internal structures. Sub-volume in the 3D virtual space is a tool that will help the user to review a subset volume instead of the whole 3D volume. The sub-volume is a two-dimensional or three-dimensional view window (or collection of view windows) that hides some features of a three dimensional image and reveals other features. The view window includes a cutting plane that can turn transparent a region (e.g., a high intensity region) to reveal its internal structure. The sub-volume (view window) can be adjusted to change the cutting plane, and thus change what portions of the image are revealed.

Figure 30A:
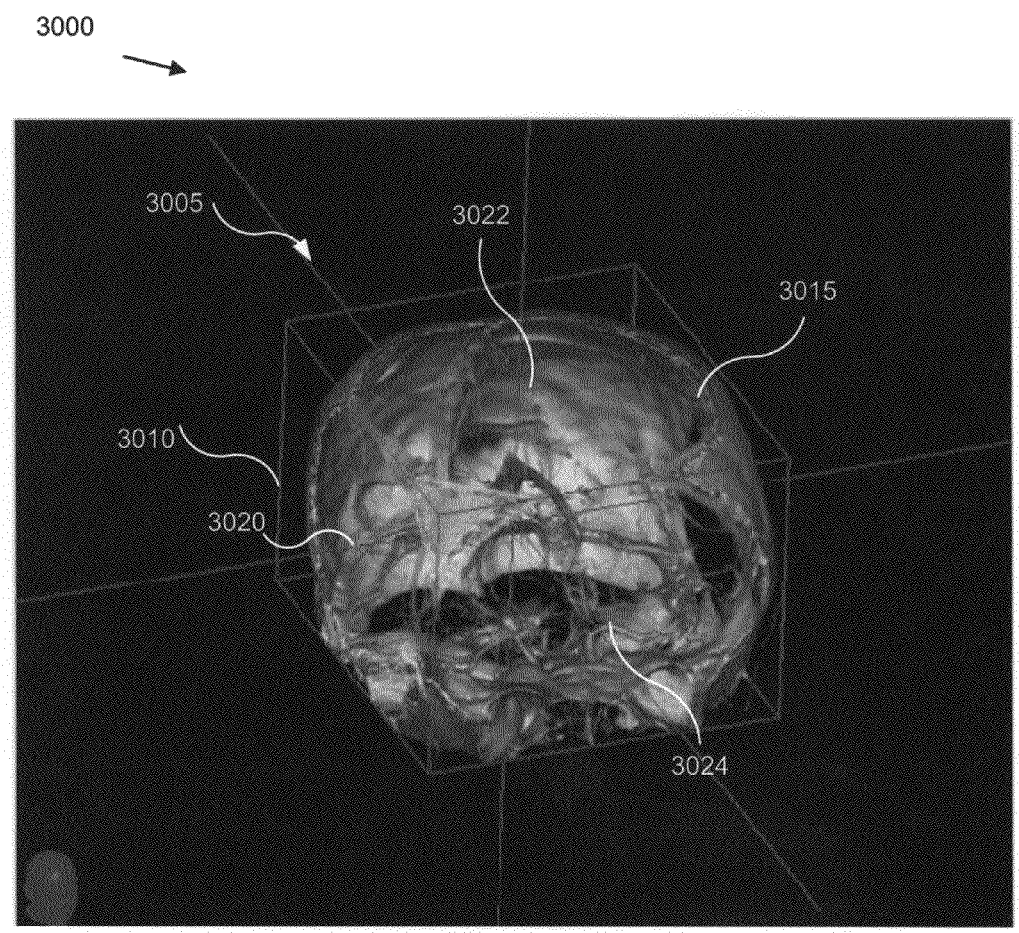
FIG. 30A illustrates one embodiment of a sub-volume perimeter on a three-dimensional image (e.g., a CT volume), in accordance with one embodiment of the present invention.

FIG. 30A illustrates one embodiment of a sub-volume perimeter 3010 on a three-dimensional image 3015 (e.g., a CT volume). In addition to filters, the treatment planning software may allow a user to define the sub-volume perimeter 3010 on the three-dimensional image 3015 to display only the structures within the sub-volume perimeter 3010. Other structures outside of the sub-volume perimeter 3010 may be excluded from the three-dimensional image 3015 displayed to the user so that the user can more readily identify certain target regions and critical structures. For example, in FIG. 30A, the regions of the 3D image 3015 that fall outside of the sub-volume perimeter 3010 are not displayed.

In one embodiment, the sub-volume perimeter 3010 may be a two-dimensional shape superimposed on the three-dimensional image 3015. By rotating the three-dimensional image 3015 and drawing multiple two-dimensional sub-volume perimeters, the user may effectively limit the displayed three-dimensional image 3015 to a three-dimensional sub-volume. Alternatively, the sub-volume perimeter 3010 may be a three-dimensional shape such as a wire mesh sphere, rectangle, or other shape. In one embodiment, a VOI (e.g., a contoured target or critical structure) is used as the sub-volume perimeter.

One advantage of displaying only a sub-volume instead of the entire volume of the three-dimensional image 3015 is the ability to isolate the target region and critical structure from surrounding structures and tissues. Another advantage of the target sub-volume is that delineation algorithms may consume less time and processor power to delineate structures within the small sub-volume compared to the volume of the entire three-dimensional image 3015. In this way, the filtering and sub-volume functions may allow a user to substantially isolate the target region and the critical structures from each other and from other structures within the volume rendering of the three-dimensional image 3015 on a graphic display. This three-dimensional isolation may significantly enhance the ability and speed of a user to identify the contours of a particular volume of interest, especially in comparison with delineating separate contours on multiple two-dimensional slices.

In one embodiment, a 3D interactor is introduced to help the user to use a 6D mouse or other 6D input device to manipulate a sub-volume box in the 3D View (in the virtual environment). In one embodiment, six interactors are added, where each interactor maps to a plane of the sub-volume box. Each interactor may enable a user to modify viewing parameters of the plane that the interactor is associated with.

In FIG. 30A, the sub-volume perimeter is a square. However, the shape of the sub-volume perimeter is not fixed. For example, faces 3020, 3022 and 3024 may be pushed or pulled using a 6D input device to modify a shape and size of the sub-volume perimeter 3010. In one embodiment, at any time, only three out of six faces of the sub-volume are visible. In one embodiment, the 3D translation (left-right-move; front-back-move; up-down-move) will be applied to those three visible faces individually. For example, if the user pans in the left direction, the corresponding face will move to left. To make the manipulation intuitive, the mapping between sub-volume faces (e.g., 3020, 3022, 3024) to three directional movement is not fixed. Such mapping depends on the orientation of each individual visible face and is dynamically built based on user perspective. FIGS. 30B and 30C show how the sub-volume faces can be manipulated in the virtual environment.

In some clinical cases, the user may want to fix the sub-volume orientation and adjust the invisible back faces so that he or she could see more content to make judgments on plan acceptability. In order to provide this flexibility, the user can control the invisible faces of the sub-volume. By default, the user is controlling the visible faces. If there is a need to control the invisible faces, a button can be pressed to switch to control of the invisible faces. In an invisible faces control mode, the manipulation is performed in the same manner as in the visible faces control mode.

A single sub-volume may be displayed, or multiple sub-volumes may be displayed at the same time. Note that the sub-volume tool and filter tool described with reference to the plan evaluation task may also be used during other tasks, such as the contour task.

Figure 31:
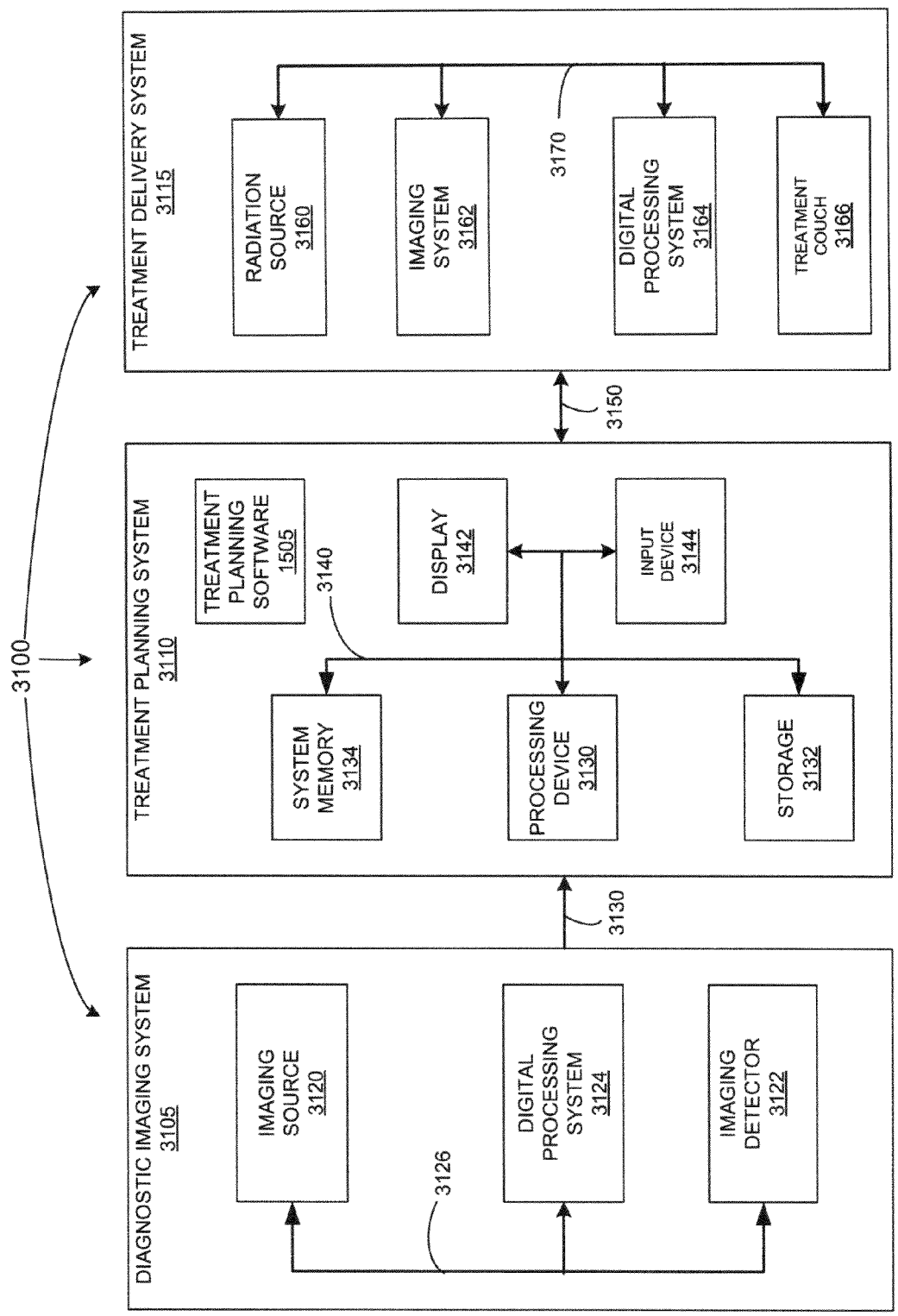
FIG. 31 illustrates one embodiment of systems that may be used to perform radiation treatment, in which features of the present invention may be implemented.

System Architecture of Treatment Delivery System, Imaging System and Treatment Planning System FIG. 31 illustrates one embodiment of systems that may be used to perform radiation treatment in which features of the present invention may be implemented. As described below and illustrated in FIG. 31, system 3100 may include a diagnostic imaging system 3105, a treatment planning system 3110, and a treatment delivery system 3115.

Diagnostic imaging system 3105 may be any system capable of producing medical diagnostic images of a volume of interest (VOI) in a patient that may be used for subsequent medical diagnosis, treatment planning and/or treatment delivery. For example, diagnostic imaging system 3105 may be a computed tomography (CT) system, a magnetic resonance imaging (MRI) system, a positron emission tomography (PET) system, an ultrasound system or the like. For ease of discussion, diagnostic imaging system 3105 may be discussed below at times in relation to a CT x-ray imaging modality. However, other imaging modalities such as those above may also be used.

Diagnostic imaging system 3105 includes an imaging source 3120 to generate an imaging beam (e.g., x-rays, ultrasonic waves, radio frequency waves, etc.) and an imaging detector 3122 to detect and receive the beam generated by imaging source 3120, or a secondary beam or emission stimulated by the beam from the imaging source (e.g., in an MRI or PET scan). In one embodiment, diagnostic imaging system 3105 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 3120 and the imaging detector 3122 are coupled to a digital processing system 3124 to control the imaging operation and process image data. Diagnostic imaging system 3105 includes a bus or other means 3126 for transferring data and commands among digital processing system 3124, imaging source 3120 and imaging detector 3122. Digital processing system 3124 may include one or more general-purpose processors (e.g., a microprocessor), special purpose processor such as a digital signal processor (DSP) or other type of device such as a controller or field programmable gate array (FPGA). Digital processing system 3124 may also include other components (not shown) such as memory, storage devices, network adapters and the like. Digital processing system 3124 may be configured to generate digital diagnostic images in a standard format, such as the DICOM (Digital Imaging and Communications in Medicine) format, for example. In other embodiments, digital processing system 3124 may generate other standard or non-standard digital image formats. Digital processing system 3124 may transmit diagnostic image files (e.g., the aforementioned DICOM formatted files) to treatment planning system 3110 over a data link 3130, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

In one embodiment treatment planning system 3110 corresponds to treatment planning system 100 of FIG. 1B. Treatment planning system 3110 includes a processing device 3130 to receive and process image data. Processing device 3130 may represent one or more general-purpose processors (e.g., a microprocessor), special purpose processor such as a digital signal processor (DSP) or other type of device such as a controller or field programmable gate array (FPGA). Processing device 3130 may be configured to execute instructions for performing the operations of the treatment planning software 1505 discussed herein that, for example, may be loaded in processing device 3130 from storage 3132 and/or system memory 3134.

Treatment planning system 3110 may also include system memory 3134 that may include a random access memory (RAM), or other dynamic storage devices, coupled to processing device 3130 by bus 3140, for storing information and instructions to be executed by processing device 3130. System memory 3134 also may be used for storing temporary variables or other intermediate information during execution of instructions by processing device 3130. System memory 3134 may also include a read only memory (ROM) and/or other static storage device coupled to bus 3140 for storing static information and instructions for processing device 3130.

Treatment planning system 3110 may also include storage device 3132, representing one or more storage devices (e.g., a magnetic disk drive or optical disk drive) coupled to bus 3140 for storing information and instructions. Storage device 3132 may be used for storing instructions for performing the treatment planning methods discussed herein.

Processing device 3130 may also be coupled to a display device 3142 for displaying information (e.g., a two-dimensional or three-dimensional representation of the VOI) to the user. The display device 3142 may be a monoscopic display or a stereoscopic display. An input device 3144, such as a keyboard, may be coupled to processing device 3130 for communicating information and/or command selections to processing device 3130. One or more other user input devices (e.g., a traditional 2D input device or a 6D input device) may also be used to communicate input data for up to 6 degrees of freedom, to select commands for processing device 3130 and to control 2D or 3D cursor movements on display 3142.

It will be appreciated that treatment planning system 3110 represents only one example of a treatment planning system, which may have many different configurations and architectures, which may include more components or fewer components than treatment planning system 3110 and which may be employed with the present invention. For example, some systems often have multiple buses, such as a peripheral bus, a dedicated cache bus, etc. The treatment planning system 3110 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3110 may be linked to treatment delivery system 3115 via a data link 3150, which may be a direct link, a LAN link or a WAN link as discussed above with respect to data link 3130. It should be noted that when data links 3130 and 3150 are implemented as LAN or WAN connections, any of diagnostic imaging system 3105, treatment planning system 3110 and/or treatment delivery system 3115 may be in decentralized locations such that the systems may be physically remote from each other. Alternatively, any of diagnostic imaging system 3105, treatment planning system 3110 and/or treatment delivery system 3115 may be integrated with each other in one or more systems.

Treatment delivery system 3115 includes a therapeutic and/or surgical radiation source 3160 to administer a prescribed radiation dose to a target volume in conformance with a treatment plan. Treatment delivery system 3115 may also include an imaging system 3162 to capture intra-treatment images of a patient volume (including the target volume) for registration or correlation with the diagnostic images described above in order to position the patient with respect to the radiation source. Treatment delivery system 3115 may also include a digital processing system 3164 to control radiation source 3160, imaging system 3162, and a patient support device such as a treatment couch 3166. Digital processing system 3164 may include one or more general-purpose processors (e.g., a microprocessor), special purpose processor such as a digital signal processor (DSP) or other type of device such as a controller or field programmable gate array (FPGA). Digital processing system 3164 may also include other components (not shown) such as memory, storage devices, network adapters and the like. Digital processing system 3164 may be coupled to radiation source 3160, imaging system 3162 and treatment couch 3166 by a bus 3170 or other type of control and communication interface.

Figure 32:
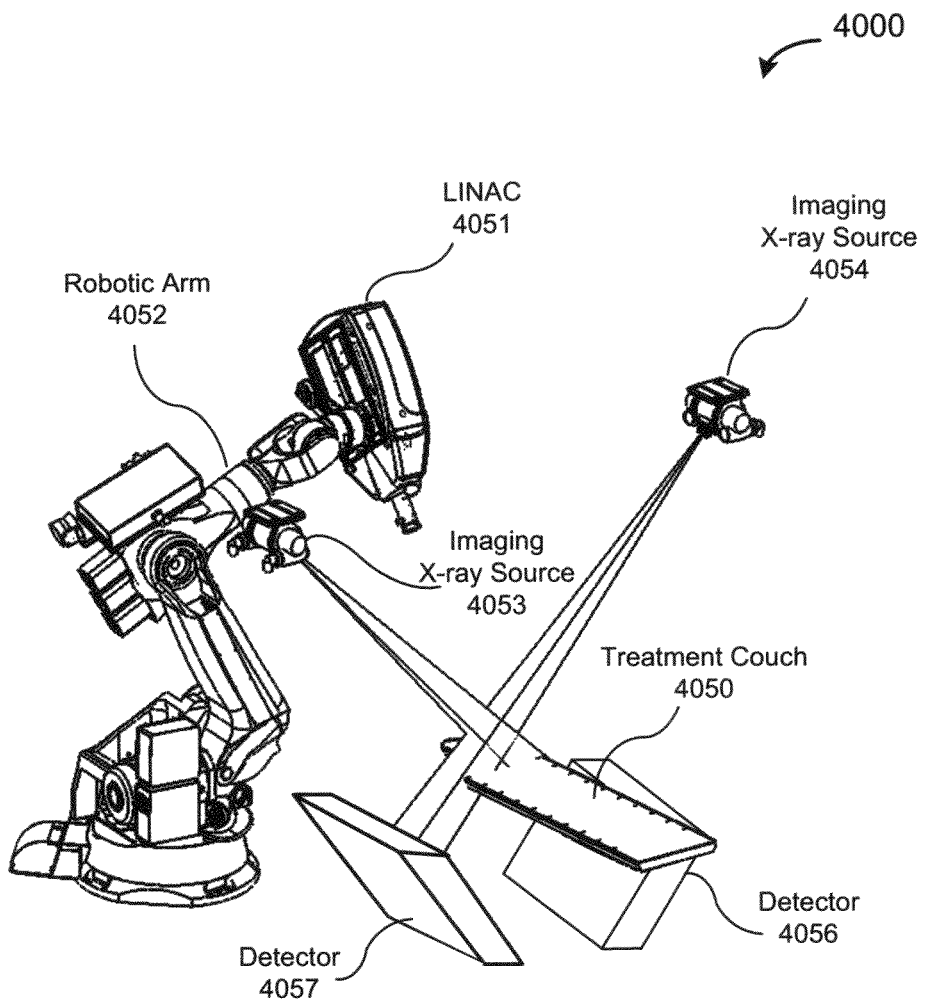
FIG. 32 illustrates a treatment delivery system that may be used with embodiments of the present invention.

In one embodiment, as illustrated in FIG. 32, treatment delivery system 4000 may be an image-guided, robotic-based radiation treatment system (e.g., for performing radiosurgery) such as the CyberKnife® system developed by Accuray Incorporated of California. In FIG. 32, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 32, imaging system 4020 may be represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray Incorporated of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

In other embodiments, yet another type of treatment delivery system 4000 may be used, for example, a stereotactic frame system such as the GammaKnife®, available from Elekta of Sweden. In such a frame-based radiosurgery system, a distributed radiation source (e.g., a cobalt 60 gamma ray source) is used to produce an approximately hemispherical distribution of simultaneous radiation beams though holes in a beam-forming assembly. The axes of the radiation beams are angled to intersect at a single point (treatment isocenter) and the beams together form an approximately spherical locus of high intensity radiation. The distributed radiation source requires heavy shielding, and as a result the equipment is heavy and immobile. Therefore, the system is limited to a single treatment isocenter. In such a system, the optimization algorithm may be referred to as a sphere packing algorithm (i.e., due to the hemispherical distribution of simultaneous radiation beams though holes in a beam-forming assembly) and determines the selection and dose weighting assigned to a group of beams forming isocenters in order to best meet provided dose constraints.

Frame-based radiotherapy and radiosurgery treatment systems employ a rigid, invasive stereotactic frame to immobilize a patient during pre-treatment imaging for diagnosis and treatment planning (e.g., using a CT scan or other 3D imaging modality, such as MRI or PET), and also during subsequent radiation treatments. These systems may be limited to intracranial treatments because the rigid frame must be attached to bony structures that have a fixed spatial relationship with target region, and the skull and brain are the only anatomical features that satisfy that criterion.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the TPS, such as the application of a beam (e.g., radiation, acoustic, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method of treatment planning, comprising:
   providing, by a treatment planning system, a three-dimensional computer-simulated virtual environment including a virtual artifact that is a three-dimensional simulation of a patient anatomy, wherein the three-dimensional simulation is generated from one or more images taken of the patient anatomy; and
   performing at least one treatment planning operation within the virtual environment, the at least one treatment planning operation comprising a contouring operation that comprises performing the following to create a three-dimensional volume of interest (VOI) contour:
      delineating a single three-dimensional volume around a three-dimensional region of the virtual artifact within the three-dimensional computer-simulated virtual environment that corresponds to at least a portion of a VOI without performing delineation within a plurality of two-dimensional slices; and
      generating the three-dimensional VOI contour in the three-dimensional computer-simulated virtual environment responsive to the single three-dimensional volume being delineated.

2. The method of claim 1, wherein the at least one treatment planning operation is associated with the virtual artifact and performed in response to a user interaction with the virtual environment, wherein the user interaction is based on an input received from an input device that receives input for three or more dimensions.

3. The method of claim 2, wherein the input device is a six-dimensional input device.

4. The method of claim 2, wherein the input device is one of a data glove, a six-dimensional mouse, or a tracking system.

5. The method of claim 1, further comprising:
   displaying the virtual artifact via at least one of a stereoscopic display or a volumetric display.

6. The method of claim 1, wherein the at least one treatment planning operation further comprises a manual image fusion operation, the method further comprising:
   receiving user input to adjust a position and orientation of a first virtual artifact along six degrees of freedom, wherein the first virtual artifact is a first three-dimensional simulation of the patient anatomy generated from a first diagnostic image;
   adjusting the position and orientation of the first virtual artifact to cause the first virtual artifact to align with a second virtual artifact, wherein the second virtual artifact is a second three-dimensional simulation of the patient anatomy generated from a second diagnostic image; and
   updating a display of the first virtual artifact and the second virtual artifact in the virtual environment as the first virtual artifact is aligned with the second virtual artifact.

7. The method of claim 6, further comprising:
   dividing the first virtual artifact and the second virtual artifact by a cutting plane, wherein the first virtual artifact is displayed on a first side of the cutting plane and the second virtual artifact is displayed on a second side of the cutting plane.

8. The method of claim 7, further comprising:
   modifying a position and orientation of the cutting plane based on user input.

9. The method of claim 1, further comprising:
   displaying a first view of the virtual artifact on a first stereoscopic display; and
   displaying an additional view of the virtual artifact on at least one of the first stereoscopic display, a second stereoscopic display or a volumetric display.

10. The method of claim 1, wherein the at least one treatment planning operation further comprises an automatic image fusion operation, the method further comprising:
    receiving user input moving a first virtual artifact onto a second virtual artifact, wherein the first virtual artifact is a first three-dimensional simulation of the patient anatomy generated from a first diagnostic image and the second virtual artifact is a second three-dimensional simulation of the patient anatomy generated from a second diagnostic image; and
    initiating the automatic image fusion operation using specified regions of the first virtual artifact and the second virtual artifact as seed locations for the automatic fusion operation, wherein the automatic image fusion operation aligns the first virtual artifact with the second virtual artifact.

11. The method of claim 1, further comprising:
    receiving user input controlling a three-dimensional drawing tool in the three-dimensional computer-simulated virtual environment, wherein a location and shape of the three-dimensional drawing tool is represented by a cursor in the three-dimensional computer-simulated virtual environment, wherein the delineating of the volume around at least the portion of the region is based on the user input, and wherein the generating of the three-dimensional VOI contour is performed as the region is delineated.

12. The method of claim 1, further comprising:
    automatically reshaping the VOI contour to conform to a three-dimensional shape of an overlapping anatomical structure based on image properties of the anatomical structure and image properties of surrounding tissue.

13. The method of claim 11, wherein the three-dimensional drawing tool is a volumetric drawing tool that draws and manipulates three-dimensional structures, the method further comprising:
    as the cursor is moved against a surface of the VOI contour, modifying the VOI contour based on an interaction of the shape of the three-dimensional drawing tool with the VOI contour.

14. The method of claim 13, further comprising:
    determining whether the cursor is located within the VOI contour or outside of the VOI contour;
    when the cursor is located within the VOI contour, as the cursor is moved against the surface of the VOI contour, expanding the VOI contour based on the interaction of the shape of the three-dimensional drawing tool with the VOI contour; and when the cursor is located outside the VOI contour, as the cursor is moved against the surface of the VOI contour, shrinking the VOI contour based on the interaction of the shape of the three-dimensional drawing tool with the VOI contour.

15. The method of claim 1, the contouring operation further comprising:

receiving user input controlling a three-dimensional drawing tool in the three-dimensional computer-simulated virtual environment, wherein a location of the three-dimensional drawing tool is represented by a cursor in the three-dimensional computer-simulated virtual environment;

delineating an additional volume around an additional region of the virtual artifact that corresponds to an additional portion of the volume of interest (VOI) based on the user input; and interpolating a space between the region and the additional region to create the three-dimensional VOI contour in the three-dimensional computer-simulated virtual environment.

16. The method of claim 1, the contouring operation further comprising:

receiving a user selection of a type of anatomy to contour;
identifying a set of image properties that are characteristic of the selected type of anatomy;
receiving a user selection of a seed point within the three-dimensional computer-simulated virtual environment, wherein the seed point is located at the region of the virtual artifact that corresponds to the volume of interest (VOI) having the selected type of anatomy; and
automatically delineating the three-dimensional VOI contour for the VOI based on a comparison of image properties of the virtual artifact to the identified set of image properties.

17. The method of claim 1, further comprising:
computing an original treatment plan based on existing treatment planning constraints, including generating a dose level structure that includes a total radiation that will be delivered to the volume of interest (VOI) and to surrounding tissue;
illustrating the dose level structure in the three-dimensional computer-simulated virtual environment;
changing a shape of the dose level structure using a drawing tool;
performing at least one of generating new treatment planning constraints or modifying the existing treatment planning constraints without user input based on the changed shape of the dose level structure; and
re-computing the treatment plan using the original treatment plan and at least one of the new treatment planning constraints or the modified treatment planning constraints.

18. The method of claim 1, further comprising:
receiving a selection of a prescription dose level;
receiving user input controlling a three-dimensional drawing tool in the three-dimensional computer-simulated virtual environment, wherein a location and shape of the three-dimensional drawing tool is represented by a cursor in the three-dimensional computer-simulated virtual environment;
tracing the region of the three-dimensional simulation of the patient anatomy that corresponds to the volume of interest (VOI) based on the user input;

generating a three-dimensional dose level structure based on the traced region;
generating point constraints based on the dose level structure; and
computing a radiation treatment plan based on the point constraints.

19. The method of claim 1, further comprising:
computing an original treatment plan based on existing treatment planning constraints, including generating a dose level structure that includes a total radiation that will be delivered to the volume of interest (VOI) and to surrounding tissue;
receiving input from a six-dimensional input device; and
performing at least one of generating new treatment planning constraints or modifying existing treatment planning constraints based on the received input.

20. A non-transitory computer readable medium including instructions that, when executed by a processing device, cause the processing device to perform a method of treatment planning, comprising:
providing, by a treatment planning system, a three-dimensional computer-simulated virtual environment including a virtual artifact that is a three-dimensional simulation of a patient anatomy, wherein the three-dimensional simulation is generated from one or more images taken of the patient anatomy; and
performing a treatment planning operation within the virtual environment, the treatment planning operation comprising a contouring operation that comprises performing the following to create a three-dimensional volume of interest (VOI) contour:
delineating a single three-dimensional volume around a three-dimensional region of the virtual artifact within the three-dimensional computer-simulated virtual environment that corresponds to at least a portion of a VOI without performing delineation within a plurality of two-dimensional slices; and
generating the three-dimensional VOI contour in the three-dimensional computer-simulated virtual environment responsive to the single three-dimensional volume being delineated.

21. A treatment planning system, comprising:
an input device that receives user input; and
a computing device, connected with the input device, to provide a computer-simulated virtual environment including a virtual artifact that is a three-dimensional simulation of a patient anatomy, wherein the three-dimensional simulation is generated from one or more images taken of the patient anatomy;
wherein the computing device is to perform a treatment planning operation within the virtual environment based on the user input, the treatment planning operation comprising a contouring operation that comprises performing the following to create a three-dimensional volume of interest (VOI) contour:
delineating a single three-dimensional volume around a three-dimensional region of the virtual artifact within the three-dimensional computer-simulated virtual environment that corresponds to at least a portion of a VOI without performing delineation within a plurality of two-dimensional slices; and
generating the three-dimensional VOI contour in the three-dimensional computer-simulated virtual environment responsive to the single three-dimensional volume being delineated.

22. A treatment planning system, comprising:
   means for providing, by the treatment planning system, a three-dimensional computer-simulated virtual environment including a virtual artifact that is a three-dimensional simulation of a patient anatomy, wherein the three-dimensional simulation is generated from one or more images taken of the patient anatomy; and
   means for performing a treatment planning operation within the virtual environment, the treatment planning operation comprising a contouring operation that comprises performing the following to create a three-dimensional volume of interest (VOI) contour:
   delineating a single three-dimensional volume around a three-dimensional region of the virtual artifact within the three-dimensional computer-simulated virtual environment that corresponds to at least a portion of a VOI without performing delineation of a plurality of two-dimensional slices; and
   generating the three-dimensional VOI contour in the three-dimensional computer-simulated virtual environment responsive to the single three-dimensional volume being delineated.

23. A method comprising:
   performing one of generating or loading a treatment plan by a treatment planning system, the treatment plan including a three dimensional rendering of a patient anatomy, wherein the three dimensional rendering is generated from one or more images of the patient anatomy;
   receiving input identifying a volume of interest (VOI) contour, wherein the VOI contour is associated with a portion of the patient anatomy and has a shape that conforms to the portion of the patient anatomy;
   defining the VOI contour as a perimeter for a three dimensional view window; and
   displaying a portion of the three dimensional simulation of the patient anatomy that is within the perimeter of the three dimensional view window while eliminating display of the three dimensional simulation of the patient anatomy that is outside of the perimeter of the three dimensional view window.

* * * * *